US011192863B2

(12) United States Patent
Gage et al.

(10) Patent No.: US 11,192,863 B2
(45) Date of Patent: *Dec. 7, 2021

(54) ANTIVIRAL COMPOUNDS AND METHODS

(71) Applicant: Biotron Limited, Sydney (AU)

(72) Inventors: Peter William Gage, Via Queanbeyan (AU); Gary Dinneen Ewart, Hackett (AU); Lauren Elizabeth Wilson, Ainslie (AU); Wayne Best, Gosnells (AU); Anita Premkumar, Nicholls (AU)

(73) Assignee: Biotron Limited, Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/554,990

(22) Filed: Aug. 29, 2019

(65) Prior Publication Data

US 2019/0389816 A1 Dec. 26, 2019

Related U.S. Application Data

(63) Continuation of application No. 15/602,526, filed on May 23, 2017, now Pat. No. 10,472,332, which is a continuation of application No. 14/615,616, filed on Feb. 6, 2015, now abandoned, which is a continuation of application No. 13/553,239, filed on Jul. 19, 2012, now abandoned, which is a continuation of application No. 10/562,296, filed as application No. PCT/AU2004/000866 on Jun. 26, 2004, now abandoned.

(30) Foreign Application Priority Data

| Jun. 26, 2003 | (AU) | 2003903251 |
| Jul. 25, 2003 | (AU) | 2003903850 |
| Aug. 29, 2003 | (AU) | 2003904692 |
| May 31, 2004 | (AU) | 2004902902 |

(51) Int. Cl.
| C07D 241/34 | (2006.01) |
| A61K 31/165 | (2006.01) |
| A61K 45/06 | (2006.01) |
| A61K 31/4965 | (2006.01) |
| A61K 31/55 | (2006.01) |
| C07C 279/22 | (2006.01) |
| A61K 31/15 | (2006.01) |
| A61K 31/47 | (2006.01) |
| A61K 31/4406 | (2006.01) |
| A61K 31/381 | (2006.01) |

(52) U.S. Cl.
CPC ............ *C07D 241/34* (2013.01); *A61K 31/15* (2013.01); *A61K 31/165* (2013.01); *A61K 31/381* (2013.01); *A61K 31/4406* (2013.01); *A61K 31/47* (2013.01); *A61K 31/4965* (2013.01); *A61K 31/55* (2013.01); *A61K 45/06* (2013.01); *C07C 279/22* (2013.01)

(58) Field of Classification Search
USPC .................................................. 514/217.05
See application file for complete search history.

(56) References Cited

U.S. PATENT DOCUMENTS

| 2,734,904 | A | | 2/1956 | Burtner |
| 3,313,813 | A | | 4/1967 | Cragoe, Jr. |
| 3,527,758 | A | | 9/1970 | Cragoe, Jr. et al. |
| 4,496,573 | A | * | 1/1985 | Studt .................... C07D 213/40 514/344 |
| 4,894,376 | A | | 1/1990 | Morad et al. |
| 5,567,734 | A | * | 10/1996 | Schwark ............... C07C 279/22 514/617 |
| 5,719,169 | A | * | 2/1998 | Kleemann ............... A61P 13/12 514/357 |
| 5,733,934 | A | * | 3/1998 | Ramakrishna ............ A61P 9/10 514/634 |
| 5,883,133 | A | * | 3/1999 | Schwark .................... A61P 9/10 514/619 |
| 6,011,059 | A | * | 1/2000 | Ahmad ..................... A61P 9/06 514/469 |
| 6,025,349 | A | | 2/2000 | Schwark et al. |
| 6,133,247 | A | | 10/2000 | Boucher, Jr. |
| 6,166,002 | A | * | 12/2000 | Weichert .................. A61P 1/04 514/182 |
| 6,420,430 | B1 | * | 7/2002 | Linz ..................... A61K 31/155 514/634 |
| 7,041,702 | B1 | * | 5/2006 | Durant ................. C07D 209/14 514/311 |
| 7,179,803 | B1 | | 2/2007 | Cox et al. |
| 10,683,263 | B2 | * | 6/2020 | Ewart .................. A61K 31/415 |

(Continued)

FOREIGN PATENT DOCUMENTS

| CN | 1323212 A | 11/2001 |
| CN | 1638772 A | 7/2005 |

(Continued)

OTHER PUBLICATIONS

Yamamoto et al. STN Accession No. 1997:590066 Chemical & Pharmaceutical Bulletin (1997), 45(8), 1282-1286.*

(Continued)

*Primary Examiner* — Nizal S Chandrakumar
(74) *Attorney, Agent, or Firm* — Amster, Rothstein & Ebenstein LLP

(57) ABSTRACT

The invention relates to compounds having antiviral and methods utilizing the compounds to treat viral infections.

5 Claims, 14 Drawing Sheets

Specification includes a Sequence Listing.

(56) References Cited

U.S. PATENT DOCUMENTS

| | | | | |
|---|---|---|---|---|
| 2004/0097544 A1* | 5/2004 | Lang | ............... | A61K 31/155 514/309 |
| 2015/0313909 A1 | 11/2015 | Ewart et al. | | |

FOREIGN PATENT DOCUMENTS

| | | | |
|---|---|---|---|
| DE | 2531343 | A | 2/1977 |
| DE | 200 618/6 | | 5/1983 |
| DE | 4301739 | A1 | 7/1994 |
| EP | 0755919 | A2 | 1/1997 |
| FR | 1435379 | A | 4/1966 |
| IN | 177137 | | 11/1996 |
| JP | H07-25768 | A | 1/1995 |
| JP | H07-89859 | A | 4/1995 |
| JP | H08-225513 | A | 9/1996 |
| JP | 09067332 | * | 9/1997 |
| JP | H9-67332 | A | 11/1997 |
| JP | H10316647 | A | 12/1998 |
| JP | 2002-527397 | | 8/2002 |
| JP | 2002-528460 | | 9/2002 |
| JP | 2003-563559 | | 3/2003 |
| JP | 2003-73280 | | 12/2003 |
| JP | 2005-522425 | | 7/2005 |
| WO | 199920599 | A1 | 4/1999 |
| WO | 199931267 | A1 | 6/1999 |
| WO | 0021538 | A1 | 4/2000 |
| WO | 200112805 | A1 | 2/2001 |
| WO | 03/063869 | A1 | 8/2003 |

OTHER PUBLICATIONS

Pamnani, Hypertension. May 1988; 11 (5):445-51.*
Bream, STN Accession No. 1976:12322 Arzneimittel-Forschung (1975), 25(10), 1477-82.*
Ahmad, Journal of Medicinal Chemistry (2001), 44(20), 3302-3310.*
Phillips, Journal of the American Chemical Society (1954), 76, 574-6.*
Yamamoto et al. Chemical & Pharmaceutical Bulletin (1997), 45(8), 1282-1286.*
Bream, Arzneimittel-Forschung (1975), 25(10), 1477-82.*
Naik, Indian (1996), IN 177137 B 19961116.*
"Amiloride," The Merck Index Online, internet address https://www.rsc.org/Merck-Index/monograph/m1671/amiloride? q=unauthorize, last revised in 2013, Royal Society of Chemistry, 2 pages.
Naik et al., STN Accession No. 2003:1007305, Document No. 140:27667, Abstract of IN 177137, Nov. 16, 1996.
Yamamoto et al., "Structural Requirements for Potent Na/H Exchange Inhibitors Obtained from Quantitative Structure-Activity Relationships of Monocyclic and Bicyclic Arolylguanidines," Chemical & Pharmaceutical Bulletin, 1997, vol. 45, No. 8, pp. 1282-1286.
Bream, STN Accession No. 1997:590066, Document No. 84:12322, Abstract of Arzeimittel-Forschung (1975), 25(10), 1477-82.
Ahmed et al., "Arylcyclopropanecarboxyl Guanidines as Novel, Potent, and Selective Inhibitors' of the Sodium Hydrogen Exchanger Isoform-1," Journal of Medicinal Chemistry, 2001, vol. 44, No. 20, pp. 3302-3310.
Ewart et al., "Amiloride derivatives block ion channel activity and enhancement of virus-like particle budding caused by HIV-1 protein Vpu," European Biophysics Journal, 2002, vol. 31, No. 1, pp. 26-35.
Ewart et al., "Potential New Anti-Human Immunodeficiency Virus Type 1 Compounds Depress Virus Replication in Cultured Human Macrophages," Antimicrobobial Agents Chemotherapy, 2004, vol. 48, No. 6, pp. 2325-2330.

Giacometti et al., "In vitro anti-cryptosporidial activity of cationic peptides alone and in combination with inhibitors of ion transport systems," J. Antimicrob. Chemotherapy, 2000, vol. 15, No. 5, pp. 651-654.
Goerdeler and Mertens, "1 ,2,4-Thiadiazoles, XX. A Study of 3-Amino-thiadiazoles," Chemische Berichte, 1970, vol. 103, No. 6, pp. 805-1814.
Hennrich et al., "Fluorescent anion receptors with iminoylthiourea binding sites-selective hydrogen bond mediated recognition of C032-, HC03- and HP042-," Tetrahedron Letters, 2001, vol. 42, No. 15, pp. 2805-2808.
Rogister et al., "Novel inhibitors of the sodium-calcium exchanger: benzene ring analogues of N-guanidino substituted amiloride derivatives," European Journal of Medicinal Chemistry, 2001, vol. 36, No. 7-8, pp. 597-614.
Anja Garritsen et al., "Interaction of amiloride and its analogues with adenosine A 1 receptors in calf brain," Dec. 31, 1990, Biochemical Pharmacology, 40(4), 827-834.
Louis Simchowitz et al., "Inhibition of Chemotactic Factor-Activated $Na^+/H^+$ Exchange in Human Neutrophils by Analogues of Amiloride: Structure-Activity Relationships in the Amiloride Series," Dec. 31, 1986, Molecular Pharmacology, 30(2), 112-120.
Budavari S. et al., The Merck Index; An Encyclopedia of Chemicals, Drugs and Biologicals, 12th Edition, 1996, p. 72.
Bredereck et al., "Synthase von O.N- bzw. N.N-Acetalen der Acylisocyanate aus Amidacetalen bzw. einem Aminal-tert.-butylester und N-Halogen-carbonsaureamiden, Halogenharnstoffen und N-Chlor-urethan", Chern. Ber. 103, 245-255 (1970).
Dodd et al., "Solid-phase synthesis of N, N'-substituted acylguanidines," Tetrahedron Letters, 42 (2001) 1259-1262.
Ito et al., "Uberd die Synthese von N1—substituierten N8-Acylguanidinen, (Voriaufige Mitt.), Benzoylverbindungen," (Pharmazeutische Hochschule Meiji), vol. 9, No. 3., pp. 245-248, (1961).
STN Database Accession No. 67 : 100033 CA; Archiv Der Pharmazie und Berichteder Deutschen Pharmazeutischen Gesellschaft, 300 (7): 609-615 (1969).
web.archive.orglwebl19990831162814/http:/lwww.probes.com/servlets/product?item=6905; Biodipy FL amiloride, Molecular Probes, Inc. Catalog (online) (1989).
European Search Report and Written Opinion, Jun. 5, 2013 (date of completion) issued in connection with European Patent Application No. EP 13 16 4504, 13 pages.
Canadian Examination Report dated Jan. 28, 2011 in connection with Canadian Application No. 2,529,949, 5 pages.
STN International Abstracts: CAS RN 16565-12-1, retrieved on Oct. 22, 2015.
Malyuga et al., "Antitubercular activity of guanidine derivatives," Pharmaceutical Chemistry Journal, vol. 5, No. 3, 1971, pp. 12-16.
Venkatesh et al., "Role of the Development Scientist in Compound Lead Selection and Optimization," J. Pharm. Sci., vol. 89, No. 2, Feb. 2000, pp. 145-154.
De Clercq, "Antivirals and Antiviral Strategies," Nature Reviews/Microbiology, vol. 2, Sep. 2004, pp. 704-720.
Gazina et al., "Viral Targets of Acylguanidines," Drug Discovery Today, 2012, 17 (17/18), pp. 1039-1043.
Lamb et al., "Do Vpu and Vpr of Human Immunodeficiency Virus Type 1 and NB of Influenza B Virus Have Ion Channel Activities in the Viral Life Cycles?," Virology, vol. 229, No. 1, 1997, pp. 1-11.
Iwanowicz et al., "Novel Guanidine-Based Inhibitors of Inosine Monophosphate Dehydrogenase," Bioorganic & Medicinal Chemistry Letters, vol. 12, 2002, pp. 2931-2934.
Tsuji, "Cupric Ion Catalyzed Guanidide Hydrolysis," Chem. Pharm. Bull., 1972, vol. 20, No. 3, pp. 627-628.
Schmidtke et al., "A Rapid Assay for Evaluation of Antiviral Activity Against Coxsackie Virus B3, Influenza Virus A, and Herpes Simplex Virus Type 1," Journal of Virological Methods 95, 2001, pp. 133-143.

* cited by examiner

```
         10        20        30        40        50        60        70        80
          *         *         *         *         *         *         *         *
                          ~ ++   +  ++  ~+    ~+     ~+   ~~     ~  ~        ~    ~  ++   ~  ~~
MQPIPIVAIVALVYAIIIAIVVWSIVIIEYRKILRQRKIDRLIDRLIERAEDSGNESEGEISALVEMGVEMGHHAPWDVDDL
*
```

Fig. 1A

SEQUENCE LISTING

```
<160> NUMBER OF SEQ ID NOS: 9

<210> SEQ ID NO 1
<211> LENGTH: 82
<212> TYPE: PRT
<213> ORGANISM: Homo sapiens

<400> SEQUENCE: 1

Met Gln Pro Ile Pro Ile Val Ala Ile Ala Leu Val Val Ala Ile
1               5                   10                  15

Ile Ile Ala Ile Val Val Trp Ser Ile Val Ile Ile Glu Tyr Arg Lys
            20                  25                  30

Ile Leu Arg Gln Arg Lys Ile Asp Arg Leu Ile Asp Arg Leu Ile Glu
        35                  40                  45

Arg Ala Glu Asp Ser Gly Asn Glu Ser Glu Gly Glu Ile Ser Ala Leu
    50                  55                  60

Val Glu Met Gly Val Glu Met Gly His His Ala Pro Trp Asp Val Asp
65                  70                  75                  80

Asp Leu

<210> SEQ ID NO 2
<211> LENGTH: 24
<212> TYPE: DNA
<213> ORGANISM: homo sapiens

<400> SEQUENCE: 2
agtaggatcc atgcaaccta tacc                                          24

<210> SEQ ID NO 3
<211> LENGTH: 24
<212> TYPE: DNA
<213> ORGANISM: homo sapiens

<400> SEQUENCE: 3
tctggaattc tacagatcat caac                                          24

<210> SEQ ID NO 4
<211> LENGTH: 76
<212> TYPE: PRT
<213> ORGANISM: homo sapiens

<400> SEQUENCE: 4
```

```
Met Tyr Ser Phe Val Ser Glu Glu Thr Gly Thr Leu Ile Val Asn Ser
1               5                   10                  15

Val Leu Leu Phe Leu Ala Phe Val Val Phe Leu Val Thr Leu Ala
            20                  25                  30

Ile Leu Thr Ala Leu Arg Leu Cys Ala Tyr Cys Cys Asn Ile Val Asn
            35                  40                  45

Val Ser Leu Val Lys Pro Thr Val Tyr Val Tyr Ser Arg Val Lys Asn
        50                  55                  60

Leu Asn Ser Ser Glu Gly Val Pro Asp Leu Leu Val
65                  70                  75
```

<210> SEQ ID NO 5
<211> LENGTH: 40
<212> TYPE: PRT
<213> ORGANISM: homo sapiens

<400> SEQUENCE: 5

```
Met Tyr Ser Phe Val Ser Glu Glu Thr Gly Thr Leu Ile Val Asn Ser
1               5                   10                  15

Val Leu Leu Phe Leu Ala Phe Val Val Phe Leu Val Thr Leu Ala
            20                  25                  30

Ile Leu Thr Ala Leu Arg Leu Cys
            35                  40
```

<210> SEQ ID NO 6
<211> LENGTH: 77
<212> TYPE: PRT
<213> ORGANISM: homo sapiens

<400> SEQUENCE: 6

```
Met Phe Leu Lys Leu Val Asp Asp His Ala Leu Val Val Asn Val Leu
1               5                   10                  15

Leu Trp Cys Val Val Leu Ile Val Ile Leu Leu Val Cys Ile Thr Ile
            20                  25                  30

Ile Lys Leu Ile Lys Leu Cys Phe Thr Cys His Met Phe Cys Asn Arg
            35                  40                  45

Thr Val Tyr Gly Pro Ile Lys Asn Val Tyr His Ile Tyr Gln Ser Tyr
        50                  55                  60

Met His Ile Asp Pro Phe Pro Lys Arg Val Ile Asp Phe
65                  70                  75
```

<210> SEQ ID NO 7
<211> LENGTH: 83
<212> TYPE: PRT
<213> ORGANISM: homo sapiens

<400> SEQUENCE: 7

```
Met Phe Asn Leu Phe Leu Thr Asp Thr Val Trp Tyr Val Gly Gln Ile
1               5                   10                  15

Ile Phe Ile Phe Ala Val Cys Leu Met Val Thr Ile Val Val Ala
            20                  25                  30

Phe Leu Ala Ser Ile Lys Leu Cys Ile Gln Leu Cys Gly Leu Cys Asn
            35                  40                  45

Thr Leu Val Leu Ser Pro Ser Ile Tyr Leu Tyr Asp Arg Ser Lys Gln
        50                  55                  60

Leu Tyr Lys Tyr Tyr Asn Glu Glu Met Arg Leu Pro Leu Leu Glu Val
65                  70                  75                  80

Asp Asp Ile
```

```
<210> SEQ ID NO 8
<211> LENGTH: 63
<212> TYPE: PRT
<213> ORGANISM: homo sapiens

<400> SEQUENCE: 8

Ala Leu Glu Asn Leu Val Ile Leu Asn Ala Ala Ser Leu Ala Gly Thr
1               5                  10                  15

His Gly Leu Val Ser Phe Leu Val Phe Phe Cys Phe Ala Trp Tyr Leu
            20                  25                  30

Lys Gly Arg Trp Val Pro Gly Ala Val Tyr Ala Phe Tyr Gly Met Trp
        35                  40                  45

Pro Leu Leu Leu Leu Leu Leu Ala Leu Pro Gln Arg Ala Tyr Ala
    50                  55                  60

<210> SEQ ID NO 9
<211> LENGTH: 40
<212> TYPE: PRT
<213> ORGANISM: homo sapiens

<400> SEQUENCE: 9

Ala Leu Arg His Pro Gly Phe Thr Val Ile Ala Leu Phe Leu Ala His
1               5                  10                  15

Ala Ile Gly Thr Ser Ile Thr Gln Lys Gly Ile Ile Phe Ile Leu Leu
            20                  25                  30

Met Leu Val Thr Pro Ser Met Ala
            35                  40
```

ANTIVIRAL COMPOUNDS AND METHODS

CROSS-REFERENCE TO RELATED APPLICATIONS

This application is a continuation of U.S. patent application Ser. No. 15/602,526, filed May 23, 2017, now allowed, which is a continuation of U.S. patent application Ser. No. 14/615,616, filed Feb. 6, 2015, which is a continuation of U.S. patent application Ser. No. 13/553,239, filed Jul. 19, 2012, which is a continuation of U.S. application Ser. No. 10/562,296, filed Dec. 22, 2005, which is a U.S. national phase of PCT International Patent Application No. PCT/AU2004/000866, filed Jun. 26, 2004, which claims priority to Australian Application No. 2004902902, filed May 31, 2004, Australian Application No. 2003904692, filed Aug. 29, 2003, Australian Application No. 2003903850, filed Jul. 25, 2003, and Australian Application No. 2003903251, filed Jun. 26, 2003, the contents of each of which are incorporated herein by reference in their entirety.

FIELD OF INVENTION

The present invention relates to methods for retarding, reducing or otherwise inhibiting viral growth and/or functional activity. The invention also relates to compounds and compositions suitable for use in the methods.

BACKGROUND OF THE INVENTION

Currently, there is a great need for the development of new treatments that are effective against viral infections, particularly against viral infections which are associated with high morbidity and mortality, and which impact on sizable populations. Treatments currently available are inadequate or ineffective in large proportions of infected patients.

For example, in ameliorating AIDS symptoms and prolonging life expectancy, a measure of success has been achieved with drugs targeting the viral reverse transcriptase and protease enzymes (Miller and Sarver, 1997; Mitsuya, 1992; Moore, 1997; and Thomas and Brady, 1997). However, no single treatment method is completely effective against HIV infection. (Barry et al, 1998; Deeks, 1998; Miles, 1997; Miles, 1998; Moyle et al, 1998; Rachlis and Zarowny, 1998; Veil et al, 1997; Volberding and Deeks, 1998; and Volberdin, 1998).

PCT application PCT/AU99/00872 describes the use of compounds 5-(N,N-hexamethylene)-amiloride and 5-(N,N-dimethyl)-amiloride in the treatment of HIV infection.

Another virus considered to be a significant human pathogen is the Hepatitis C virus (HCV). This is a significant human pathogen in terms of both cost to human health and associated economic costs. HCV causes chronic hepatitis and cirrhosis and is the leading indicator for liver replacement surgery. In 2002 the Centre for Disease Control and Prevention estimated that more than 4 million people were infected in the USA alone and that approximately 8,000 to 10,000 die as a result of chronic HCV infection yearly. There is no known cure or vaccine. More effective pharmacological agents are urgently required.

A further well-known family of pathogenic viruses are the Coronaviruses. Coronaviruses (Order Nidovirales, family Coronaviridae, Genus *Coronavirus*) are enveloped positive-stranded RNA viruses that bud from the endoplasmic reticulum-Golgi intermediate compartment or the cis-Golgi network (Fischer, Stegen et al. 1998; Maeda, Maeda et al. 1999; Corse and Machamer 2000; Maeda, Repass et al. 2001; Kuo and Masters 2003)

Coronaviruses infect humans and animals and it is thought that there could be a coronavirus that infects every animal. The two human coronaviruses, 229E and OC43, are known to be the major causes of the common cold and can occasionally cause pneumonia in older adults, neonates, or immunocompromised patients (Peiris, Lai et al. 2003). Animal coronaviruses can cause respiratory, gastrointestinal, neurological, or hepatic diseases in their host (Peiris, Lai et al. 2003). Several animal coronavirus are significant veterinary pathogens (Rota, Oberste et al. 2003).

Severe acute respiratory syndrome (SARS) is caused by a newly identified virus. SARS is a respiratory illness that has recently been reported in Asia, North America, and Europe (Peiris, Lai et al. 2003). The causative agent of SARS was identified as a coronavirus. (Drosten, Gunther et al. 2003; Ksiazek, Erdman et al. 2003; Peiris, Lai et al. 2003). The World Health Organization reports that the cumulative number of reported probable cases of SARS from 1 Nov. 2002 to the 11 Jul. 2003 is 8,437 with 813 deaths, nearly a 10% death rate. It is believed that SARS will not be eradicated, but will cause seasonal epidemics like the cold or influenza viruses (Vogel 2003).

To improve the prospect of treating and preventing viral infections, there is an on-going need to identify molecules capable of inhibiting various aspects of the viral life cycle.

It is an object of the present invention to overcome or ameliorate at least one of the disadvantages of the prior art, or to provide a useful alternative.

Any discussion of the prior art throughout the specification should in no way be considered as an admission that such prior art is widely known or forms part of common general knowledge in the field.

SUMMARY OF THE INVENTION

The inventors have surprisingly found that certain compounds that fall under the classification of substituted acylguanidines have antiviral activity against viruses from a range of different virus families. Without intending to be bound by any particular theory or mechanism of action, and despite current dogma, it appears possible that viral replication can be retarded by inhibiting or otherwise down-regulating the activity of ion channels expressed in the host cell. Thus, the negative impact of the compounds of the present invention on viral replication may be mediated by the inhibition or otherwise down-regulation of a membrane ion channel relied upon by the virus for replication. This membrane ion channel may be a viral membrane ion channel (exogenous to the host cell) or a host cell ion channel induced as a result of viral infection (endogenous to the host cell).

As an example, the compounds of the present invention may inhibit Vpu or p7 function and thereby inhibit the continuation of the respective HIV or HCV life cycle.

The SARS virus encodes an E protein which is shown for the first time, by the present inventors, to act as an ion channel. As similar E proteins are present in other coronaviruses, the compounds, compositions and methods of the present invention would have utility in the inhibition and/or treatment of infections by other coronaviruses.

The present invention is concerned with novel antiviral compounds that fall under the classification of substituted acylguanidines. It does not include in its scope the use of compounds 5-(N,N-hexamethylene)amiloride and 5-(N,N- dimethyl)-amiloride for retarding, reducing or otherwise inhibiting viral growth and/or functional activity of HIV.

Accordingly, a first aspect of the present invention provides an acylguanidine with antiviral activity.

According to a second aspect, the present invention provides an antiviral compound of Formula I

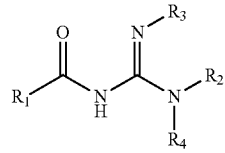

wherein R1-R4 are independently aromatic groups, heteroaromatic groups, alkylaromatic groups, alkylheteroaromatic groups, alkenylaromatic groups, alkenylheteroaromatic groups, cycloalkylaromatic groups, cycloalkylheteroaromatic groups, aryloxyalkyl groups, heteroaryloxyalkyl groups, said groups are mono or polycyclic, and are optionally substituted with one or more substitutents independently selected from hydrogen, hydroxy, nitro, halo, amino, substituted amino, alkyl-substituted amino, cycloalkyl-substituted amino, aryl-substituted amino, C1-6alkyl, C1-6alkyloxy, C3-6cycloalkyl, halo-substituted C1-6alkyl, halo-substituted C1-6alkyloxy, phenyl, C1-6alkeneyl, C3-6cycloalkeneyl, C1-6alkeneoxy, benzo, aryl, substituted aryl, PrS,

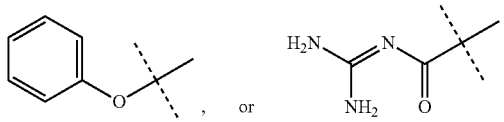

According to a third aspect, the present invention provides an antiviral compound of Formula I

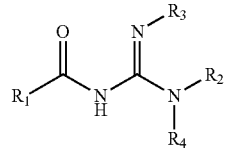

or pharmaceutically acceptable salts thereof, wherein, $R_1 =$ 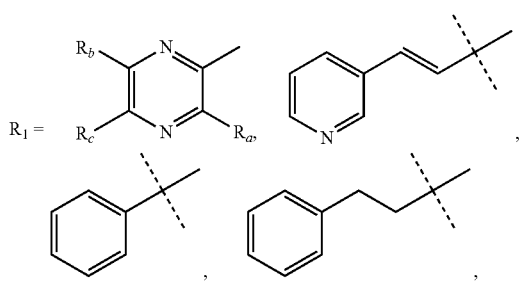

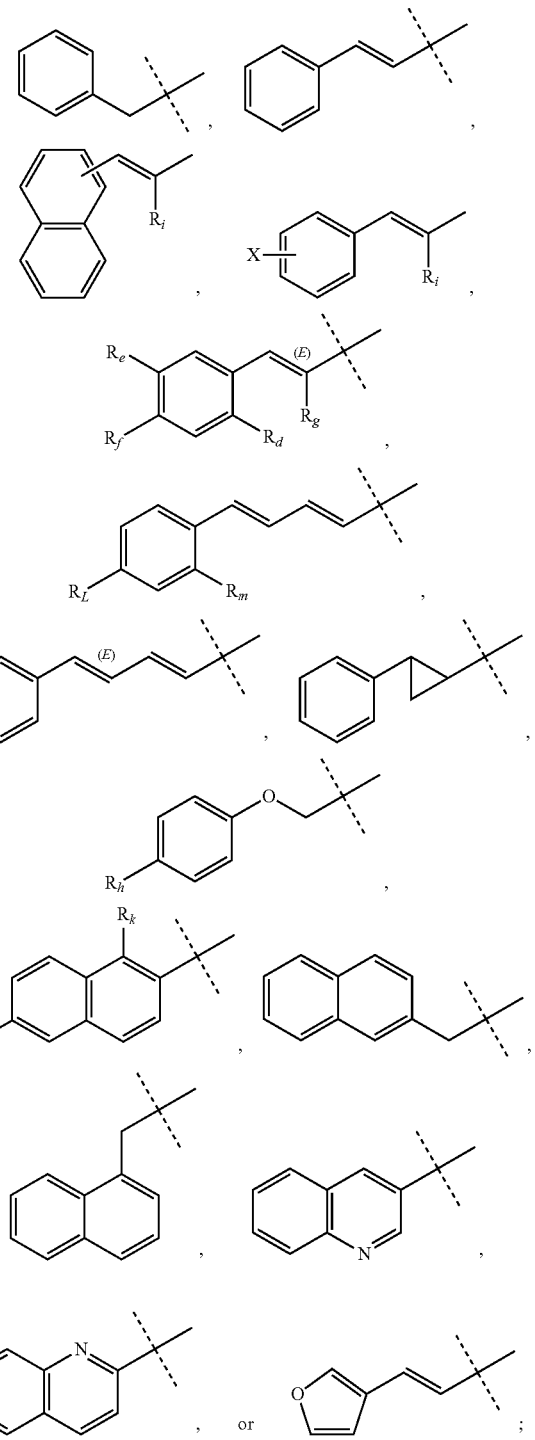

$R_2$, $R_3$ and $R_4$ are independently hydrogen,

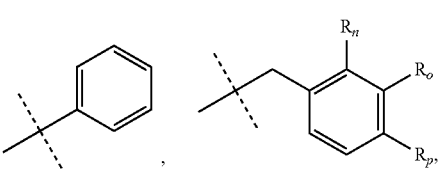

-continued

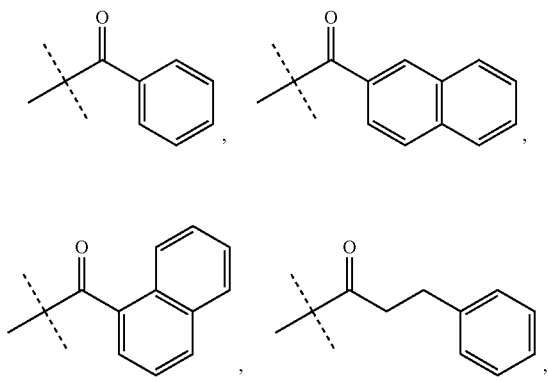

and wherein

X=hydrogen, hydroxy, nitro, halo, $C_{1-6}$alkyl, $C_{1-6}$alkyloxy, $C_{3-6}$cycloalkyl, halo-substituted $C_{1-6}$alkyl, halo-substituted $C_{1-6}$alkyloxy, phenyl, $C_{1-6}$alkeneyl, $C_{3-6}$cycloalkeneyl, $C_{1-6}$alkeneoxy, or benzo;

$R_a$, $R_b$, $R_c$, $R_d$, $R_e$, $R_f$, $R_h$, $R_k$, $R_L$, $R_m$, $R_n$, $R_o$, $R_p$ independently=hydrogen, amino, halo, $C_{1-5}$alkyl, $C_{1-5}$alkyloxy, hydroxy, aryl, substituted aryl, substituted amino, mono or dialkyl-substituted amino, cycloalkyl-substituted amino, aryl-substituted amino,

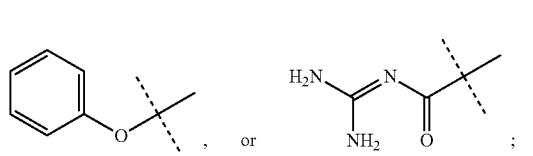

or PrS;

$R_g$, $R_i$ independently=hydrogen, hydroxy, halo, or $C_{1-5}$ alkyl;

$R_j$=hydrogen, amino, halo, $C_{1-5}$alkyl, $C_{1-5}$alkyloxy, hydroxy, aryl, substituted aryl, substituted amino, alkyl-substituted amino, cycloalkyl-substituted amino, aryl-substituted amino, PrS, Preferably, the compounds of the invention include the following:

5-(N,N-hexamethylene)amiloride comprising the structure

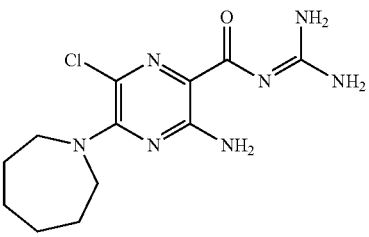 [SMILES: NC(N)=NC(=O)c1nc(Cl)c(N2CCCCCC2)nc1N]

5-(N,N-Dimethyl)amiloride hydrochloride comprising the structure

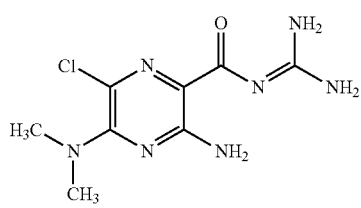

5-(N-methyl-N-isobutyl)amiloride comprising the structure

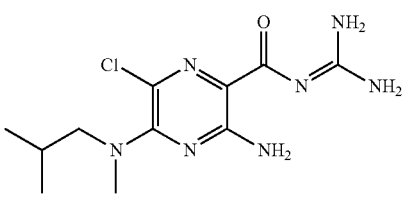 [SMILES: CC(C)CN(C)c1nc(N)c(C(=O)N=C(N)N)nc1Cl]

5-(N-ethyl-N-isopropyl)amiloride (herein referred to as EIPA), comprising the structure

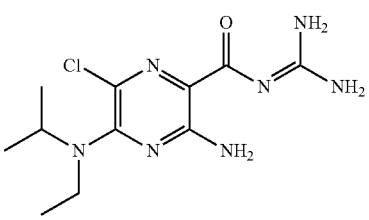 [SMILES: CCN(c1nc(N)c(C(=O)N=C(N)N)nc1Cl)C(C)C]

N-(3,5-Diamino-6-chloro-pyrazine-2-carbonyl)-N'-phenylguanidine, comprising the structure

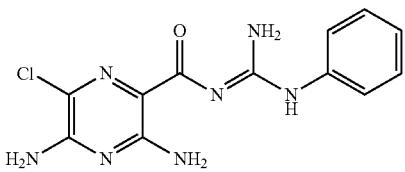 [SMILES: N/C(=N\C(=O)c1nc(Cl)c(N)nc1N)Nc1ccccc1]

N-Benzyl-N'-(3,5-diamino-6-chloro-pyrzine-2-carbonyl)-guanidine, comprising the structure

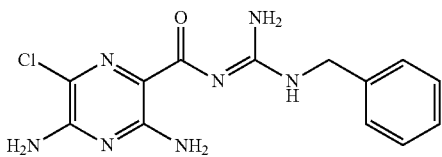 [SMILES: N/C(=N\C(=O)c1nc(Cl)c(N)nc1N)NCc1ccccc1]

3-methoxy amiloride comprising the structure comprising the structure

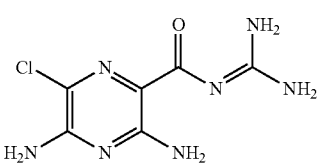

3-methoxy-5-(N,N-Hexamethylene)-amiloride comprising the structure

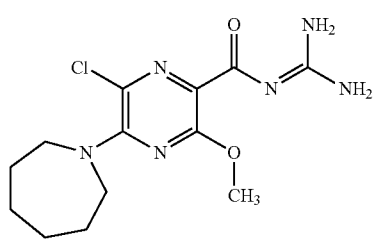 [SMILES: COc1nc(N2CCCCCC2)c(Cl)nc1C(=O)N=C(N)N]

3-hydroxy-5-hexamethyleneimino-amiloride comprising the structure

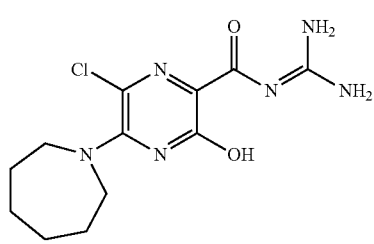 [SMILES: NC(N)=NC(=O)c1nc(Cl)c(N2CCCCCC2)nc1O]

Hexamethyleneimino-6-phenyl-2-pyraxinecarboxamide comprising the structure

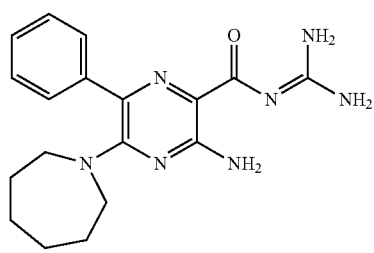 [SMILES: NC(N)=NC(=O)c1nc(-c2ccccc2)c(N2CCCCCC2)nc1N]

N-amidino-3,5-diamino-6-phenyl-2-pyrazinecarboxamide comprising the structure

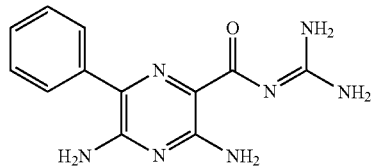 [SMILES: NC(N)=NC(=O)c1nc(-c2ccccc2)c(N)nc1N]

5-(N,N-hexamethylene)amiloride comprising the structure

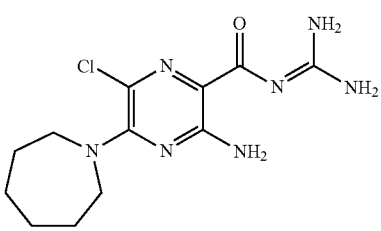 [SMILES: NC(N)=NC(=O)c1nc(Cl)c(N2CCCCCC2)nc1N]

N-amidino-3-amino-5-phenyl-6-chloro-2-pyrazinecarboxamide comprising the structure

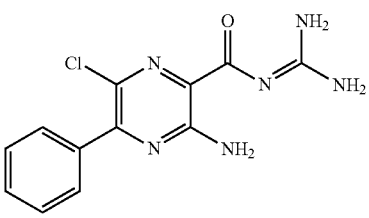 [SMILES: NC(N)=NC(=O)c1nc(Cl)c(-c2ccccc2)nc1N]

3'4 DichloroBenzamil comprising the structure

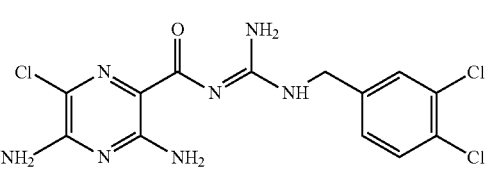 [SMILES: N/C(=N\C(=O)c1nc(Cl)c(N)nc1N)NCc1ccc(Cl)c(Cl)c1]

2'4 DichloroBenzamil HCl comprising the structure

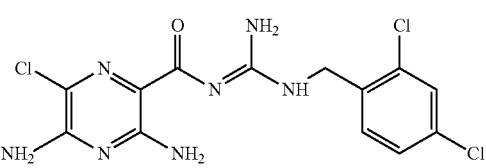 [SMILES: N/C(=N\C(=O)c1nc(Cl)c(N)nc1N)NCc1ccc(Cl)cc1Cl]

5-(N-methyl-N-guanidinocarbonyl-methyl)amiloride comprising the structure

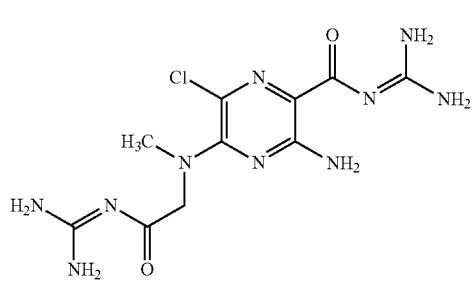 [SMILES: CN(CC(=O)N=C(N)N)c1nc(N)c(C(=O)N=C(N)N)nc1Cl]

5-(N,N-Diethyl)amiloride hydrochloride comprising the structure

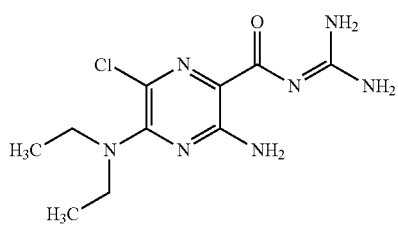 [SMILES: CCN(CC)c1nc(N)c(C(=O)N=C(N)N)nc1Cl]

5-(N,N-Dimethyl)amiloride hydrochloride comprising the structure

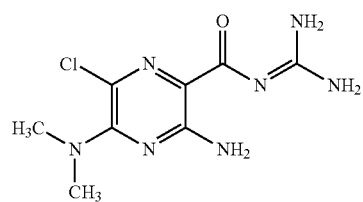 [SMILES: CN(C)c1nc(N)c(C(=O)N=C(N)N)nc1Cl]

5-tert-butylamino-amiloride comprising the structure

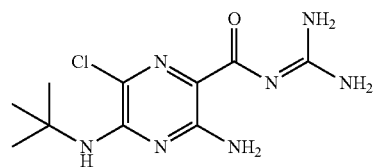 [SMILES: CC(C)(C)Nc1nc(N)c(C(=O)N=C(N)N)nc1Cl]

6-Iodoamiloride comprising the structure

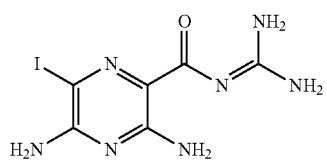 [SMILES: NC(N)=NC(=O)c1nc(I)c(N)nc1N]

Bodipy-FL Amiloride comprising the structure

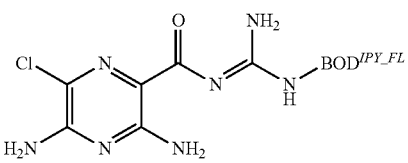

5-(4-fluorophenyl)amiloride comprising the structure

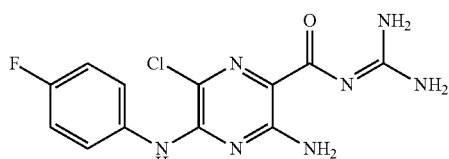

1-napthoylguanidine comprising the structure

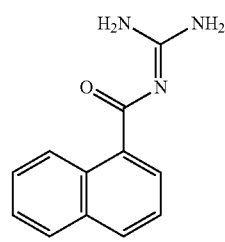 [SMILES: NC(N)=NC(=O)c1cccc2ccccc12]

2-napthoylguanidine comprising the structure

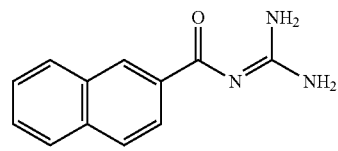 [SMILES: NC(N)=NC(=O)c1ccc2ccccc2c1]

N-(2-napthoyl)-N'-phenylguanidine comprising the structure

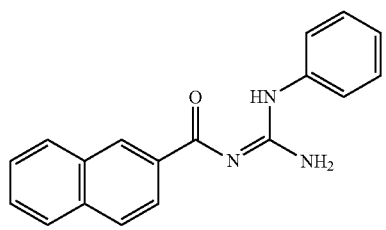 [SMILES: N/C(=N/C(=O)c1ccc2ccccc2c1)Nc1ccccc1]

N,N'-bis(2-napthoyl)guanidine comprising the structure

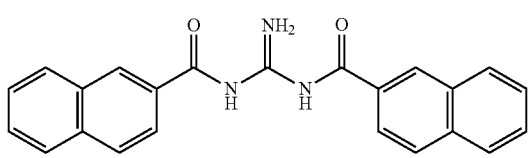 [SMILES: N=C(NC(=O)c1ccc2ccccc2c1)NC(=O)c1ccc2ccccc2c1]

N,N'-bis(1-napthoyl)guanidine comprising the structure

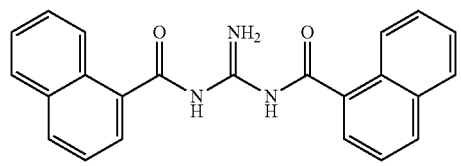 [SMILES: N=C(NC(=O)c1cccc2ccccc12)NC(=O)c1cccc2ccccc12]

N,N'-bis(2-napthoyl)-N''-phenylguanidine comprising the structure

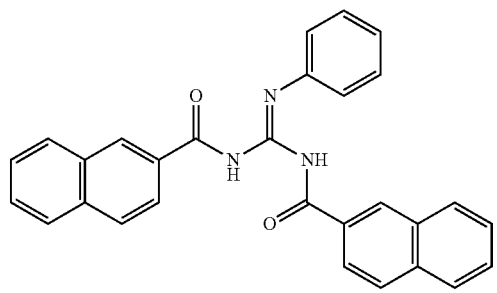 [SMILES: O=C(NC(=Nc1ccccc1)NC(=O)c1ccc2ccccc2c1)c1ccc2ccccc2c1]

6-methoxy-2-naphthoylguanidine comprising the structure

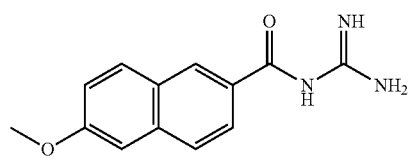 [SMILES: COc1ccc2cc(C(=O)NC(=N)N)ccc2c1]

N-Cinnamoyl-N',N'-dimethylguanidine comprising the structure

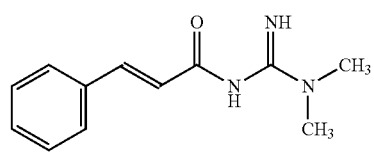 [SMILES: CN(C)C(=N)NC(=O)/C=C/c1ccccc1]

3-quinolinoylguanidine comprising the structure

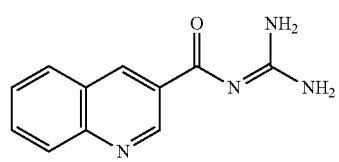 [SMILES: NC(N)=NC(=O)c1cnc2ccccc2c1]

cinnamoylguanidine comprising the structure

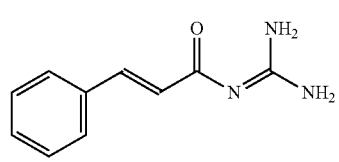 [SMILES: NC(N)=NC(=O)/C=C/c1ccccc1]

4-phenylbenzoylguanidine comprising the structure

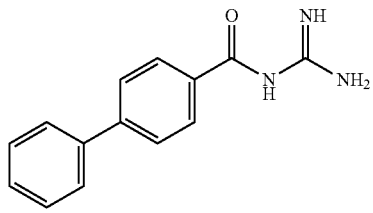 [SMILES: N=C(N)NC(=O)c1ccc(-c2ccccc2)cc1]

N-(cinnamoyl)-N'-phenylguanidine comprising the structure

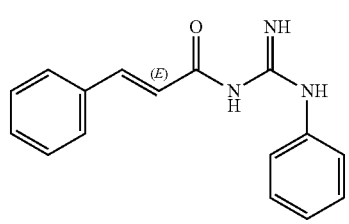 [SMILES: N=C(NC(=O)/C=C/c1ccccc1)Nc1ccccc1]

(3-phenylpropanoyl)guanidine comprising the structure

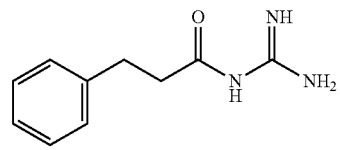 [SMILES: N=C(N)NC(=O)CCc1ccccc1]

N,N'-bis-(cinnamoyl)-N''-phenylguanidine comprising the structure

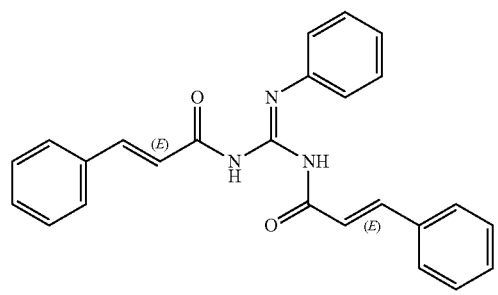 [SMILES: O=C(/C=C/c1ccccc1)NC(=Nc1ccccc1)NC(=O)/C=C/c1ccccc1]

N-(3-phenylpropanoyl)-N'-phenylguanidine comprising the structure

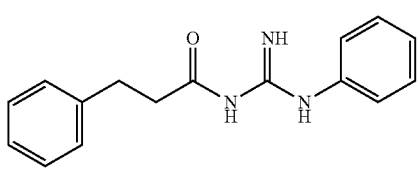 [SMILES: N=C(NC(=O)CCc1ccccc1)Nc1ccccc1]

N,N'-bis(3phenylpropanoyl)-N"-phenylguanidine comprising the structure

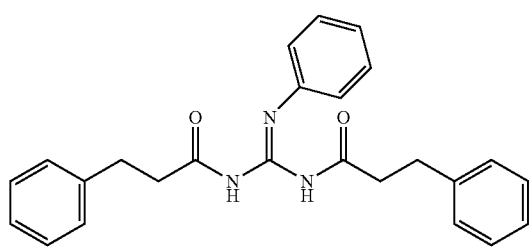 [SMILES: O=C(CCc1ccccc1)NC(=Nc1ccccc1)NC(=O)CCc1ccccc1]

trans-3-furanacryoylguanidine comprising the structure

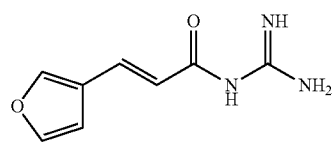 [SMILES: N=C(N)NC(=O)/C=C/c1ccoc1]

N-(6-Hydroxy-2-napthoyl)-N'-phenylguanidine comprising the structure

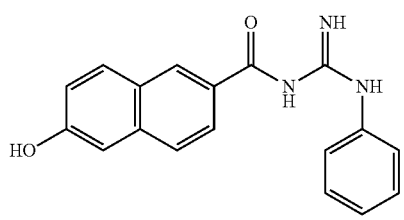 [SMILES: N=C(NC(=O)c1ccc2cc(O)ccc2c1)Nc1ccccc1]

(4-Phenoxybenzoyl)guanidine comprising the structure

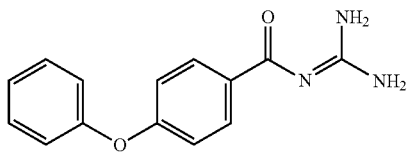 [SMILES: NC(N)=NC(=O)c1ccc(Oc2ccccc2)cc1]

N,N'-Bis(amidino)napthalene-2,6-dicarboxamide comprising the structure

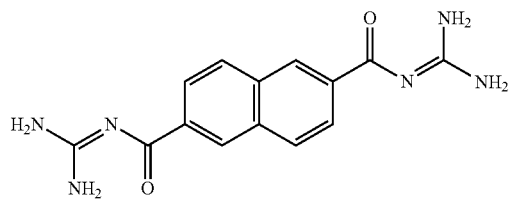 [SMILES: NC(N)=NC(=O)c1ccc2cc(C(=O)N=C(N)N)ccc2c1]

6-bromo-2-napthoylguanidine comprising the structure

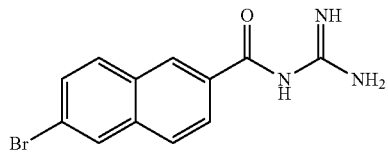 [SMILES: N=C(N)NC(=O)c1ccc2cc(Br)ccc2c1]

1-bromo-2-napthoylguanidine comprising the structure

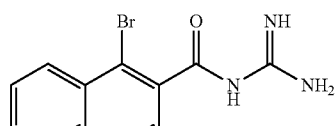

2-(2-napthyl)acetoylguanidine comprising the structure

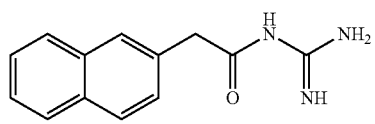 [SMILES: N=C(N)NC(=O)Cc1ccc2ccccc2c1]

N"-Cinnamoyl-N,N'-diphenylguanidine comprising the structure

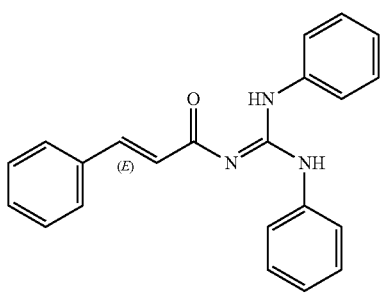 [SMILES: O=C(/C=C/c1ccccc1)N=C(Nc1ccccc1)Nc1ccccc1]

(Phenylacetyl)guanidine comprising the structure

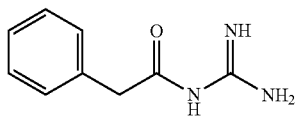 [SMILES: N=C(N)NC(=O)Cc1ccccc1]

N,N-Bis(3-phenylpropanoyl)guanidine comprising the structure

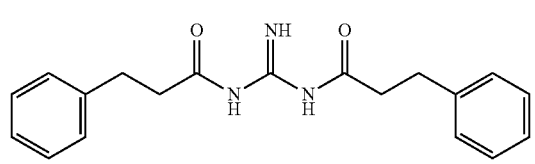 [SMILES: N=C(NC(=O)CCc1ccccc1)NC(=O)CCc1ccccc1]

Benzoylguanidine comprising the structure

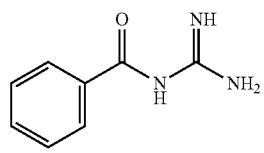 [SMILES: N=C(N)NC(=O)c1ccccc1]

(4-Chlorophenoxy-acetyl)guanidine comprising the structure

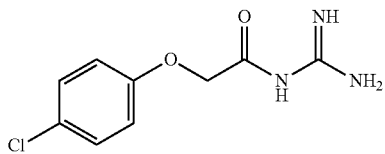 [SMILES: N=C(N)NC(=O)COc1ccc(Cl)cc1]

N-Benzoyl-N'-cinnamoylguanidine comprising the structure

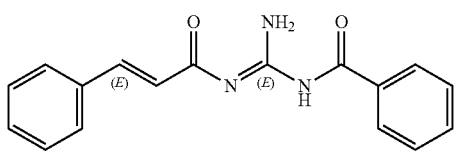 [SMILES: N/C(=N\C(=O)/C=C/c1ccccc1)NC(=O)c1ccccc1]

[(E)-3-(4-Dimethylaminophenyl)-2-methylacryloyl]guanidine comprising the structure

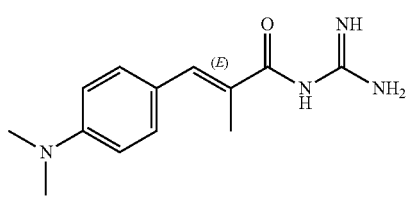 [SMILES: C/C(=C\c1ccc(N(C)C)cc1)C(=O)NC(=N)N]

(4-Chlorocinnamoyl)guanidine comprising the structure

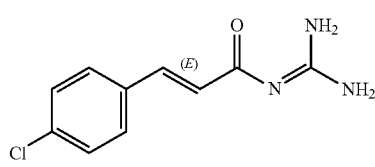 [SMILES: NC(N)=NC(=O)/C=C/c1ccc(Cl)cc1]

(4-Bromocinnamoyl)guanidine comprising the structure

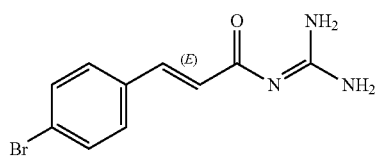 [SMILES: NC(N)=NC(=O)/C=C/c1ccc(Br)cc1]

(4-Methoxycinnamoyl)guanidine comprising the structure

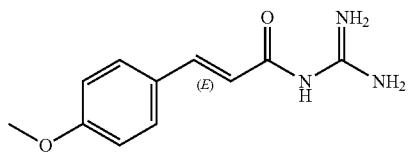 [SMILES: COc1ccc(/C=C/C(=O)NC(=N)N)cc1]

(5-Phenyl-penta-2,4-dienoyl)guanidine comprising the structure

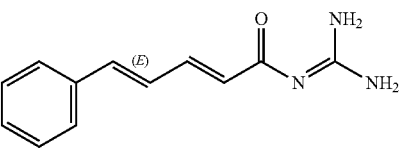 [SMILES: NC(N)=NC(=O)/C=C/C=C/c1ccccc1]

(3-Bromocinnamoyl)guanidine comprising the structure

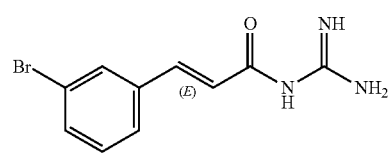 [SMILES: N=C(N)NC(=O)/C=C/c1cccc(Br)c1]

(3-Methoxycinnamoyl)guanidine comprising the structure

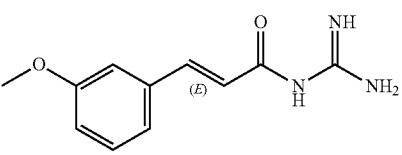 [SMILES: COc1cccc(/C=C/C(=O)NC(=N)N)c1]

(3-Chlorocinnamoyl)guanidine comprising the structure

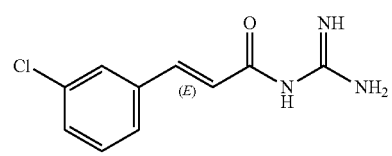

(2-Chlorocinnamoyl)guanidine comprising the structure

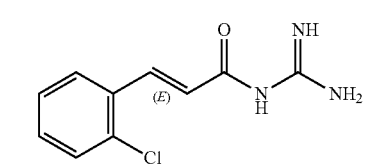 [SMILES: N=C(N)NC(=O)/C=C/c1ccccc1Cl]

(2-Bromocinnamoyl)guanidine comprising the structure

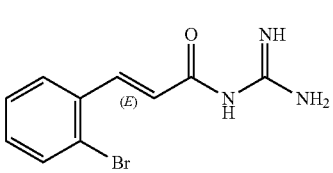 [SMILES: N=C(N)NC(=O)/C=C/c1ccccc1Br]

(2-Methoxycinnamoyl)guanidine comprising the structure

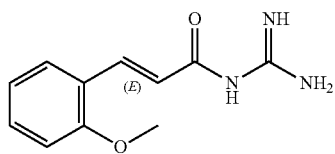 [SMILES: COc1ccccc1/C=C/C(=O)NC(=N)N]

(trans-2-Phenylcyclopropanecarbonyl)guanidine comprising the structure

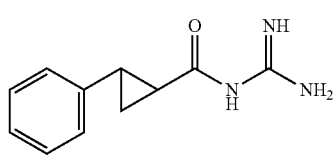 [SMILES: N=C(N)NC(=O)C1CC1c1ccccc1]

[3-(3-Pyridyl)acryloyl]guanidine comprising the structure

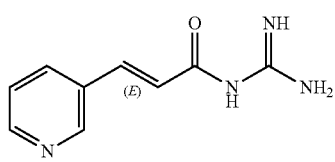 [SMILES: N=C(N)NC(=O)/C=C/c1cccnc1]

(4-Hydroxycinnamoyl)guanidine comprising the structure

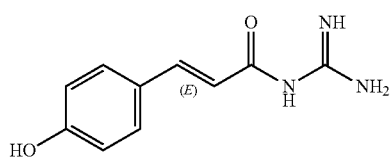 [SMILES: N=C(N)NC(=O)/C=C/c1ccc(O)cc1]

(Quinoline-2-carbonyl)guanidine comprising the structure

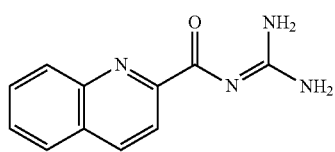 [SMILES: NC(N)=NC(=O)c1ccc2ccccc2n1]

(4-Nitrocinnamoyl)guanidine comprising the structure

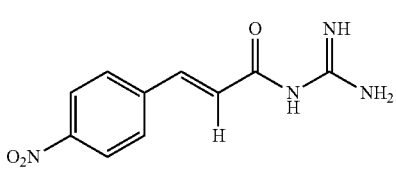

(3-Nitrocinnamoyl)guanidine comprising the structure

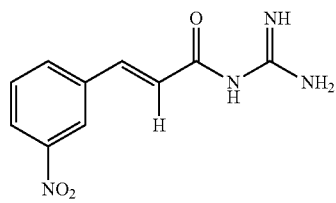 [SMILES: N=C(N)NC(=O)/C=C/c1cccc([N+](=O)[O-])c1]

(2-Nitrocinnamoyl)guanidine comprising the structure

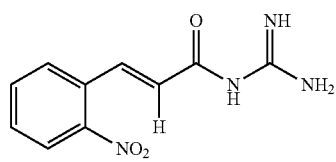 [SMILES: N=C(N)NC(=O)/C=C/c1ccccc1[N+](=O)[O-]]

(α-Methylcinnamoyl)guanidine comprising the structure

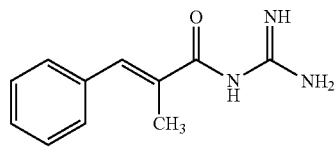

trans-3-(1-napthyl)acryloylguanidine comprising the structure

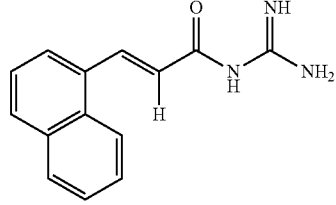 [SMILES: N=C(N)NC(=O)/C=C/c1cccc2ccccc12]

4-phenylcinnamoylguanidine comprising the structure

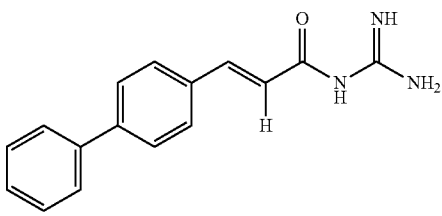 [SMILES: N=C(N)NC(=O)/C=C/c1ccc(-c2ccccc2)cc1]

3-(trifluoromethyl)cinnamoylguanidine comprising the structure

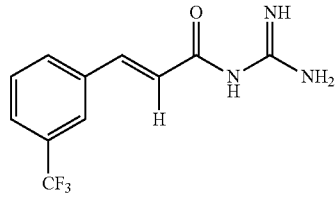 [SMILES: N=C(N)NC(=O)/C=C/c1cccc(C(F)(F)F)c1]

3-methylcinnamoylguanidine comprising the structure

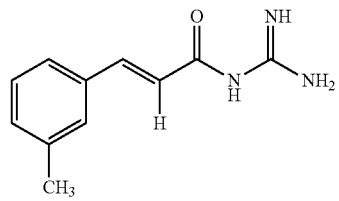

4-(trifluoromethyl)cinnamoylguanidine comprising the structure

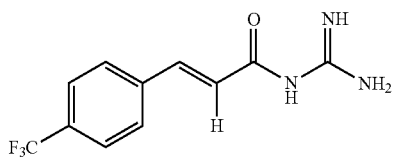 [SMILES: N=C(N)NC(=O)/C=C/c1ccc(C(F)(F)F)cc1]

2-methylcinnamoylguanidine comprising the structure

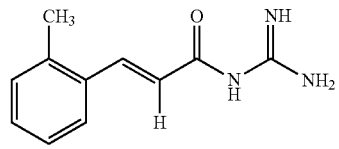

2-(trifluoromethyl)cinnamoylguanidine comprising the structure

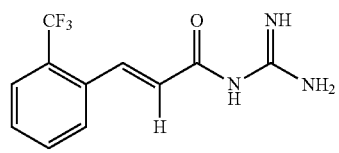 [SMILES: N=C(N)NC(=O)/C=C/c1ccccc1C(F)(F)F]

4-methylcinnamoylguanidine comprising the structure

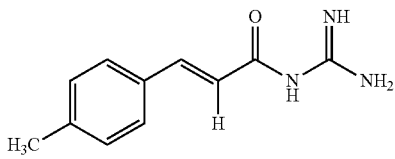

4-isopropylcinnamoylguanidine comprising the structure

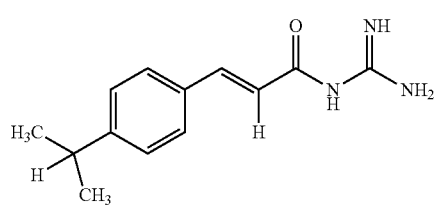 [SMILES: CC(C)c1ccc(/C=C/C(=O)NC(=N)N)cc1]

3-fluorocinnamoylguanidine comprising the structure

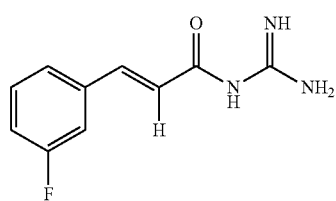 [SMILES: N=C(N)NC(=O)/C=C/c1cccc(F)c1]

2-fluorocinnamoylguanidine comprising the structure

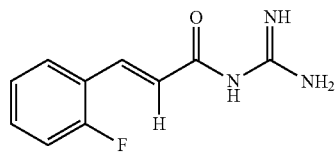 [SMILES: N=C(N)NC(=O)/C=C/c1ccccc1F]

4-fluorocinnamoylguanidine comprising the structure

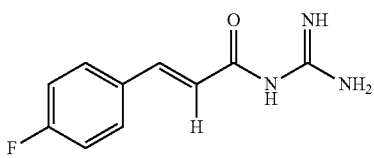 [SMILES: N=C(N)NC(=O)/C=C/c1ccc(F)cc1]

3,4-dichlorocinnamoylguanidine comprising the structure

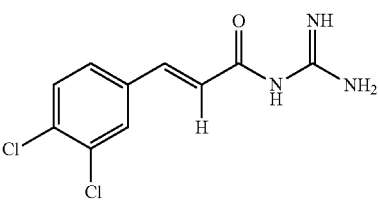 [SMILES: N=C(N)NC(=O)/C=C/c1ccc(Cl)c(Cl)c1]

2,4-dichlorocinnamolyguanidine comprising the structure

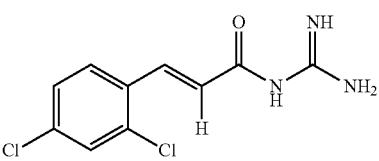 [SMILES: N=C(N)NC(=O)/C=C/c1ccc(Cl)cc1Cl]

2,6-dichlorocinnamoylguanidine comprising the structure

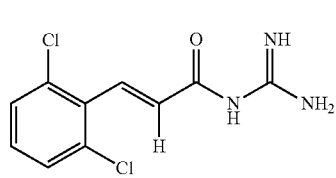

4-ethoxycinnamoylguanidine comprising the structure

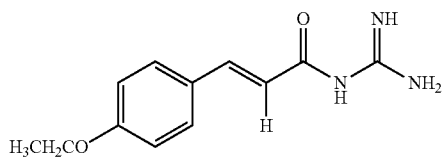

3,4-(methylenedioxy)cinnamoylguanidine comprising the structure

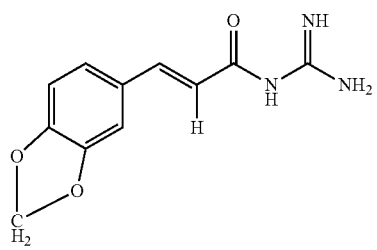 [SMILES: N=C(N)NC(=O)/C=C/c1ccc2c(c1)OCO2]

3-(2-napthyl)acryloylguanidine comprising the structure

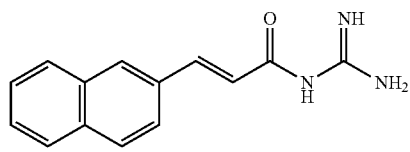 [SMILES: N=C(N)NC(=O)/C=C/c1ccc2ccccc2c1]

4-t-butylcinnamoylguanidine comprising the structure

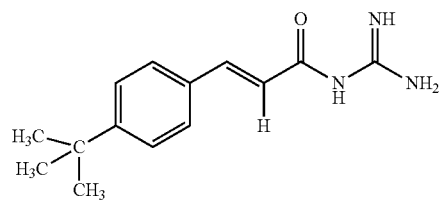 [SMILES: CC(C)(C)c1ccc(/C=C/C(=O)NC(=N)N)cc1]

3,4,5-trimethoxycinnamoylguanidine comprising the structure

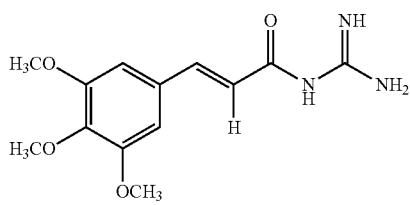 [SMILES: COc1cc(/C=C/C(=O)NC(=N)N)cc(OC)c1OC]

2-(1-napthyl)acetoylguanidine comprising the structure

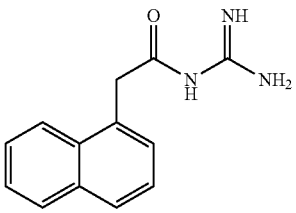 [SMILES: N=C(N)NC(=O)Cc1cccc2ccccc12]

2,5-dimethylcinnamoylguanidine comprising the structure

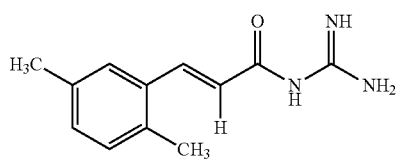 [SMILES: Cc1ccc(C)c(/C=C/C(=O)NC(=N)N)c1]

2,3-difluorocinnamoylguanidine comprising the structure

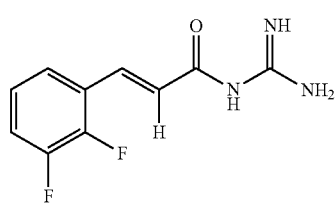 [SMILES: N=C(N)NC(=O)/C=C/c1cccc(F)c1F]

3-phenylcinnamoylguanidine comprising the structure

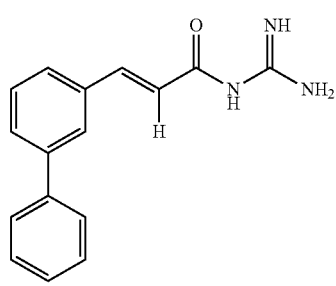 [SMILES: N=C(N)NC(=O)/C=C/c1cccc(-c2ccccc2)c1]

3-(trans-hept-1-en-1-yl)cinnamoylguanidine comprising the structure

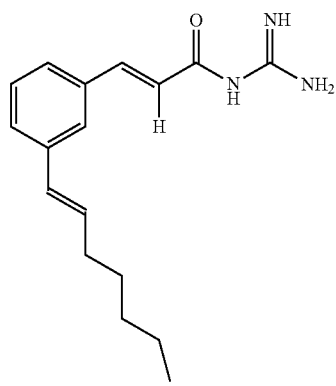 [SMILES: CCCCC/C=C/c1cccc(/C=C/C(=O)NC(=N)N)c1]

2-ethylcinnamoylguanidine comprising the structure

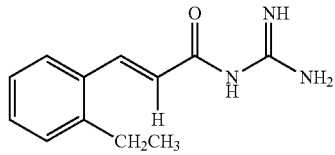 [SMILES: CCc1ccccc1/C=C/C(=O)NC(=N)N]

2-chloro-6-fluorocinnamoylguanidine comprising the structure

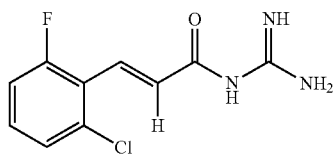 [SMILES: N=C(N)NC(=O)/C=C/c1c(F)cccc1Cl]

3-t-butylcinnamoylguanidine comprising the structure

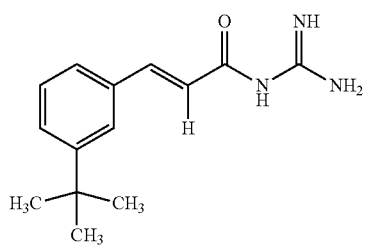 [SMILES: CC(C)(C)c1cccc(/C=C/C(=O)NC(=N)N)c1]

3,4-difluorocinnamoylguanidine comprising the structure

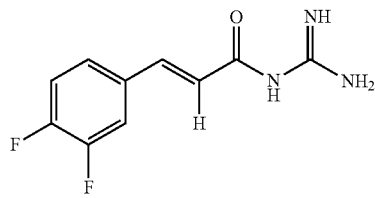 [SMILES: N=C(N)NC(=O)/C=C/c1ccc(F)c(F)c1]

5-bromo-2-fluorocinnamoylguanidine comprising the structure

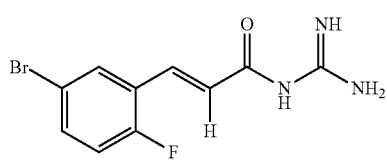 [SMILES: N=C(N)NC(=O)/C=C/c1cc(Br)ccc1F]

3-(trifluoromethoxy)cinnamoylguanidine comprising the structure

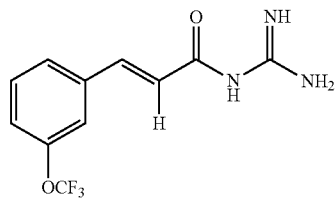 [SMILES: N=C(N)NC(=O)/C=C/c1cccc(OC(F)(F)F)c1]

2-ethoxycinnamoylguanidine comprising the structure

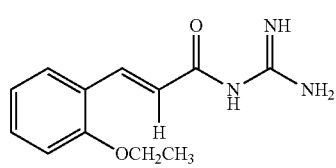 [SMILES: CCOc1ccccc1/C=C/C(=O)NC(=N)N]

2-t-butylcinnamoylguanidine comprising the structure

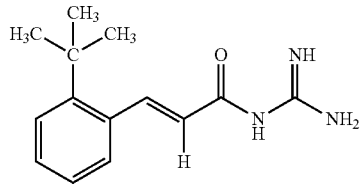 [SMILES: CC(C)(C)c1ccccc1/C=C/C(=O)NC(=N)N]

3-(cyclohex-1-en-1-yl)cinnamoylguanidine comprising the structure

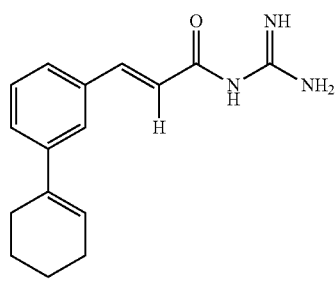 [SMILES: N=C(N)NC(=O)/C=C/c1cccc(C2=CCCCC2)c1]

cinnamoylguanidine hydrochloride comprising the structure

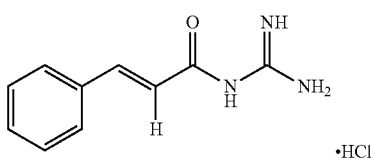 [SMILES: N=C(N)NC(=O)/C=C/c1ccccc1 ; Cl]

2,3,5,6,-tetramethylcinnamoylguanidine comprising the structure (Bit 134)

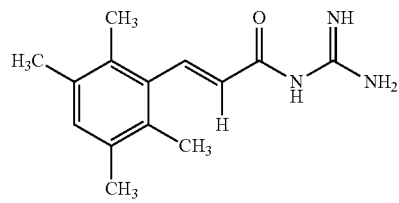 [SMILES: Cc1cc(C)c(C)c(/C=C/C(=O)NC(=N)N)c1C]

2-cyclohexylcinnamoylguanidine comprising the structure

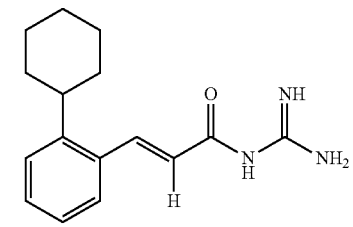 [SMILES: N=C(N)NC(=O)/C=C/c1ccccc1C1CCCCC1]

5-bromo-2-methoxycinnamoylguanidine comprising the structure

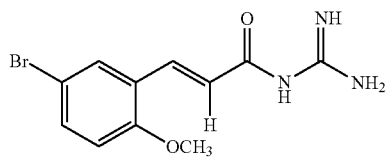

2,3-dimethylcinnamoylguanidine comprising the structure

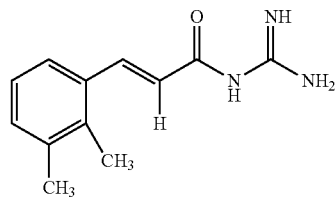 [SMILES: Cc1cccc(/C=C/C(=O)NC(=N)N)c1C]

3-ethoxycinnamoylguanidine comprising the structure

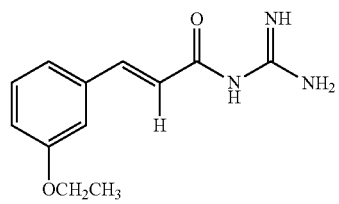

3-isopropylcinnamoylguanidine hydrochloride comprising the structure

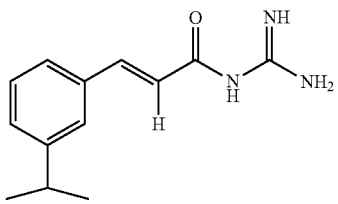

2-phenylcinnamoylguanidine comprising the structure

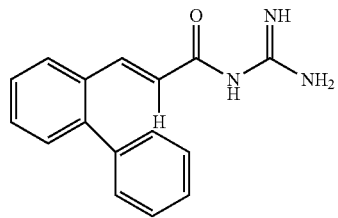 [SMILES: N=C(N)NC(=O)/C=C/c1ccccc1-c1ccccc1]

2-(cyclohex-1-en-1yl)cinnamoylguanidine comprising the structure

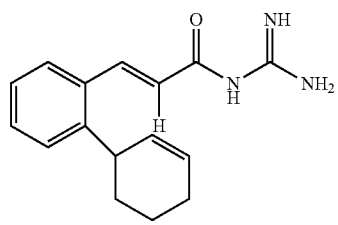 [SMILES: N=C(N)NC(=O)/C=C/c1ccccc1C1C=CCCC1]

2,4,6-trimethylcinnamoylguanidine comprising the structure

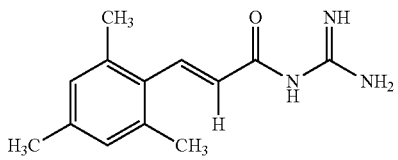 [SMILES: Cc1cc(C)c(/C=C/C(=O)NC(=N)N)c(C)c1]

(5-Phenyl-penta-2,4-dienoyl)guanidine comprising the structure

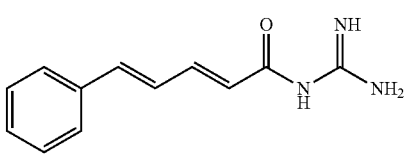 [SMILES: N=C(N)NC(=O)/C=C/C=C/c1ccccc1]

5-(3'-bromophenyl)penta-2,4-dienoylguanidine comprising the structure

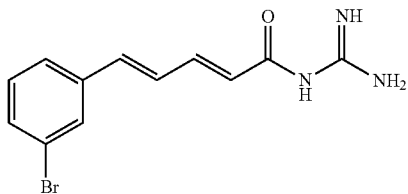 [SMILES: N=C(N)NC(=O)/C=C/C=C/c1cccc(Br)c1]

5-(2'-bromophenyl)penta-2,4-dienoylguanidine comprising the structure

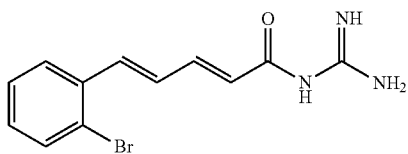 [SMILES: N=C(N)NC(=O)/C=C/C=C/c1ccccc1Br]

Furanacryloyl comprising the structure

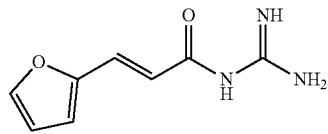 [SMILES: N=C(N)NC(=O)/C=C/c1ccco1]

Preferably, the compounds of the invention are capable of reducing, retarding or otherwise inhibiting viral growth and/or replication.

Preferably, the antiviral activity of the compounds of the invention is against viruses such as those belonging to the Lentivirus family, and the Coronovirus family family of viruses. For example, the compounds of the invention exhibit antiviral activity against viruses such as Human Immunodeficiency Virus (HIV), Severe Acute Respiratory Syndrome virus (SARS), Mouse Hepatitis virus ( ), and Hepatitis C virus (HCV).

According to a fourth aspect of the present invention, there is provided a pharmaceutical composition comprising an antiviral compound according to any one of the first, second or third aspects, and optionally one or more pharmaceutical acceptable carriers or derivatives, wherein said compound is capable of reducing, retarding or otherwise inhibiting viral growth and/or replication.

Preferably, the antiviral activity of the compounds of the invention is against viruses such as those belonging to the Lentivirus family, and the Coronovirus family of viruses. For example, the compounds of the invention exhibit antiviral activity against viruses such as Human Immunodeficiency Virus (HIV), Severe Acute Respiratory Syndrome virus (SARS), Human Coronavirus 229E, Human Coronavirus OC43, Mouse Hepatitis virus (MHV), Bovine Coronavirus (BCV), Porcine Respiratory Coronavirus (PRCV), Hepatitis C virus (HCV) and Equine Arteritis Virus (EAV).

Other Coronaviruses which can be inhibited or their infections treated by the compounds of the invention are those listed in Table 1.

The compositions of the invention may further comprise one or more known antiviral compounds or molecules.

According to a fifth aspect, there is provided a method for reducing, retarding or otherwise inhibiting growth and/or replication of a virus comprising contacting a cell infected with said virus or exposed to said virus with a compound according to any one of the first, second or third aspects.

Preferably, the virus is from the Lentivirus family, or the Coronavirus family. More preferably, the virus is Human Immunodeficiency Virus (HIV), Severe Respiratory Syndrome virus (SARS), Human Coronavirus 229E, Human Coronavirus OC43, Mouse Hepatitis virus (MHV), Bovine Coronavirus (BCV), Porcine Respiratory Coronavirus (PRCV), Mouse Hepatitis virus (MHV), Hepatitis C virus (HCV), or Equine Arteritis Virus (EAV). Most preferably, the virus is HIV-1, HIV-2, the SARS virus, Coronaviruse 229E, Coronavirus OC43, PRCV, BCV, HCV, or EAV.

Other Coronaviruses which can be inhibited or their infections treated by the compounds of the invention are those listed in Table 1.

According to a sixth aspect, there is provided a method for preventing the infection of a cell exposed to a virus comprising contacting said cell with a compound according to any one of the first, second or third aspects.

Preferably, the virus is from the Lentivirus family, or the Coronavirus family. More preferably, the virus is Human Immunodeficiency Virus (HIV), Severe Respiratory Syndrome virus (SARS), Human Coronavirus 229E, Human Coronavirus OC43, Mouse Hepatitis virus (MHV), Bovine Coronavirus (BCV), Porcine Respiratory Coronavirus (PRCV), Mouse Hepatitis virus (MHV), Hepatitis C virus (HCV), or Equine Arteritis Virus (EAV). Most preferably, the virus is HIV-1, HIV-2, the SARS virus, Coronaviruse 229E, Coronavirus OC43, PRCV, BCV, HCV, EAV.

Other Coronaviruses which can be inhibited or their infections treated by the compounds of the invention are those listed in Table 1.

According to a seventh aspect of the invention, there is provided a method for the therapeutic or prophylactic treatment of a subject infected with or exposed to a virus, comprising the administration of a compound according to any one of the first, second or third aspects, to a subject in need of said treatment.

Preferably, infection with a virus or exposure to a virus occurs with viruses belonging to the Lentivirus family, or the Coronavirus family. More preferably, infection or exposure occurs with HIV, SARS, Human Coronavirus 229E, Human Coronavirus OC43, Mouse Hepatitis virus (MHV), Bovine Coronavirus (BCV), Porcine Respiratory Coronavirus (PRCV), Hepatitis C virus (HCV), or Equine Arteritis Virus (EAV). Most preferably, infection or exposure occurs with HIV-1, HIV-2, SARS, Human Coronavirus 229E, Human Coronavirus OC43, Hepatitis C virus (HCV), or Equine Arteritis Virus (EAV).

Other Coronaviruses which can be inhibited or their infections treated by the compounds of the invention are those listed in Table 1.

The subject of the viral inhibition is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably, the subject is a primate, or horse. Most preferably, the subject is a human.

According to a eighth aspect, there is provided a method of down regulating a membrane ion channel functional activity in a cell infected with a virus, comprising contacting said cell with a compound according to any one of the first, second or third aspects.

The membrane ion channel may be endogenous to the cell or exogenous to the cell.

Preferably, the membrane ion channel of which functional activity is down regulated is that which Lentiviruses, and Coronaviruses utilise for mediating viral replication and include, for example, the HIV membrane ion channel Vpu, the HCV membrane ion channel P7, the Coronavirus E protein membrane ion channel, and the SARS E protein membrane ion channel.

Preferably, infection with a virus or exposure to a virus occurs with viruses belonging to the Lentivirus family, or the Coronovirus family. More preferably, infection or exposure occurs with HIV, SARS, Human Coronavirus 229E, Human Coronavirus OC43, Mouse Hepatitis virus (MHV), Bovine Coronavirus (BCV), Porcine Respiratory Coronavirus (PRCV), Hepatitis C virus (HCV), or Equine Arteritis Virus (EAV). Most preferably, infection or exposure occurs with HIV-1, HIV-2, SARS, Human Coronavirus 229E, Human Coronavirus OC43, Hepatitis C virus (HCV), or Equine Arteritis Virus (EAV).

According to an ninth aspect of the present invention, there is provided a method of reducing, retarding or otherwise inhibiting growth and/or replication of a virus that has infected a cell, said method comprising contacting said infected cell with a compound according to any one of the first, second or third aspects, wherein said compound down regulates functional activity of a membrane ion channel derived from said virus and expressed in said infected cell.

Preferably, infection occurs with a virus belonging to the Lentivirus family, or the Coronovirus family. More preferably, infection or exposure occurs with HIV, SARS, Human Coronavirus 229E, Human Coronavirus OC43, Mouse Hepatitis virus (MHV), Bovine Coronavirus (BCV), Porcine Respiratory Coronavirus (PRCV), Hepatitis C virus (HCV), or Equine Arteritis Virus (EAV). Most preferably, infection or exposure occurs with HIV-1, HIV-2, SARS, Human Coronavirus 229E, Human Coronavirus OC43, Hepatitis C virus (HCV), or Equine Arteritis Virus (EAV).

Other Coronaviruses which can be inhibited or their infections treated by the compounds of the invention are those listed in Table 1.

Preferably, the membrane ion channel of which functional activity is down regulated is that which Lentiviruses, and Coronaviruses utilise for mediating viral replication and include, for example, the HIV membrane ion channel Vpu, the HCV membrane ion channel P7, and the Coronavirus E protein membrane ion channel.

According to an tenth aspect, the present invention provides a method of reducing, retarding or otherwise inhibiting growth and/or replication of a virus that has infected a cell in a mammal, said method comprising administering to said mammal a compound according to any one of the first, second or third aspects, or a pharmaceutical composition according to the fourth aspect, wherein said compound or said composition down regulates functional activity of a membrane ion channel expressed in said infected cell.

Preferably, infection occurs with a virus belonging to the Lentivirus family, or the Coronovirus family. More preferably, infection or exposure occurs with HIV, SARS, Human Coronavirus 229E, Human Coronavirus OC43, Mouse Hepatitis virus (MHV), Bovine Coronavirus (BCV), Porcine Respiratory Coronavirus (PRCV), Hepatitis C virus (HCV), or Equine Arteritis Virus (EAV). Most preferably, infection or exposure occurs with HIV-1, HIV-2, SARS, Human Coronavirus 229E, Human Coronavirus OC43, Hepatitis C virus (HCV), or Equine Arteritis Virus (EAV).

Other Coronaviruses which can be inhibited or their infections treated by the compounds of the invention are those listed in Table 1.

Preferably, the membrane ion channel of which functional activity is down regulated is that which Lentiviruses, and Coronaviruses utilise for mediating viral replication and include, for example, the HIV membrane ion channel Vpu, the HCV membrane ion channel P7, and the Coronavirus E protein membrane ion channel.

The subject of the viral inhibition is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably, the subject is a primate, or horse. Most preferably, the subject is a human.

According to a eleventh aspect, the present invention provides a method for the therapeutic or prophylactic treatment of a subject infected with or exposed to a virus comprising administering to said subject a compound according to any one of the first, second or third aspects, or a pharmaceutical composition according to the fourth aspect, wherein said compound or said composition down-regulates functional activity of a membrane ion channel derived from said virus.

Preferably, infection occurs with a virus belonging to the Lentivirus family, or the Coronovirus family of viruses. More preferably, infection or exposure occurs with HIV, SARS, Human Coronavirus 229E, Human Coronavirus OC43, Mouse Hepatitis virus (MHV), Bovine Coronavirus (BCV), Porcine Respiratory Coronavirus (PRCV), Hepatitis C virus (HCV), or Equine Arteritis Virus (EAV). Most preferably, infection or exposure occurs with HIV-1, HIV-2, SARS, Human Coronavirus 229E, Human Coronavirus OC43, Hepatitis C virus (HCV), or Equine Arteritis Virus (EAV).

Other Coronaviruses which can be inhibited or their infections treated by the compounds of the invention are those listed in Table 1.

Preferably, the membrane ion channel of which functional activity is down regulated is that which Lentiviruses, and Coronaviruses utilise for mediating viral replication and include, for example, the HIV membrane ion channel Vpu, the HCV membrane ion channel P7, and the Coronavirus E protein membrane ion channel.

The subject of the viral inhibition is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably, the subject is a primate, or horse. Most preferably, the subject is a human.

According to a twelfth aspect, the invention provides an antiviral compound selected from the group consisting of:
- N-(3,5-Diamino-6-chloro-pyrazine-2-carbonyl)-N'-phenyl-guanidine,
- N-Benzyl-N'-(3,5-diamino-6-chloro-pyrazine-2-carbonyl)-guanidine,
- 3'4 DichloroBenzamil,
- 2'4 DichloroBenzamil,
- 5-(N-methyl-N-guanidinocarbonyl-methyl)amiloride,
- 5-(N-Methyl-N-isobutyl)amiloride,
- 5-(N-Ethyl-N-isopropyl)amiloride,
- 5-(N,N-Dimethyl)amiloride hydrochloride,
- 5-(N,N-hexamethylene)amiloride,
- 5-(N,N-Diethyl)amiloride hydrochloride,
- 6-Iodoamiloride, Bodipy-FL amiloride,
3-hydroxy-5-hexamethyleneimino-amiloride,
5-(4-fluorophenyl)amiloride,
5-tert-butylamino-amiloride,
N-amidino-3-amino-5-phenyl-6-chloro-2-pyrazinecarboxamide,
3-methoxy-5-(N,N-Hexamethylene)-amiloride,
3-methoxy-amiloride,
hexamethyleneimino-6-phenyl-2-pyrazinecarboximide,
N-amidino-3,5-diamino-6-phenyl-2-pyrazinecarboxamide,
1-naphthoylguanidine,
2-naphthoylguanidine,
N-(2-naphthoyl)-N'-phenyl-guanidine,
N,N'-bis(2-naphthoyl)guanidine,
N,N'-bis(1-naphthoyl)guanidine,
N,N'-bis(2-naphthoyl)-N''-phenyl-guanidine,
6-methoxy-2-naphthoylguanidine,
3-quinolinoylguanidine,
cinnamoylguanidine,
4-phenylbenzoylguanidine,
N-(cinnamoyl)-N'-phenyl-guanidine,
(3-phenylpropanoyl)guanidine,
N,N'-bis-(cinnamoyl)-N''-phenyl-guanidine,
N-(3-phenylpropanoyl)-N'-phenyl-guanidine,
N,N'-bis(3phenylpropanoyl)-N''-phenyl-guanidine,
trans-3-furanacryoylguanidine,
N-(6-Hydroxy-2-naphthoyl)-N'-phenyl-guanidine,
(4-Phenoxybenzoyl)guanidine,
N,N'-Bis(amidino)napthalene-2,6-dicarboxamide,
N''-Cinnamoyl-N,N'-diphenylguanidine,
(Phenylacetyl)guanidine,
N,N'-Bis(3-phenylpropanoyl)guanidine,
benzoylguanidine,
(4-Chlorophenoxy-acetyl)guanidine,
N-benzoyl-N'-cinnamoylguanidine,
[(E)-3-(4-Dimethylaminophenyl)-2-methylacryloyl]guanidine,
(4-Chlorocinnamoyl)guanidine,
(4-Bromocinnamoyl)guanidine,
(4-Methoxycinnamoyl)guanidine,
(5-Phenyl-penta-2,4-dienoyl)guanidine,
(3-Bromocinnamoyl)guanidine,
(3-Methoxycinnamoyl)guanidine,
(3-Chlorocinnamoyl)guanidine,
(2-Chlorocinnamoyl)guanidine,
(2-Bromocinnamoyl)guanidine,
(2-Methoxycinnamoyl)guanidine,
(trans-2-Phenylcyclopropanecarbonyl)guanidine,
[3-(3-Pyridyl)acryloyl]guanidine,
(4-Hydroxycinnamoyl)guanidine,
(Quinoline-2-carbonyl)guanidine,
or pharmaceutically acceptable salts thereof.

According to a thirteenth aspect, the present invention provides a pharmaceutical composition comprising a compound according to the twelfth aspect, and optionally one or more pharmaceutical acceptable carriers or derivatives.

Preferably, the pharmaceutical composition may further comprise one or more known antiviral compounds or molecules.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

BRIEF DESCRIPTION OF THE DRAWINGS

FIG. 1A-1C is a schematic representation of plasmids used for expression of Vpu in E. coli. 1A. The amino acid sequence (<400>1) (SEQ ID NO: 1) encoded by the vpu open reading frame (ORF) generated by PCR from an HIV-1 strain HXB2 oDNA clone. The vpu ORF was cloned in-frame at the 3' end of the GST gene in p2GBX to generate p2GEXVpu (1B). It was subsequently cloned into pPL451 to produce the plasmid pPL+Vpu (1C).

DETAILED DESCRIPTION OF THE INVENTION

Figure 1B:
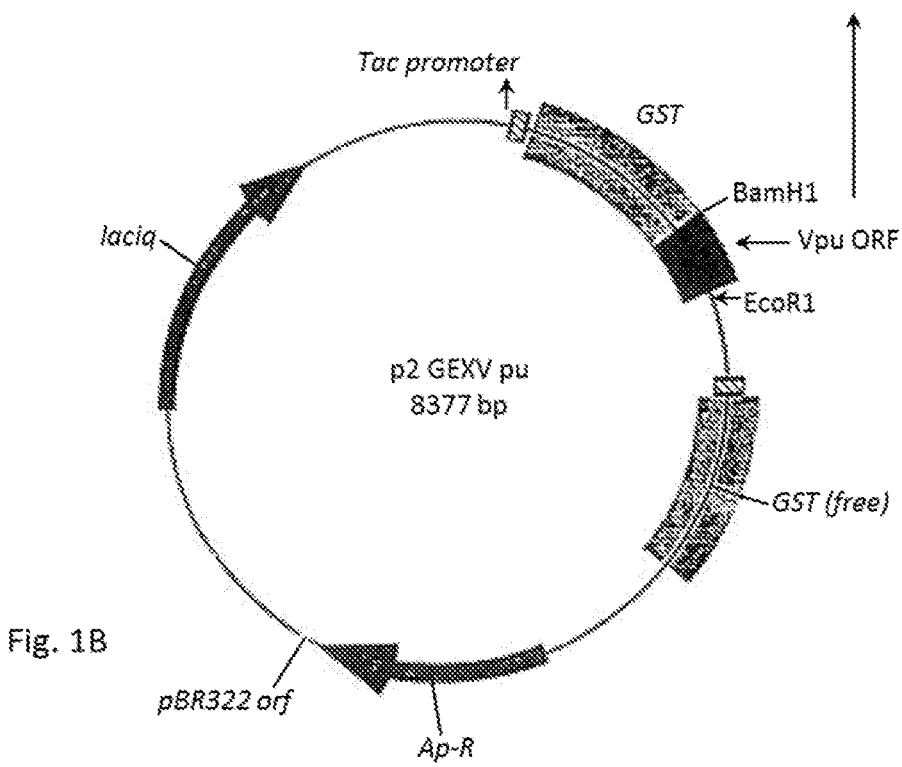

The present invention is based, in part, on the surprising determination that certain compounds that fall under the classification of substituted acylguanidines have antiviral activity against viruses from a range of different virus families. Without intending to be bound by any particular theory or mechanism of action, the negative impact of the compounds of the present invention on viral replication may be mediated by the inhibition or otherwise down-regulation of a membrane ion channel relied upon by the virus for replication. This membrane ion channel may be a viral membrane ion channel (exogenous to the host cell) or a host cell ion channel induced as a result of viral infection (endogenous to the host cell).

As an example, the compounds of the present invention may inhibit Vpu or p7 function and thereby inhibit the continuation of the respective HIV or HCV life cycle.

The SARS virus encodes an E protein which is shown for the first time, by the present inventors, to act as an ion channel. As similar E proteins are present in other coronaviruses, the compounds, compositions and methods of the present invention would have utility in the inhibition and/or treatment of infections by other coronaviruses.

While the present invention is concerned with novel antiviral compounds falling under the classification of substituted acylguanidines, it does not include in its scope the use of compounds 5-(N,N-hexamethylene)amiloride and 5-(N,N-dimethyl)-amiloride for retarding, reducing or otherwise inhibiting viral growth and/or functional activity of HIV.

It will be understood by those skilled in the art that the compounds of the invention may be administered in the form of a composition or formulation comprising pharmaceutically acceptable carriers and excipients.

The pharmaceutical compositions of the invention may further comprise one or more known antiviral compounds or molecules. Preferably, the known anti-viral compounds are selected from the group consisting of Vidarabine, Acyclovir, Ganciclovir, Valganciclovir, Valacyclovir, Cidofovir, Famciclovir, Ribavirin, Amantadine, Rimantadine, Interferon, Oseltamivir, Palivizumab, Rimantadine, Zanamivir, nucleoside-analog reverse transcriptase inhibitors (NRTI) such as Zidovudine, Didanosine, Zalcitabine, Stavudine, Lamivudine and Abacavir, non-nucleoside reverse transcriptase inhibitors (NNRTI) such as Nevirapine, Delavirdine and Efavirenz, protease inhibitors such as Saquinavir, Ritonavir, Indinavir, Nelfinavir, Amprenavir, and other known antiviral compounds and preparations. Known anti-viral compounds or molecules may in some cases act synergistically with the anti-viral compounds of the invention.

TABLE 1

Known coronavirus isolates

Group 1 species
  Canine coronavirus
    Canine enteric coronavirus (strain INSAVC-1)
    Canine enteric coronavirus (strain K378)
  Feline coronavirus
    Feline enteric coronavirus (strain 79-1683)
    Feline infectious peritonitis virus (FIPV)
  Human coronavirus 229E
  Porcine epidemic diarrhea virus
    Porcine epidemic diarrhea virus (strain Br1/87)
    Porcine epidemic diarrhea virus (strain CV777)
  Transmissible gastroenteritis virus
    Porcine respiratory coronavirus
    Porcine transmissible gastroenteritis coronavirus (STRAIN FS772/70)
    Porcine transmissible gastroenteritis coronavirus (strain Miller)
    Porcine transmissible gastroenteritis coronavirus (strain Neb72-RT)
    Porcine transmissible gastroenteritis coronavirus (STRAIN PURDUE)
Group 2 species
  Bovine coronavirus
    Bovine coronavirus (STRAIN F15)
    Bovine coronavirus (strain G95)
    Bovine coronavirus (STRAIN L9)
    Bovine coronavirus (strain LSU-94LSS-051)
    Bovine coronavirus (STRAIN LY-138)
    Bovine coronavirus (STRAIN MEBUS)
    Bovine coronavirus (strain OK-0514-3)
    Bovine coronavirus (strain Ontario)
    Bovine coronavirus (STRAIN QUEBEC)
    Bovine coronavirus (STRAIN VACCINE)
    Bovine enteric coronavirus (strain 98TXSF-110-ENT)
  Canine respiratory coronavirus
  Chicken enteric coronavirus
  Human coronavirus OC43
  Murine hepatitis virus
    Murine coronavirus (strain DVIM)
    Murine hepatitis virus (strain A59)
    Murine hepatitis virus (strain JHM)

TABLE 1-continued

Known coronavirus isolates

Murine hepatitis virus (strain S)
Murine hepatitis virus strain 1
Murine hepatitis virus strain 2
Murine hepatitis virus strain 3
Murine hepatitis virus strain 4
Murine hepatitis virus strain ML-11
Porcine hemagglutinating encephalomyelitis virus
    Porcine hemagglutinating encephalomyelitis virus (strain 67N)
    Porcine hemagglutinating encephalomyelitis virus (strain IAF-404)
Puffinosis virus
Rat coronavirus
    Rat coronavirus (strain 681)
    Rat coronavirus (strain NJ)
    Rat sialodacryoadenitis coronavirus
Group 3 species
  Turkey coronavirus
    Turkey coronavirus (strain Indiana)
    Turkey coronavirus (strain Minnesota)
    Turkey coronavirus (strain NC95)
  Avian infectious bronchitis virus
    Avian infectious bronchitis virus (STRAIN 6/82)
    Avian infectious bronchitis virus (strain Arkansas 99)
    Avian infectious bronchitis virus (strain Beaudette CK)
    Avian infectious bronchitis virus (strain Beaudette M42)
    Avian infectious bronchitis virus (strain Beaudette US)
    Avian infectious bronchitis virus (strain Beaudette)
    Avian infectious bronchitis virus (strain D1466)
    Avian infectious bronchitis virus (strain D274)
    Avian infectious bronchitis virus (strain D3896)
    Avian infectious bronchitis virus (strain D41)
    Avian infectious bronchitis virus (strain DE072)
    Avian infectious bronchitis virus (strain GRAY)
    Avian infectious bronchitis virus (strain H120)
    Avian infectious bronchitis virus (strain H52)
    Avian infectious bronchitis virus (strain KB8523)
    Avian infectious bronchitis virus (strain M41)
    Avian infectious bronchitis virus (strain PORTUGAL/322/82)
    Avian infectious bronchitis virus (strain SAIB20)
    Avian infectious bronchitis virus (strain UK/123/82)
    Avian infectious bronchitis virus (strain UK/142/86)
    Avian infectious bronchitis virus (strain UK/167/84)
    Avian infectious bronchitis virus (strain UK/183/66)
    Avian infectious bronchitis virus (strain UK/68/84)
    Avian infectious bronchitis virus (strain V18/91)
    Avian infectious bronchitis virus (strain Vic S)
  Avian infectious laryngotracheitis virus
Preliminary Group 4 species
  SARS coronavirus
    SARS coronavirus Beijing ZY-2003
    SARS coronavirus BJ01
    SARS coronavirus BJ02
    SARS coronavirus BJ03
    SARS coronavirus BJ04
    SARS coronavirus CUHK-Su10
    SARS coronavirus CUHK-W1
    SARS coronavirus Frankfurt 1
    SARS coronavirus GZ01
    SARS coronavirus HKU-39849
    SARS coronavirus Hong Kong ZY-2003
    SARS coronavirus Hong Kong/03/2003
    SARS coronavirus HSR 1
    SARS coronavirus Sin2500
    SARS coronavirus Sin2677
    SARS coronavirus Sin2679
    SARS coronavirus Sin2748
    SARS coronavirus Sin2774
    SARS coronavirus Taiwan
    SARS coronavirus Taiwan JC-2003
    SARS coronavirus Taiwan TC1
    SARS coronavirus Taiwan TC2
    SARS coronavirus Tor2
    SARS coronavirus TW1
    SARS coronavirus TWC
    SARS coronavirus Urbani
    SARS coronavirus Vietnam
    SARS coronavirus ZJ-HZ01
    SARS coronavirus ZJ01

TABLE 1-continued

Known coronavirus isolates unclassified coronaviruses
  Bovine respiratory coronavirus (strain 98TXSF-110-LUN)
  Human enteric coronavirus 4408
  Enteric coronavirus
  Equine coronavirus
    Equine coronavirus NC99

The present observations and findings now permit the use of agents such as certain substituted acylguanidines, as anti-viral agents for the therapy and prophylaxis of viral conditions caused by different viruses. The methods and compositions of the present invention may be particularly effective against viruses which rely on ion channel formation for their replication, however it will be understood that this is not the only mechanism relied on by viruses for replication and that the compounds and methods of the present invention are not limited to agents which exert their action by retarding or inhibiting the function of ion channels.

Reference to "membrane ion channel" should be understood as a reference to a structure which transports ions across a membrane. The present invention extends to ion channels which may function by means such as passive, osmotic, active or exchange transport. The ion channel may be formed by intracellular or extracellular means. For example, the ion channel may be an ion channel which is naturally formed by a cell to facilitate its normal functioning. Alternatively, the ion channel may be formed by extracellular means. Extracellular means would include, for example, the formation of ion channels due to introduced chemicals, drugs or other agents such as ionophores or due to the functional activity of viral proteins encoded by a virus which has entered a cell.

The ion channels which are the subject of certain embodiments of the present invention facilitate the transport of ions across membranes. Said membrane may be any membrane and is not limited to the outer cell wall plasma membrane. Accordingly, "membrane" as used herein encompasses the membrane surrounding any cellular organelle, such as the Golgi apparatus and endoplasmic reticulum, the outer cell membrane, the membrane surrounding any foreign antigen which is located within the cell (for example, a viral envelope) or the membrane of a foreign organism which is located extracellularly. The membrane is typically, but not necessarily, composed of a fluid lipid bilayer. The subject ion channel may be of any structure. For example, the Vpu ion channel is formed by Vpu which is an integral membrane protein encoded by HIV-1 which associates with, for example, the Golgi and endoplasmic reticulum membranes of infected cells. Reference hereinafter to "Vpu ion channels" is a reference to all related ion channels for example P7 HCV and M2 of influenza and the like.

Reference to "HIV", "SARS", "Coronavirus" or "HCV" should be understood as a reference to any HIV, SARS, Coronavirus or HCV virus strain and including homologues and mutants.

Reference to the "functional activity" of an ion channel should be understood as a reference to any one or more of the functions which an ion channel performs or is involved in. For example, the Vpu protein encoded ion channel, in addition to facilitating the transportation of $Na^+$, $K^+$, $Cl^-$ and $P0_4^{3-}$, also plays a role in the degradation of the CD4 molecule in the endoplasmic reticulum. Without wishing to be bound by a particular theory, the Vpu protein encoded ion channel is also thought to play a role in mediating the HIV life cycle. The present invention is not limited to treating HIV infection via the mechanism of inhibiting the HIV life cycle and, in particular, HIV replication. Rather, the present invention should be understood to encompass any mechanism by which the compounds of the present invention exert their anti-viral activity and may include inhibition of HIV viability or functional activity. This also applies to HCV, Coronaviruses, and to other viruses.

Reference to the "functional activity" of a virus should be understood as a reference to any one or more of the functions which a virus performs or is involved in.

Reference to the "viral replication" should be understood to include any one or more stages or aspects of the viral life cycle, such as inhibiting the assembly or release of virions. Ion channel mediation of viral replication may be by direct or indirect means. Said ion channel mediation is by direct means if the ion channel interacts directly with the virion at any one or more of its life cycle stages. Said ion channel mediation is indirect if it interacts with a molecule other than those of the virion, which other molecule either directly or indirectly modulates any one or more aspects or stages of the viral life cycle. Accordingly, the method of the present invention encompasses the mediation of viral replication via the induction of a cascade of steps which lead to the mediation of any one or more aspects or stages of the viral life cycle.

Reference to "down-regulating" ion channel functional activity, should be understood as a reference to the partial or complete inhibition of any one or more aspects of said activity by both direct and indirect mechanisms. For example, a suitable agent may interact directly with an ion channel to prevent replication of a virus or, alternatively, may act indirectly to prevent said replication by, for example, interacting with a molecule other than an ion channel. A further alternative is that said other molecule interacts with and inhibits the activity of the ion channel.

Screening for molecules that have antiviral activity can be achieved by the range of methodologies described herein.

Reference to a "cell" infected with a virus should be understood as a reference to any cell, prokaryotic or eukaryotic, which has been infected with a virus. This includes, for example, immortal or primary cell lines, bacterial cultures and cells in situ. In a suitable screening system for antiviral compounds, the preferred infected cells would be macrophages/monocytes or hepatocytes/lymphoid cells infected with either HIV or HCV respectively.

Without limiting the present invention to any one theory or mode of action, the compounds of the present invention are thought to inhibit viral replication or virion release from cells by causing ion channels, namely VPU of HIV, the E protein of SARS and other Coronaviruses, or P7 of HCV to become blocked. The present invention encompasses antiviral compounds that are substituted acylguanidines.

The present invention also includes the use of compounds 5-(N,N-hexamethylene)amiloride and 5-(N,N-dimethyl)-amiloride in the control of viral replication and/or growth other than HIV.

The subject of the viral inhibition is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably, the subject is a human or primate. Most preferably, the subject is a human.

The method of the present invention is useful in the treatment and prophylaxis of viral infection such as, for example, but not limited to HIV infection, HCV infection and other viral infections. For example, the antiviral activity may be effected in subjects known to be infected with HIV in order to prevent replication of HIV thereby preventing the onset of AIDS. Alternatively, the method of the present invention may be used to reduce serum viral load or to alleviate viral infection symptoms. Similarly, antiviral treatment may be effected in subjects known to be infected with, for example, HCV, in order to prevent replication of HCV, thereby preventing the further hepatocyte involvement and the ultimate degeneration of liver tissue.

The method of the present invention may be particularly useful either in the early stages of viral infection to prevent the establishment of a viral reservoir in affected cells or as a prophylactic treatment to be applied immediately prior to or for a period after exposure to a possible source of virus.

Reference herein to "therapeutic" and "prophylactic" is to be considered in their broadest contexts. The term "therapeutic" does not necessarily imply that a mammal is treated until total recovery. Similarly, "prophylactic" does not necessarily mean that the subject will not eventually contract a disease condition. Accordingly, therapy and prophylaxis include amelioration of the symptoms of a particular condition or preventing or otherwise reducing the risk of developing a particular condition. The term "prophylaxis" may be considered as reducing the severity of onset of a particular condition. Therapy may also reduce the severity of an existing condition or the frequency of acute attacks.

In accordance with the methods of the present invention, more than one compound or composition may be co-administered with one or more other compounds, such as known anti-viral compounds or molecules. By "co-administered" is meant simultaneous administration in the same formulation or in two different formulations via the same or different routes or sequential administration by the same or different routes. By "sequential" administration is meant a time difference of from seconds, minutes, hours or days between the administration of the two or more separate compounds. The subject antiviral compounds may be administered in any order.

Routes of administration include but are not limited to intravenously, intraperitionealy, subcutaneously, intracranialy, intradermally, intramuscularly, intraocularly, intrathecaly, intracerebrally, intranasally, transmucosally, by infusion, orally, rectally, via iv drip, patch and implant. Intravenous routes are particularly preferred.

Compositions suitable for injectable use include sterile aqueous solutions (where water soluble) and sterile powders for the extemporaneous preparation of sterile injectable solutions. The carrier can be a solvent or dispersion medium containing, for example, water, ethanol, polyol (for example, glycerol, propylene glycol and liquid polyethylene glycol, and the like), suitable mixtures thereof and vegetable oils. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by, for example, filter sterilization or sterilization by other appropriate means. Dispersions are also contemplated and these may be prepared by incorporating the various sterilized active ingredients into a sterile vehicle which contains the basic dispersion medium and the required other ingredients from those enumerated above. In the case of sterile powders for the preparation of sterile injectable solutions, a preferred method of preparation includes vacuum drying and the freeze-drying technique which yield a powder of the active ingredient plus any additional desired ingredient from a previously sterile-filtered solution.

When the active ingredients are suitably protected, they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.01% by weight, more preferably 0.1% by weight, even more preferably 1% by weight of active compound. The percentage of the compositions and preparations may, of course, be varied and may conveniently be between about 1 to about 99%, more preferably about 2 to about 90%, even more preferably about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ng and 2000 mg of active compound.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels. In such forms, the anti-clotting peptides may need to be modified to permit penetration of the surface barrier. Procedures for the preparation of dosage unit forms and topical preparations are readily available to those skilled in the art from texts such as *Pharmaceutical Handbook. A Martindale Companion Volume* Ed. Ainley Wade Nineteenth Edition The Pharmaceutical Press London, *CRC Handbook of Chemistry and Physics* Ed. Robert C. Weast Ph D. CRC Press Inc.; *Goodman and Gilman's; The Pharmacological basis of Therapeutics*. Ninth Ed. McGraw Hill; *Remington; and The Science and Practice of Pharmacy*. Nineteenth Ed. Ed. Alfonso R. Gennaro Mack Publishing Co. Easton Pa.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding.

Effective amounts contemplated by the present invention will vary depending on the severity of the pain and the health and age of the recipient. In general terms, effective amounts may vary from 0.01 ng/kg body weight to about 100 mg/kg body weight.

Alternative amounts include for about 0.1 ng/kg body weight about 100 mg/kg body weight or from 1.0 ng/kg body weight to about 80 mg/kg body weight.

The subject of the viral inhibition is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably, the subject is a human or primate. Most preferably, the subject is a human.

The methods of the present invention is useful in the treatment and prophylaxis of viral infection such as, for example, but not limited to HIV infection, HCV infection and other viral infections. For example, the antiviral activity may be effected in subjects known to be infected with HIV in order to prevent replication of HIV thereby preventing the onset of AIDS. Alternatively, the methods of the present invention may be used to reduce serum viral load or to alleviate viral infection symptoms. Similarly, antiviral treatment may be effected in subjects known to be infected with, for example, HCV, in order to prevent replication of HCV, thereby preventing the further hepatocyte involvement and the ultimate degeneration of liver tissue.

The methods of the present invention may be particularly useful either in the early stages of viral infection to prevent the establishment of a viral reservoir in affected cells or as a prophylactic treatment to be applied immediately prior to or for a period after exposure to a possible source of virus.

The present invention will now be described in more detail with reference to specific but non-limiting examples describing studies of viral membrane ion channels and screening for antiviral activity. Some examples involve the use of the SARS virus. It will be clear from the description herein that other lentiviruses, and coronaviruses and other compounds may be used effectively in the context of the present invention. It is to be understood, however, that the detailed description is included solely for the purpose of exemplifying the present invention. It should not be understood in any way as a restriction on the broad description of the invention as set out above.

EXAMPLE 1

Synthesis of the Compounds of the Invention

The compounds of the present invention may be made from the corresponding acid chlorides or methyl esters as shown in Scheme 1. Both of these methods are well described in the literature.

Scheme 1

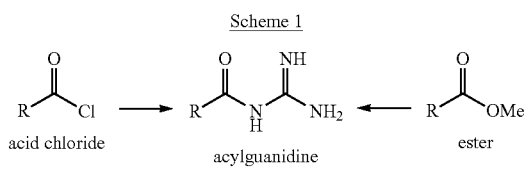

The following examples show synthetic schemes for some compounds of the invention.

EXAMPLE 2

Synthesis of Cinnamoylguanidine from Cinnamic Acid Cinnamoyl Chloride

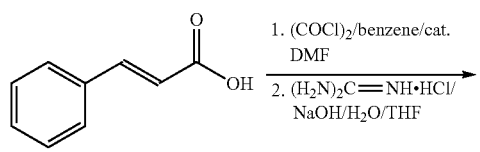

To a solution of trans-cinnamic acid (1.50 g, 10.12 mmol) in dry benzene (30 mL) containing a drop of N,N-dimethylformamide was added oxalyl chloride (5.14 g, 40.5 mmol) causing the solution to effervesce. After refluxing for 2 h, the solution was evaporated to dryness under reduced pressure. The resulting solid was dissolved in dry tetrahydrofuran (20 mL) and added slowly to a solution of guanidine hydrochloride in 2M aqueous sodium hydroxide (25 mL). The reaction was stirred at room temperature for 1 h then extracted with ethyl acetate (3×50 mL). The combined extracts were dried over magnesium sulfate and evaporated to give an orange oil. The crude product was purified by column chromatography. Elution with 10% to 20% methanol in dichloromethane gave Cinnamoylguanidine as a cream solid (0.829 g, 43%).

EXAMPLE 3

Synthesis of N-amidino-3-amino-5-phenyl-6-chloro-2-pyrazinecarboxamide

Part 1

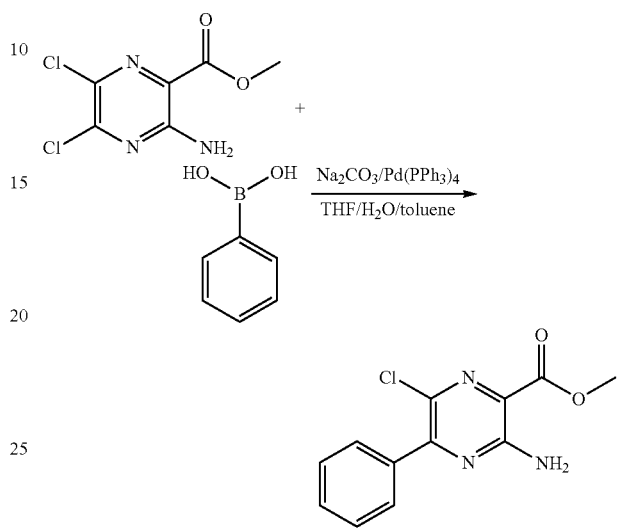

To a solution of methyl 3-amino-5,6-dichloro-2-pyrazinecarboxylate (0.444 g, 2.0 mmol) in tetrahydrofuran (5 mL)/water (10 mL)/toluene (20 mL) was added phenyl boronic acid (0.536 g, 4.4 mmol), sodium carbonate (0.699 g, 6.6 mmol) and tetrakis(triphenylphosphine)-palladium(0) (0.116 g, 0.10 mmol). The reaction was evacuated and purged with nitrogen several times before being refluxed for 6 h. The organic layer was separated and the aqueous layer extracted with toluene (3×20 mL).

The combined organic extracts were dried over magnesium sulfate, filtered and evaporated under reduced pressure to give methyl 3-amino-6-chloro-5-phenyl-2-pyrazinecarboxylate as a yellow solid (0.43 g, 82%).

Part 2

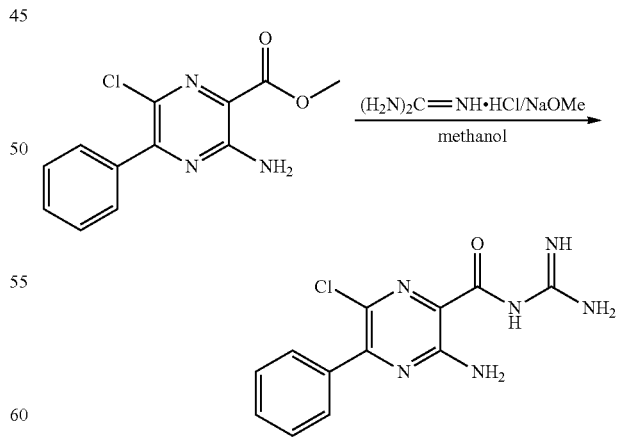

To a solution of sodium (0.040 g, 1.74 mmol) dissolved in methanol (5 mL) was added guanidine hydrochloride (0.258 g, 2.70 mmol) and the mixture refluxed for 30 min after which it was filtered. To the filtrate was added methyl 3-amino-6-chloro-5-phenyl-2-pyrazinecarboxylate (0.264 g, 1.0 mmol) in N,N-dimethylformamide (5 mL) and the solution heated at 75.0 for 12 h. The solvent was removed under reduced pressure and the residue chromatographed on silica gel eluting with 1% triethylamine/5% methanol/dichloromethane. The resulting solid was suspended in chloroform, filtered and dried under high vacuum to give N-Amidino-3-amino-5-phenyl-6-chloro-2-pyrazinecarboxamide as a yellow solid (0.04 g, 14%).

EXAMPLE 4

Synthesis of hexamethyleneimino-6-phenyl-2-pyrazinecarboxamide

Part 1

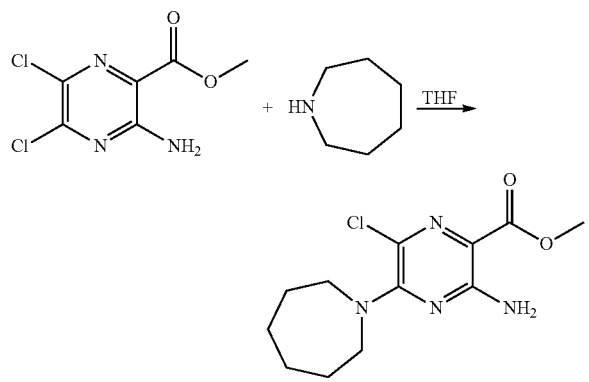

To a solution of methyl 3-amino-5,6-dichloro-2-pyrazinecarboxylate (1.11 g, 5.0 mmol) in tetrahydrofuran (50 mL) was added hexamethyleneimine (1.49 g, 15.0 mmol) and the reaction was refluxed for 1 h. The reaction was allowed to cool and the solid hexamethyleneimine hydrochloride removed by filtration. The filtrate was evaporated and the residue chromatographed over silica gel. Elution with dichloromethane gave methyl 3-amino-6-chloro-5-hexamethyleneimino-2-pyrazinecarboxylate as an off-white solid (1.20 g, 85%).

Part 2

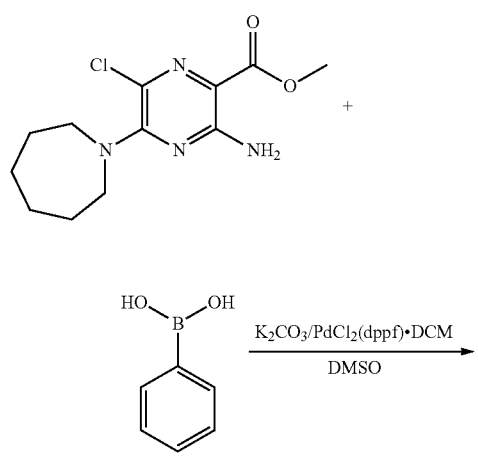

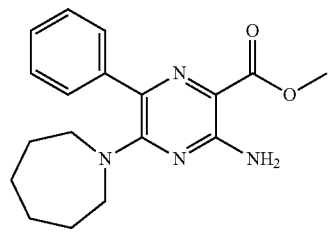

To a solution of methyl 3-amino-6-chloro-5-hexamethyleneimino-2-pyrazinecarboxylate (0.350 g, 1.23 mmol) in dimethylsulfoxide (5 mL) was added phenyl boronic acid (0.166 g, 1.35 mmol), potassium carbonate (0.511 g, 3.70 mmol) and [1,1'-bis(diphenylphosphino)ferrocene]dichloropalladium(II)-dichloromethane complex (0.041 g, 0.05 mmol). The reaction was heated at 90° C. for 16 h before being poured into water (50 mL) and extracted with ethyl acetate (3×50 mL). The combined extracts were dried over magnesium sulfate, filtered and evaporated to give a brown oil which was purified by chromatography on silica gel. Elution with dichloromethane followed by 10% ethyl acetate/dichloromethane gave methyl 3-amino-5-hexamethyleneimino-6-phenyl-2-pyrazinecarboxylate as a yellow solid (0.309 g, 77%).

Part 3.

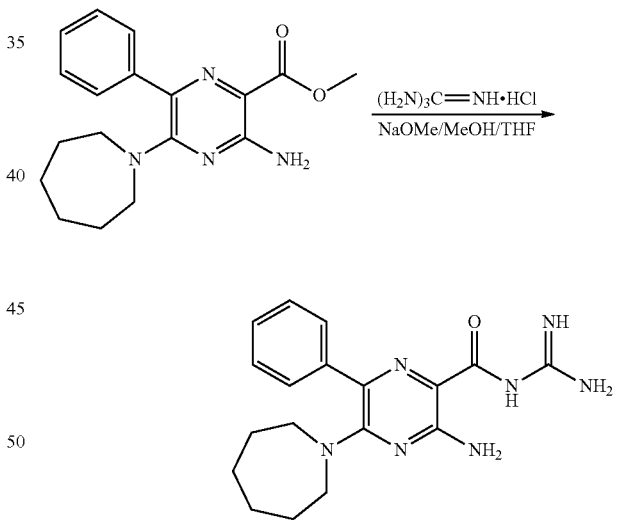

To a solution of sodium (0.090 g, 6.17 mmol) dissolved in methanol (8 mL) was added guanidine hydrochloride (0.598 g, 6.26 mmol) and the mixture was refluxed for 30 min after which it was filtered. To the filtrate was added methyl 3-amino-5-hexamethyleneimino-6-phenyl-2-pyrazinecarboxylate (0.310 g, 0.95 mmol) in tetrahydrofuran (10 mL) and the solution refluxed for 72 h. The solvent was removed under reduced pressure and the residue chromatographed on silica gel. Elution with 5% methanol/dichloromethane gave N-amidino-3-amino-5-hexamethyleneimino-6-phenyl-2-pyrazinecarboxamide as a yellow solid (0.116 g, 35%).

EXAMPLE 5

Viral Studies

Construction of Recombinant Plasmids Containing Open Reading Frames Encoding Various Virus Proteins.

Complimentary DNA (cDNA) fragments for the various viral proteins listed in Table 2 were obtained either by PCR amplification from a parental virus genome clone, or by direct chemical synthesis of the polynucleotide sequence. For example, the open reading frame encoding Vpu (FIG. 1a) was amplified by PCR from a cDNA clone of an Nde I fragment of the HIV-1 genome (isolate HXB2, McFarlane Burnet Centre, Melbourne, Australia) as follows: Native Pfu DNA polymerase (Stratagene; 0.035 U///Il) was chosen to catalyse the PCR reaction to minimise possible PCR introduced errors by virtue of the enzyme's proofreading activity. The 5', sense, primer AGTAGGATCCATGCAACCTATACC (<400>2) (SEQ ID NO: 2) introduces a BamH1 site (underlined) for cloning in-frame with the 3' end of the GST gene in p2GEX (41). This primer also repairs the start codon (bold T replaces a Q of the vpu gene which is a threonine codon in the HXB2 isolate. The 3', antisense, primer TCTGGAATTCTACAGATCATCAAC (<400>3) (SEQ ID NO: 3) introduces an EcoR1 site (underlined) to the other end of the PCR product to facilitate cloning. After 30 cycles of 94° C. for 45 sec, 55° C. for 1 min and 72° C. for 1 min in 0.5 ml thin-walled eppendorf tubes in a Perkin-Elmer thermocycler, the 268 bp fragment was purified, digested with BamH1 and EcoR1 and ligated to p2GEX prepared by digestion with the same two enzymes. The resultant recombinant plasmid is illustrated in FIG. 1b. The entireVpu open reading frame and the BamH1 and EcoR1 ligation sites were sequenced by cycle sequencing, using the Applied Biosystems dye-terminator kit, to confirm the DNA sequence. Other cDNAs were synthesised for us using state of the art methods by GenScript Corporation (New Jersey, USA). Codon sequences were optimised for expression in bacterial, insect or mammalian cells, as appropriate. Restriction endonuclease enzyme recognition sites were incorporated at the 5' and 3' ends of the synthetic cDNAs to facilitate cloning into plasmid expression vectors, pcDNA3.1, pFastBac and pPL451 for expression of the encoded virus proteins in mammalian, insect or bacterial cells, respectively.

Figure 1C:
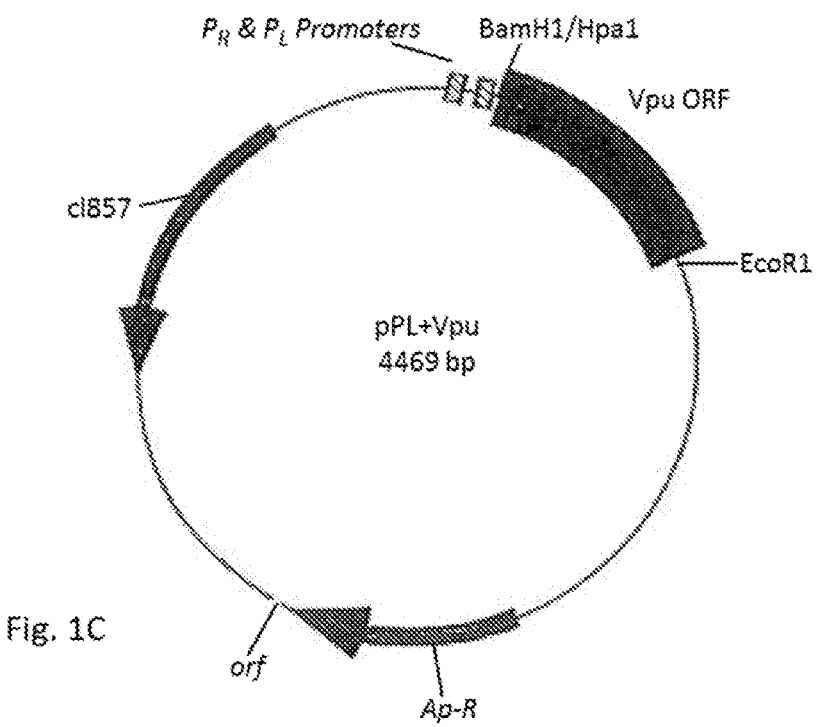

Standard techniques of molecular biology were used in cloning experiments. For example, to prepare the Vpu open reading frame for insertion into the pPL451 expression plasmid, p2GEXVpu was first digested with BamHI and the 5' base overhang was filled in the Klenow DNA polymerase in the presence of dNTPs. The Vpu-encoding fragment was then liberated by digestion with EcoR1, purified from an agarose gel and ligated into pPL451 which had been digested with HpaI and EcoR1. Western blots subsequently confirmed that the pPLVpu construct (FIG. 1c) expressed Vpu after induction of cultures at 42° C. to inactivate the cI857 repressor of the PR and PL promoters.

TABLE 2

Source of viral cDNA or peptide sequences.

| Target Protein | Source organism | Strain or Sequence Accession number |
|---|---|---|
| Vpu | HIV-1 | strain HXB2 |
| SARS-CoV E protein | SARS coronavirus | P59637 |
| HCV p7 | Hepatitis C virus H77 1a | NP_751922 |
| MHV-E protein | Murine hepatitis virus | NP_068673 |
| 229E E protein | Human coronavirus 229E | NP_073554 |
| Dengue M protein | Dengue virus type 1 | Strain Singapore S275/90 |

EXAMPLE 6

Purification of Recombinant Vpu from E. Coli

Cultures of E. coli strain XLI-blue cells containing p2GEXVpu were grown at 30° C. with vigorous aeration in LB medium supplemented with glucose (6 g/L) and ampicillin (50 mg/L) to a density of approximately 250 Klett units, at which time IPTG was added to a final concentration of 0.01 mM and growth was continued for a further 4 hr. The final culture density was approximately 280 Klett units. Since early experiments revealed that the majority of expressed GST-Vpu fusion protein was associated with both the cell debris and 30 membrane fractions, the method of Varadhachary and Maloney (Varadhachary and Maloney, 1990) was adopted to isolate osmotically disrupted cell ghosts (combining both cell debris and membrane fractions) for the initial purification steps. Cells were harvested, washed, weighed and resuspended to 10 ml/g wet weight in MTPBS containing DTT (ImM) and $MgCl_2$ (10 mM). Lysozyme (0.3 mg/ml; chicken egg white; Sigma) was added and incubated on ice for 30 min with gentle agitation followed by 5 min at 37° C. The osmotically sensitised cells were pelleted at 12,000 g and resuspended to the original volume in water to burst the cells. The suspension was then made up to 1×MTPBS/DTT using a 10× buffer stock and the ghosts were isolated by centrifugation and resuspended in MTPBS/DTT to which was then sequentially added glycerol (to 20% wt/vol) and CHAPS (to 2% wt/vol) to give a final volume of one quarter the original volume. This mixture was stirred on ice for 1 hr and then centrifuged at 400,000 g for 1 hr to remove insoluble material. The GST-Vpu fusion protein was purified from the detergent extract by affinity chromatography on a glutathione agarose resin (Sigma). The resin was thoroughly washed in 50 mM Tris pH 7.5 containing glycerol (5%), DTT (1 mM), and CHAPS (0.5%) (Buffer A) and then the Vpu portion of the fusion protein was liberated and eluted from the resin-bound GST by treatment of a 50% (v/v) suspension of the beads with human thrombin (100 U/ml; 37° C. for 1 hr). PMSF (0.5 mM) was added to the eluant to eliminate any remaining thrombin activity. This Vpu fraction was further purified on a column of MA7Q anion exchange resin attached to a BioRad HPLC and eluted with a linear NaCl gradient (0-2M) in buffer A.

The Vpu was purified to homogeneity—as determined on silver stained gels—on an immunoaffinity column as follows: HPLC fractions containing Vpu were desalted on a NAP 25 column (Pharmacia) into buffer A and then mixed with the antibody-agarose beads for 1 hr at room temperature. The beads were washed thoroughly and Vpu was eluted by increasing the salt concentration to 2M. Protein was quantitated using the BioRad dye binding assay.

EXAMPLE 7

Expression and Purification of Vpu in E. Coli

The plasmid p2GEXVpu (FIG. 1) was constructed to create an in-frame gene fusion between the GST and Vpu open-reading frames. This system enabled IPTG-inducible expression of the Vpu polypeptide fused to the C-terminus of GST and allowed purification of the fusion protein by affinity chromatography on glutathione agarose.

Figure 2A:
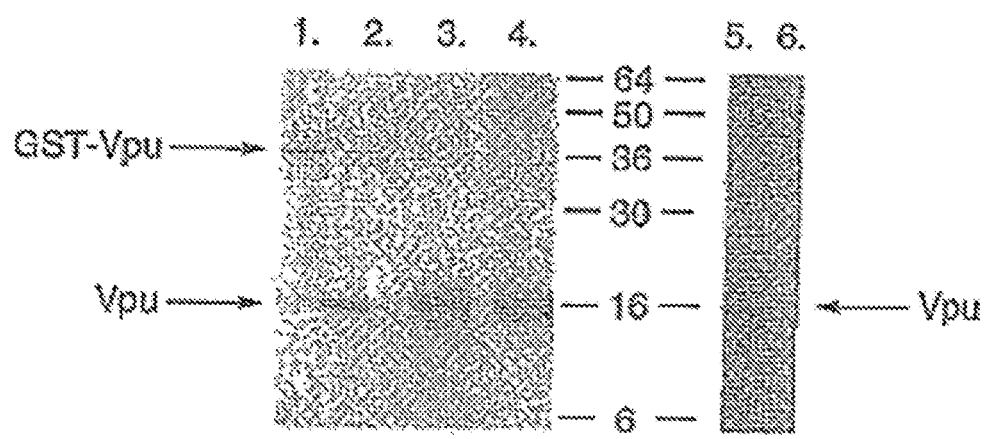
FIG. 2A-2B is a photographic representation of the expression and purification of Vpu in E. coli. 2A. Western blotting after SDS-PAGE was used to detect expressed Vpu in E. coli extracts. Lanes 1-4 contain samples, at various stages of purity, of Vpu expressed from p2GEXVpu: lane 1, GST-Vpu flasiors protein isolated by glutathione-agarose affinity chromatography; lane 2, Vpu liberated from the fusion protein by treatment with thrombin; lane 35 Vpu purified by HPLC anion exchange chromatography; lane 4, Vpu after passage through the immunoaffinity column. Lanes 5 and 6, membrane vesicles prepared from 42'C induced cells containing pPL+Vpu or pPL451, respectively. 2B. Silver stained SDS-PAGE gel: lane 1, Vpu purified by HPLC anion exchange chromatography; lane 2, Vpu after passage through the immunoaffinity column.
Figure 2B:
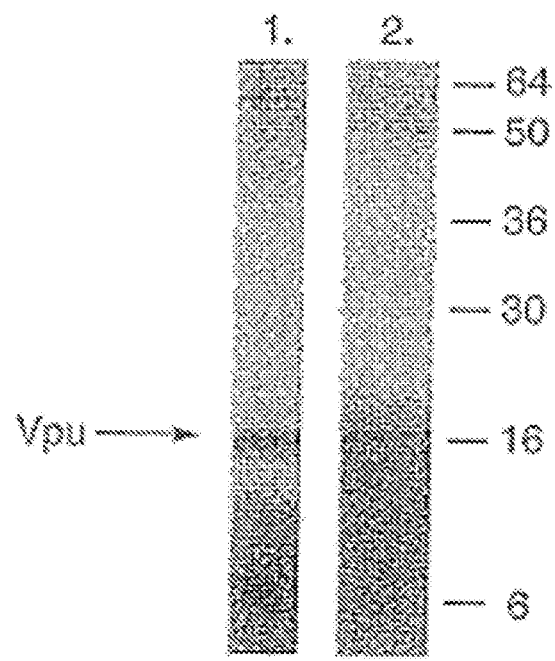

Optimal levels of GST-Vpu expression were obtained by growing the cultures at 30° C. to a cell density of approximately 250-300 Klett units and inducing with low levels of IPTG (0.01 mM). To purify the GST-Vpu, a combined cellular fraction containing the cell debris and plasma membrane was prepared by lysozyme treatment of the induced cells followed by a low-speed centrifugation. Approximately 50% of the GST-Vpu protein could be solubilised from this fraction using the zwitterionic detergent CHAPS. Affinity chromatography using glutathione-agarose beads was used to enrich the fusion protein and thrombin was used to cleave the fusion protein at the high affinity thrombin site between the fusion partners, liberating Vpu (FIG. 2A). In fractions eluted from the anion exchange column Vpu was the major protein visible on silver stained gels (FIG. 2B, lane 1). Finally, Vpu was purified to apparent homogeneity on an immunoaffinity column (FIG. 2B, lane 2). The N-terminal amino acid sequence of the protein band (excised from SDS-PAGE gels) corresponding to the immunodetected protein confirmed its identity as Vpu.

EXAMPLE 8

Reconstitution of Vpu in Phospholipid Vesicles

Proteoliposomes containing Vpu were prepared by the detergent dilution method (New, 1990). A mixture of lipids (PE:PC:PS; 5:3:2; 1 mg total lipid) dissolved in chloroform was dried under a stream of nitrogen gas and resuspended in 0.1 ml of potassium phosphate buffer (50 mM pH 7.4) containing DTT (ImM). A 25 µl aliquot containing purified Vpu was added, followed by octylglucoside to a final concentration of 1.25% (wt/vol). This mixture was subject to three rounds of freezing in liquid nitrogen, thawing and sonication in a bath type sonicator (20-30 sec) and was then rapidly diluted into 200 volumes of the potassium phosphate buffer. Proteoliposomes were collected by centrifugation at 400,000 g for 1 hr and resuspended in approximately 150 µl of phosphate buffer.

EXAMPLE 9

Assaying Vpu Ion Channel Activity

Purified Vpu was tested for its ability to induce channel activity in planar lipid bilayers using standard techniques as described elsewhere (Miller, 1986; and Piller et al, 1996). The solutions in the CIS and TRANS chambers were separated by a Delrin™ plastic wall containing a small circular hole of approximately 100 µm diameter across which a lipid bilayer was painted so as to form a high resistance electrical seal. Bilayers were painted from a mixture (8:2) of palmitoyl-oleoly-phosphatidyl-ethanolamine and palmitoyl-oleolyphosphatidyl-choline (Avanti Polar Lipids, Alabaster, Ala.) in n-decane. The solutions in the two chambers contained MES buffer (10 mM, pH 6.0) to which various NaCl or KCl concentrations were added. Currents were recorded with an Axopatch™ 200 amplifier. The electrical potential between the two chambers could be manipulated between +/−200 mV (TRANS relative to grounded CIS). Aliquots containing Vpu were added to the CIS chamber either as a detergent solution or after incorporation of the protein into phospholipid vesicles. The chamber was stirred until currents were observed.

EXAMPLE 10

Vpu Forms Ion Channels in Lipid Bilayers

Figure 3A:
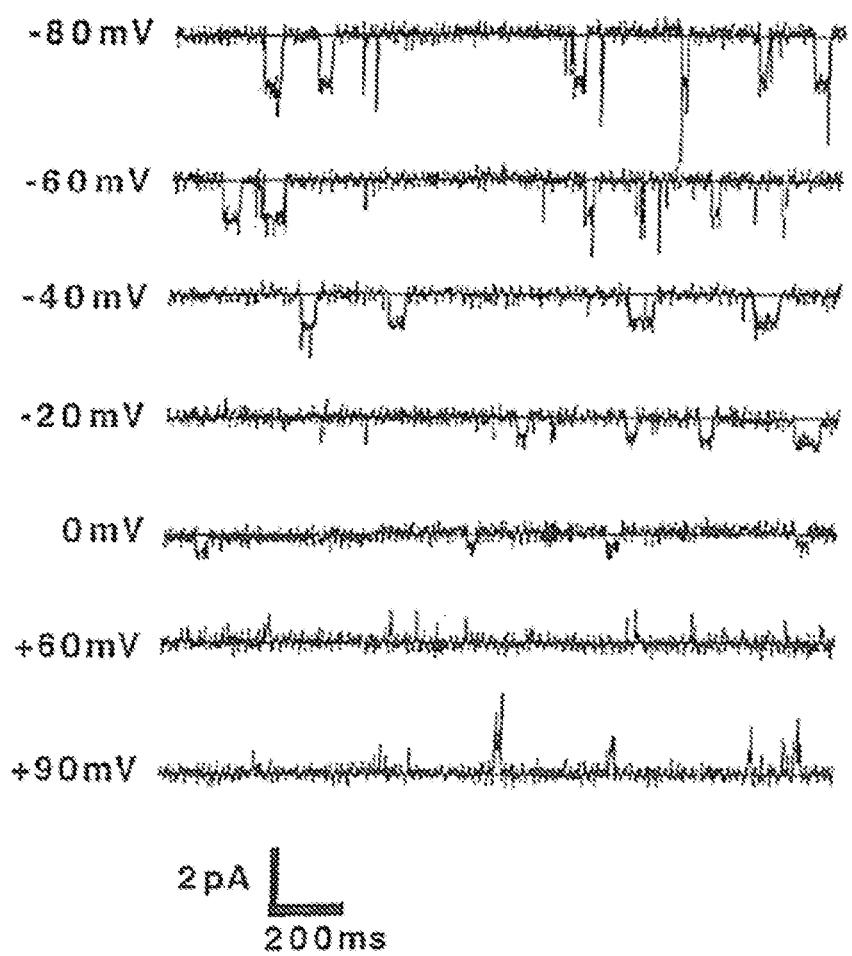
FIG. 3A-3B is a graphical representation of ion channel activity observed after exposure of lipid bilayers to aliquots containing purified Vpu. In 3A and 3B, the CIS chamber contained 500 mM NaCl and the TRANS chamber contained 50 mM NaCl; both solutions were buffered at pH 6.0 with 10 mM MES. 3B shows a current virus voltage curve generated from data similar to that shown in A.

To assay for ion-channel formation by Vpu, reconstitution into planar lipid bilayers was performed. When samples (containing between 7 and 70 ng of protein) of purified recombinant Vpu were added to the 1 ml of buffer in the CIS chamber of the bilayer apparatus, current fluctuations were detected after periods of stirring that varied from 2 to 30 min (FIG. 3). This time taken to observe channel activity approximately correlated with the amount of protein added to the chamber. No channels were detected when control buffer aliquots or control lipid vesicles were added to the CIS chamber. In those control experiments the chambers could be stirred for more than an hour without appearance of channel activity.

EXAMPLE 11

Properties of the Vpu Channels

Channel activity was observed in over 40 individual experiments with Vpu samples prepared from five independent purifications. In different experiments, the amplitude of the currents varied over a large range and, again, seemed to approximately correlate with the amount of protein added. The smallest and largest channels measured had conductances of 14 pS and 280 pS, respectively. The channels were consistently smaller when lipid vesicles containing Vpu were prepared and fused to the bilayer rather than when purified protein in detergent solution was added. This may be because the former method included treatment with high concentrations of detergent and a dilution step that may have favoured the breakdown of large aggregates into monomers.

Figure 3B:
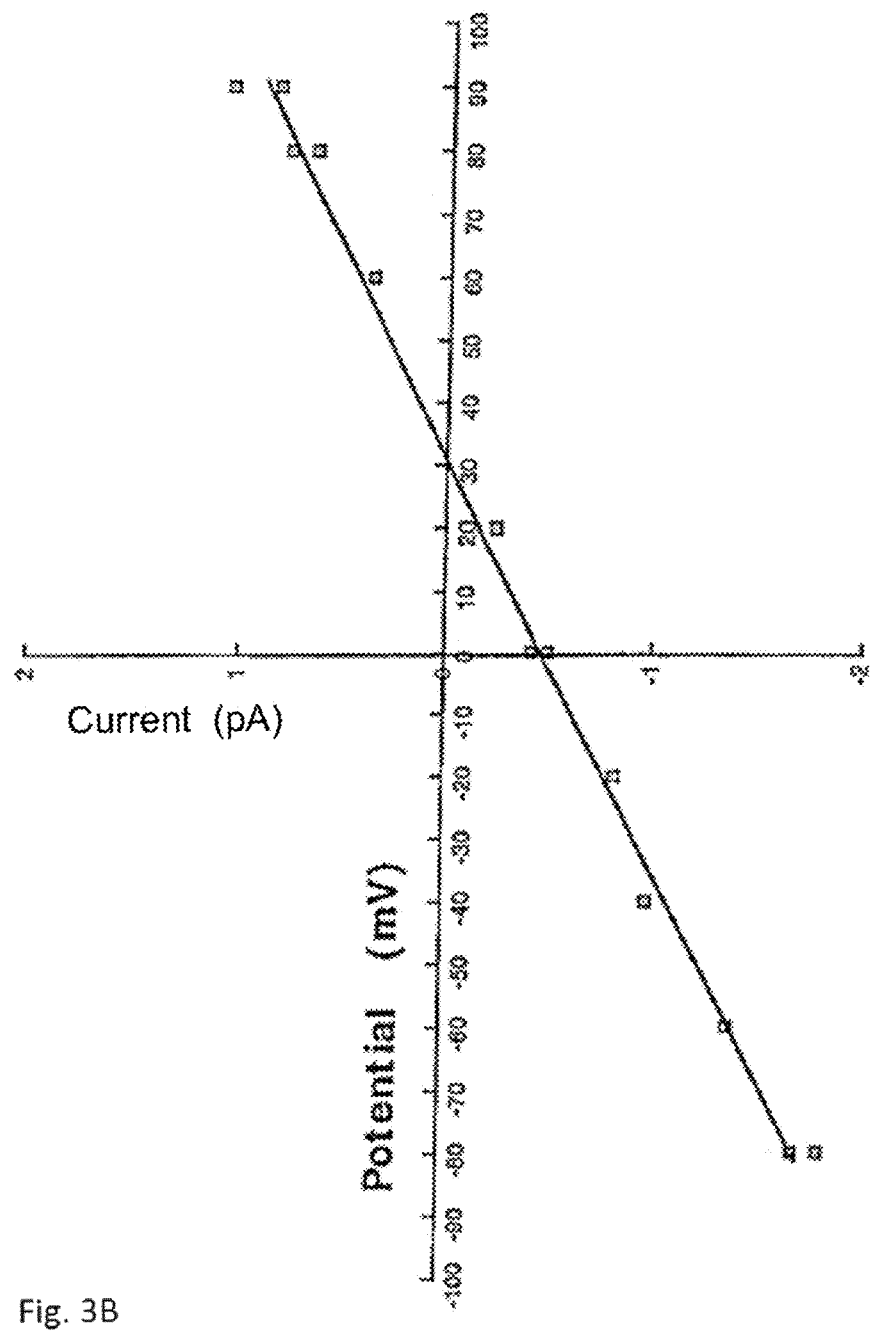

The relationship between current amplitude and voltage was linear and the reversal potential in solutions containing a ten-fold gradient of NaCl (500 mM CIS; 50 mM TRANS) was +3 0mV (FIG. 3B). A similar reversal potential was obtained when solutions contained KCl instead of NaCl. In 5 experiments with either NaCl or KCl in the solutions on either side of the membrane, the average reversal potential was 31.0+/−1.2 mV (+/−SEM). This is more negative than expected for a channel selectively permeable for the cations alone. Using ion activities in the Goldman-Hodgkin-Katz equation gives a $P_{Na}/P_{cl}$ ratio of about 5.5 indicating that the channels are also permeable to chloride ions. An attempt was made to reduce the anion current by substituting phosphate for chloride ions. When a Na-phosphate gradient (150 mM Na & 100 mM phosphate CIS; 15 mM $Na^+$ & 10 mM phosphate TRANS, pH 6.8) was used instead of the NaCl gradient, the reversal potential was 37.1+/−0.2 (+/−SEM, n=2) again indicating a cation/anion permeability ratio of about 5. (For calculations involving the phosphate solutions, the summed activities of the mono and bivalent anions were used and it was assumed that the two species were equally permeable). The current-voltage curve now exhibited rectification that was not seen in the NaCl solutions. It can be concluded that the channels formed by Vpu are equally permeably to $Na^+$ and $K^+$ and are also permeable, though to a lesser extent, to chloride as well as phosphate ions.

EXAMPLE 12

Bacterial Bio-Assay for Screening Potential Ion Channel-Blocking Drugs

This bio-assay is based on the observation that expression of Vpu in *E. coli* results in an active Vpu channel located in the plasmalemma that dissipates the transmembrane sodium gradient. As a consequence of this Vpu channel activity, metabolites whose accumulation within the cells is mediated by a sodium dependent co-transporter (for example proline or adenine) leak out of the cell faster than they can be synthesised so that the metabolites' intracellular levels become limiting for growth of the cell. Thereby, an *E. coli* cell expressing Vpu is unable to grow in minimal drop-out media lacking adenine or proline. However, in the presence of a drug that blocks the Vpu channel, the cell is once again able to re-establish its transmembrane sodium gradient—due to the action of other ion pumps in the membrane—and the leakage of metabolites is prevented enabling growth. Experiments to demonstrate that Vpu can form sodium channels in the plasma membrane of *E. coli* were performed as follows.

To express unfused Vpu in *E. coli*, the vpu open-reading frame was cloned into the plasmid pPL451 to create the recombinant plasmid pPL-Vpu (FIG. 1*b*). In this vector the strong $P_L$ and $P_R$ lambda promoters are used to drive expression of Vpu under control of the temperature sensitive c1857 represser, such that when grown at 30° C. expression is tightly repressed and can be induced by raising the temperature to between 37° C. and 42° C. On agar plates, cells containing pPL-Vpu grew when incubated at 30° C. and 37° C. but not at 42° C., while control strains grew well at 42° C. Liquid cultures of cells containing pPL-Vpu were grown at 30° C. to $OD_{600}$,=0.84 then moved to grow at 42° C. for two hours (the final cell density was $OD_{600}$,=0.75). The plasma membrane fraction was prepared and western blotting, using an antibody that specifically binds to the C-terminus of Vpu, detected a single band at approximately 16 kDa, indicating that Vpu was expressed and associated with the membranes (FIG. 2A, lane 5).

EXAMPLE 13

Figure 4A:
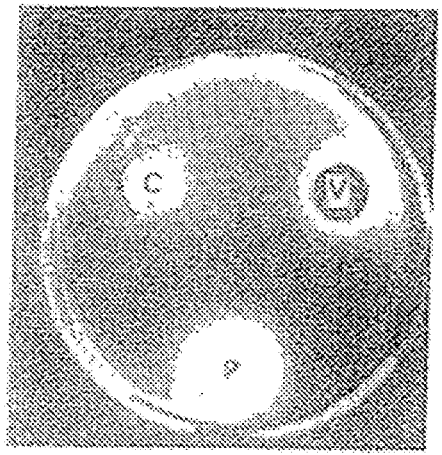
FIG. 4A-4C is a photographic representation of bacterial cross-feeding assays. For all plates, the Met⁻, Pro⁻ auxotrophic strain was used to seed a soft agar overlay. Plates 4A and 4B contain minimal drop-out medium minus proline; in plate 4C the medium was minus methionine. To control for viability of the cells in the background lawn, the discs labelled P and M contained added proline or methionine, respectively. The discs labelled C and V were inoculated with Met+, Prof E. coli cells containing the plasmids pPL451, or pPL+Vpu, respectively. Plates were incubated at 37° C. (4A and 4C) or 30° C. (4B) for two days and photographed above a black background with peripheral illumination from a fluorescent light located below the plate. The images were recorded on a Novaline video gel documentation system. Light halos around the discs labelled P or M on all plates and around the disc labelled V on plate A indicate growth of the background lawn strain.
Figure 4B:
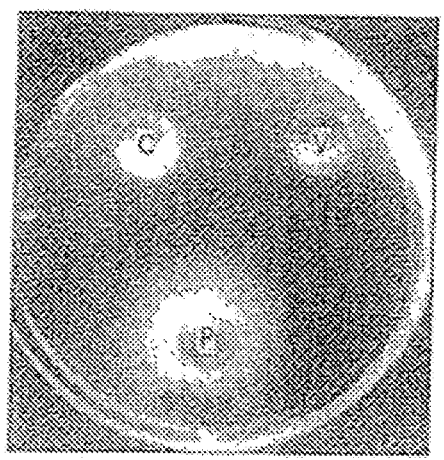

Cross-Feeding Experiments Reveal that Proline Leaks Out of Cells Expressing Vpu Uptake of proline by *E. coli* is well characterised and active transport of the amino acid into the cells is known to use the sodium gradient as the energy source (Yamato et al, 1994). To detect whether proline leakage occurs, the following cross-feeing assay was used: A lawn of an *E. coli* strain auxotrophic for proline and methionine (Met⁻Pro⁻), was seeded and poured as a soft agar overlay on minimal drop-out media plates lacking proline but containing methionine. Sterile porous filter discs were inoculated with a Met⁺Pro⁺ strain (XL-1 blue) containing either the pPL451 control plasmid or pPL-Vpu and placed onto the soft agar. The plates were then incubated at 37° C. or 30° C. for two days. After than time a halo growth of the Met⁻Pro⁻ strain was clearly visible surrounding the disc inoculated with the cells containing pPL-Vpu incubated at 37° C. (FIG. 4A). This growth can only be due to the leakage of proline from the Vpu-expressing cells on the disc. No such leakage was apparent from the control strain at 37° C. nor around either strain on plates grown at 30° C. (FIG. 4B).

Figure 4C:
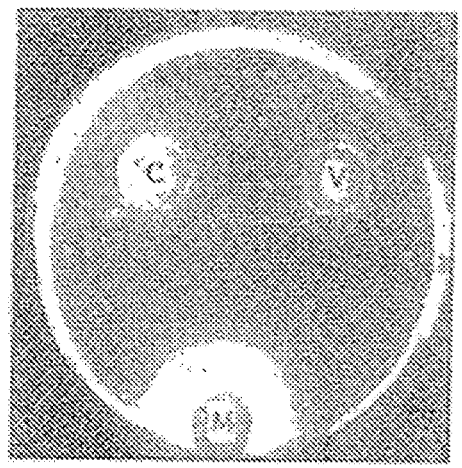

In contrast to proline transport, the *E. coli* methionine permease is known to belong to the ABC transporter family (Rosen, 1987) and hence be energised by ATP. Identical crossfeeding experiments to those described above were set us except that the Met⁻Pro⁻ strain was spread on minimal drop-out plates lacking methionine but containing proline. No growth of this strain was evident around any of the discs (FIG. 4C), indicating that methionine was not leaking out of the XL-1 blue cells even when Vpu was being expressed.

EXAMPLE 14

Figure 5:
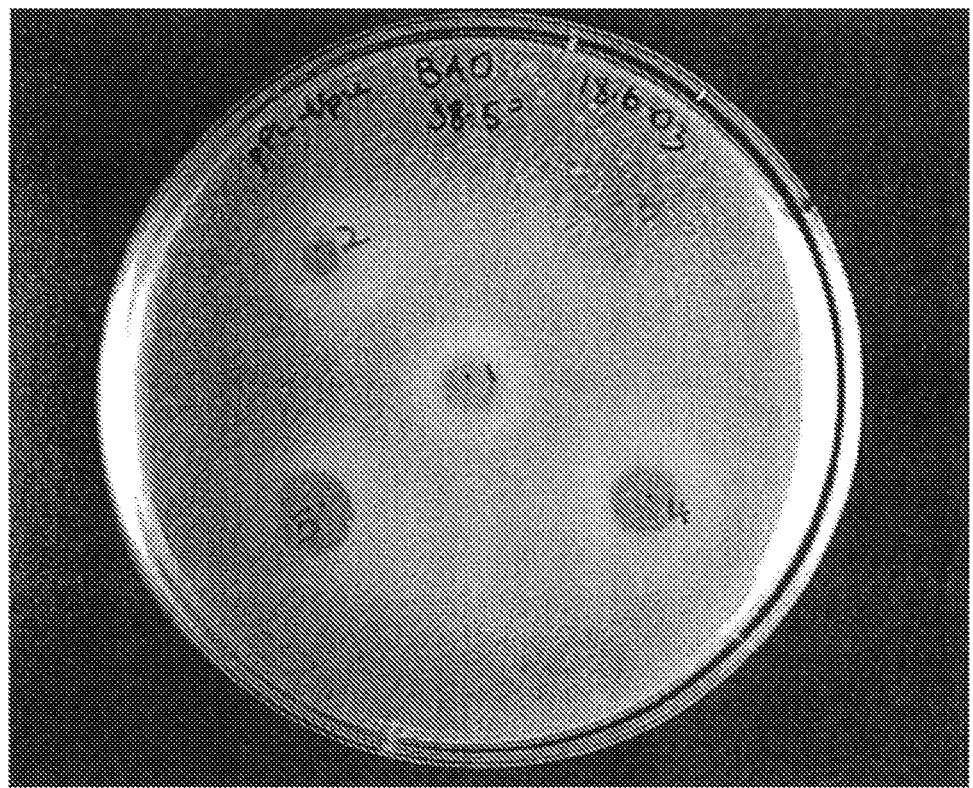
FIG. 5 is a graphical representation of the screening of drugs for potential Vpu channel blockers. The photograph shows a section of a minimal medium-lacking adenine-agarose plate onto which a lawn of XL-1-blue E. coli cells containing the Vpu expression plasmid pPLVpu has been seeded. Numbers 6-11 are located at the sites of application of various drugs being tested, which were applied in 3 µl drops and allowed to soak into the agarose. The plate was then incubated at 37° C. for 48 hr prior to being photographed. The background grey shade corresponds to areas of no bacterial growth. The bright circular area around "10" represents bacterial cell growth as a result of application of adenine at that location (positive control). The smaller halo of bacterial growth around "9" is due to the application of 5-(N,N-hexamethylene)-amiloride at that location.
Figure 6A:
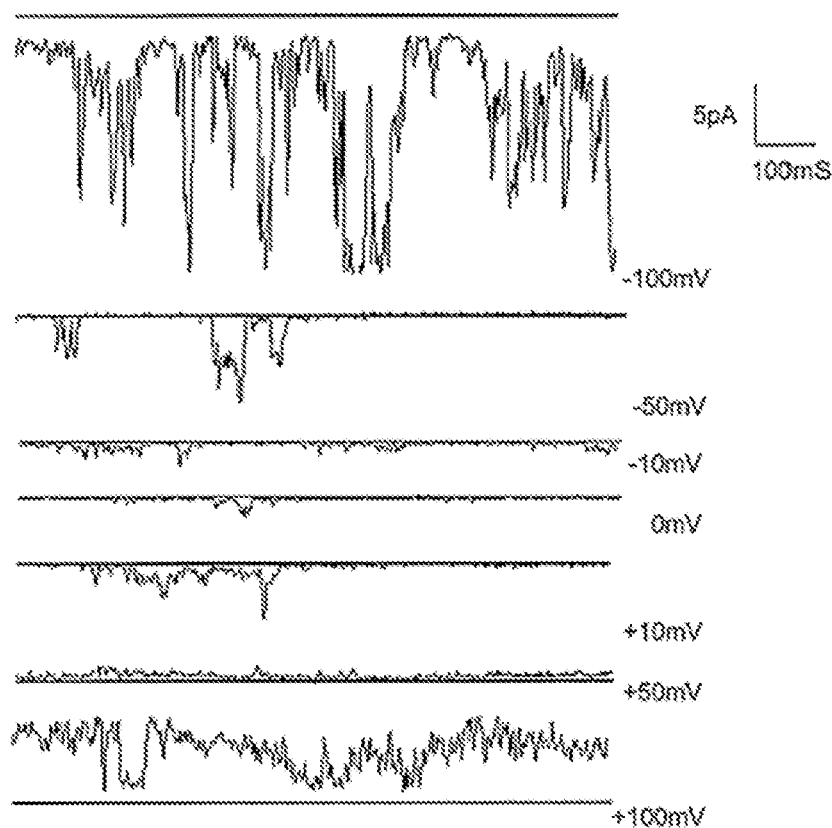
FIG. 6A-6B. SARS E protein ion channel activity observed in NaCl solutions after exposure of lipid bilayer to 3-10 mg of E protein. 6A. The closed state is shown as solid line, openings are derivations from the line. Scale bar is 300 ms and 5 pA. The CIS chamber contained 50 mM NaCl in 5 mM HEPES buffer pH 7.2, the TRANS chamber contained 500 mM NaCl in 5 mM HEPES buffer pH 7.2. The CIS chamber was earthed and the TRANS chamber was held at various potentials between −100 to +100 mV. 6B. Largest single opening events of a single channel.
Figure 6B:
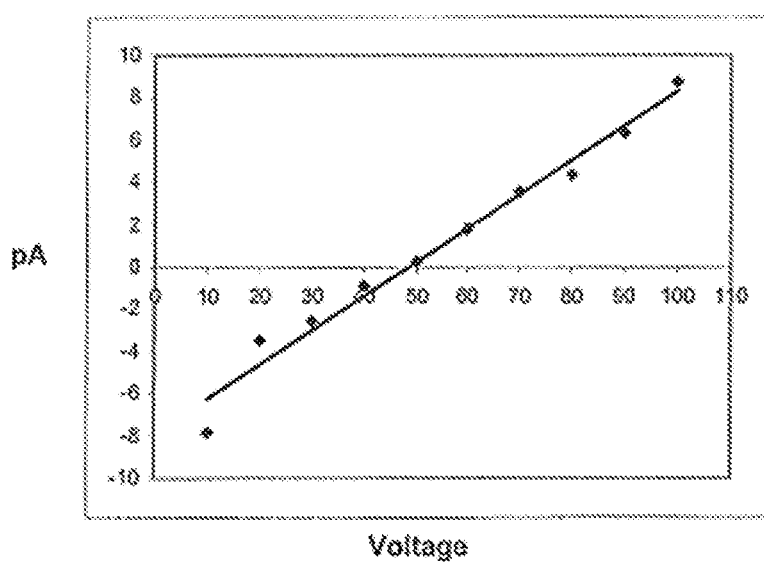
Figure 7A:
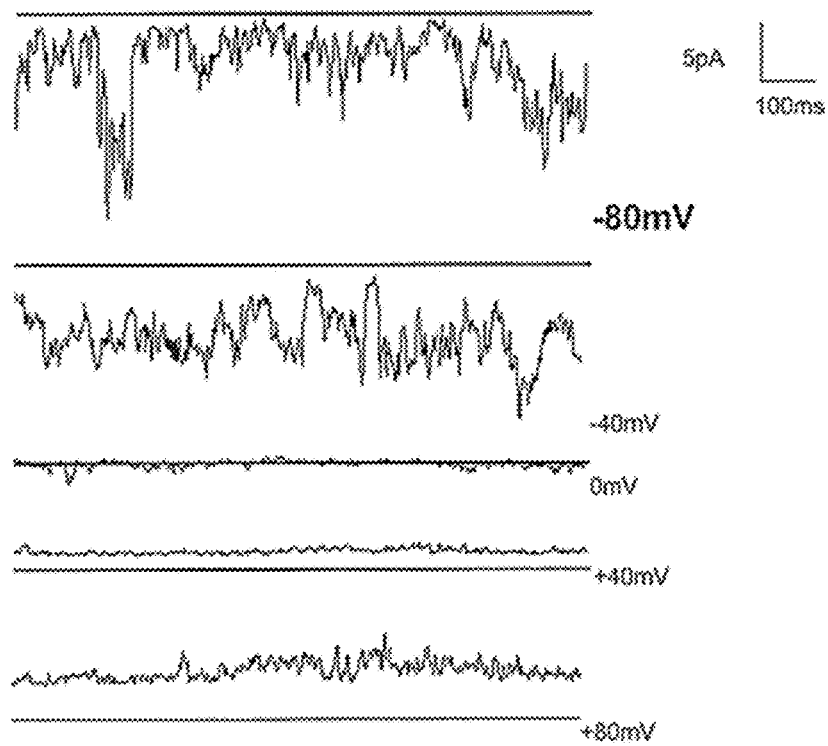
FIG. 7A-7B. SARS E protein ion channel activity observed in NaCl solutions after exposure of lipid bilayer to 3-10 mg of E protein. 7A. The closed state is shown as solid line, openings are derivations from the line. Scale bar is 300 ms and 5 pA. The CIS chamber contained 50 mM NaCl in 5 mM HEPES buffer pH 7.2. the TRANS chamber contained 500 mM NaCl in 5 mM HEPES buffer pH 7.2. The CIS chamber was earthed and the TRANS chamber was held at various potentials between −100 to +100 mV. 7B. Largest single opening events of a single channel.
Figure 7B:
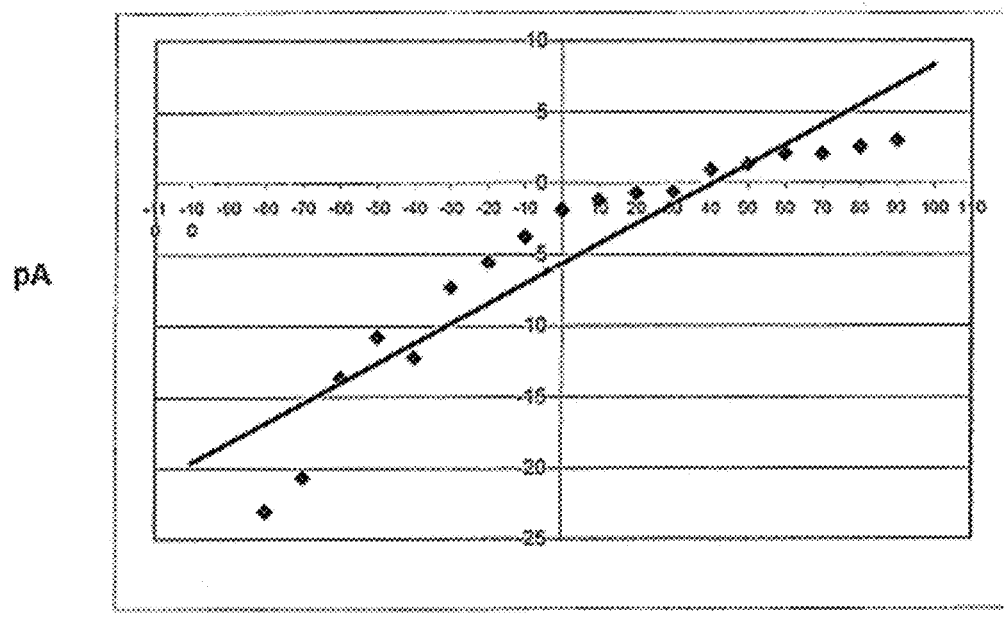
Figure 8A:
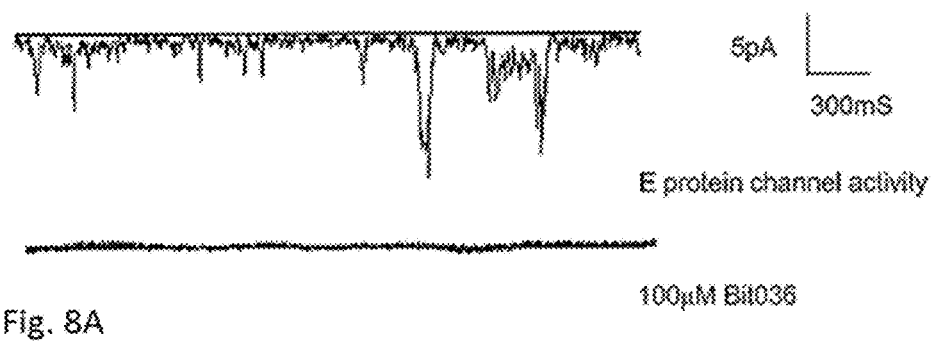
FIG. 8A-8C. Cinnamoylguanidine (Bit036) inhibits SARS E protein ion channel activity in NaCl solution. 8A. Representative currents at holding potential of −40 mV. Scale bar is 300 mS and 5 pA. E protein ion channel activity and E protein channel activity after the addition of 100 .mu.M Bit036. 8B. All points histogram at holding potential of −40 mV. E protein ion channel activity before and after the addition of 100 mM Bit036. 8C. Average current (pA), before formation of E protein ion channel, E protein ion channel activity and after addition of 100 .mu.pM Bit036.
Figure 8B:
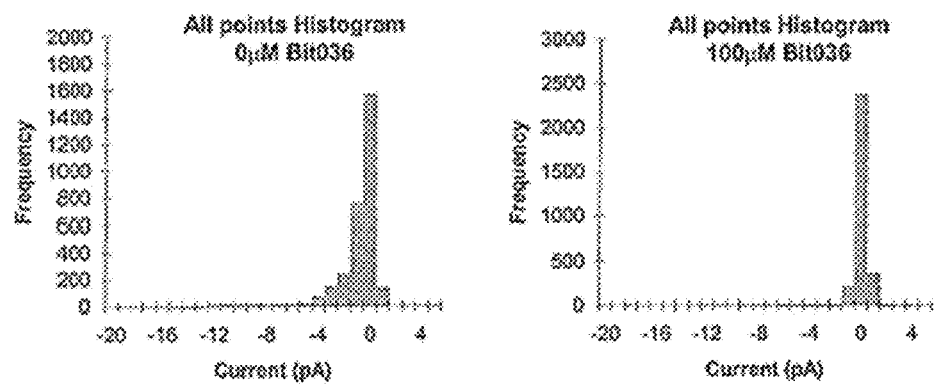
Figure 8C:
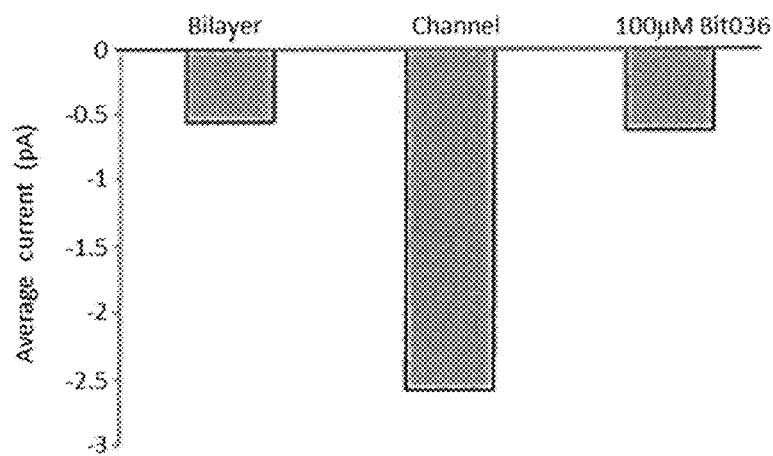

*E.Coli* Cells Expressing Vpu Require Adenine in the External Medium for Growth It was observed that, due to an uncharacterised mutation in the adenine synthesis pathway, growth of *E. coli* cells of the XL1-blue strain expressing Vpu at 37° C. was dependant on the presence of adenine in the medium. This allowed the development of an even simpler bioassay for Vpu ion-channel activity than the proline cross-feeding assay described above: A lawn of XL1-blue cells containing the pPL-Vpu plasmid is seeded onto an agarose plate lacking adenine in the medium, small aliquots of drugs to be tested for inhibition of the Vpu channel are spotted onto the agarose in discrete locations and the plates are incubated at 37° C. for a suitable period of time (12-36 hours). Halos of growth around a particular drug application site indicate that the drug has inhibited expression of the Vpu ion channel activity that prevents growth in the absence of the drug. (FIG. 5).

EXAMPLE 15

Assay of Compounds in Planar Lipid Bilayers for Vpu Channel Blocking Activity Compounds were characterized for their ability to block Vpu ion channel activity reconstituted into planar lipid bilayers. Vpu N-terminal peptide (residues 1-32) dissolved in trifluoroethanol was added to the CIS chamber of the bilayer apparatus and the solutions was stirred until ion currents were observed, indicating incorporation of one or more Vpu ion channels into the bilayer. After recording the channel activity for a few minutes, drugs were added to the solutions in the CIS and TRANS chambers—with stirring—to a final concentration of 100 µM. Channel activity was then recorded for at least a further three minutes and the effect of drug addition on ion current was determined by comparing the channel activity before and after drug addition. For each experiment, drug effect was classified into four categories: "Stong block", if current was inhibited approximately 90-100%; "weak block", approx. 50-90% inhibition; "partial block", <50%; and "no effect". Experiments were disregarded if currents larger than ±50 pA were generated after addition of Vpu N-peptide because in such cases it is possible that non-native peptide aggregates contribute to bilayer breakdown. Such aggregates, by virtue of their disorganized structure may not be specifically blocked by the drugs at the concentrations tested.

Table 3 summarises the results of the bilayer experiments. A novel outcome of these experiments was the strong blocking of Vpu channels observed with Phenamil. Phenamil has a phenyl group derivative at the guanidine group of amiloride. Amiloride itself is not a blocker of Vpu, whereas addition of the hexamethylene group at the 5-position of the pyrazine ring created a structure (HMA) that blocks the channel at concentrations as low as 25 µM. These new results with Phenamil, however, now show that a bulky hydrophobic derivative at the opposite end of the molecule can also turn amiloride into an effective Vpu channel blocker. Interestingly, benzamil, with a very similar structure was much less effective at blocking the Vpu channel.

TABLE 3

Summary of Compounds Inhibiting the Vpu Ion Channel in Bilayers

| Compound | No. of Expts. | Results |
|---|---|---|
| Phenamil | 3 | 3x Strong block |
| MIA | 2 | 1x Strong block; 1x weak |
| Benzamil | 10 | 3x partial block; 7x no effect |
| EIPA | 3 | 3x weak block; |
| HMA | 1 | 1x Strong block; |
| (5-Phenyl-penta-2,4-dienoyl)guanidine | 6 | 6x strong block |
| 6-methoxy-2-naphthoylguanidine | 5 | 5x strong block |
| (2-Chlorocinnamoyl)guanidine | 6 | 4x strong; 2x partial blocks |
| 3-(trifluoromethyl)cinnamoylguanidine | 5 | 4x strong blocks; 1x no effect |
| N-{5-[3-(5-Guanidino-pentyloxymethyl)-benzyloxy]-pentyl}-guanidine | 4 | 3x strong block; 1x no effect |
| 4-phenylbenzoylguanidine | 3 | 3x strong block |
| 3-methylcinnamoylguanidine | 4 | 2x strong block; 2x partial |
| (3-Chlorocinnamoyl)guanidine | 4 | 2x strong block; 2x partial |
| N-(3-phenylpropanoyl)-N'-phenylguanidine | 1 | 1x strong blocks |
| (3-Bromocinnamoyl)guanidine | 3 | 3x partial-strong block |
| 5-tert-butylamino-amiloride | 3 | 3x partial block |
| N-amidino-3-amino-5-phenyl-6-chloro-2-pyrazinecarboxamide | 3 | 3x partial block |
| 3-methoxy-HMA | 3 | 3x partial block |
| 5-(N-Methyl-N-isobutyl)amiloride | 1 | 1x partial block |
| 5-(N-Ethyl-N-isopropyl)amiloride | 1 | 1x partial block |
| 2-napthoylguanidine | 7 | 7x weak block |
| N,N'-bis(3phenylpropanoyl)-N''-phenylguanidine | 7 | 7x weak block |
| cinnamoylguanidine | 3 | 3x weak block |
| (5-Phenyl-penta-2,4-dienoyl)guanidine | 6 | 6x strong block |

EXAMPLE 16

Compound Screening Using the Bacterial Bio-Assay for the Vpu Protein

The halos of growth around the site of application of particular drugs—as described in example 14—were given a score between zero and six reflecting the size and density of the zone of bacterial cell growth. Scores greater than 3 represent strong inhibition of the Vpu protein; scores between 1.5 and 3 represent moderate inhibition and scores between 0.01 and 1.5 represent fair inhibition.

Table 4 lists the scores for inhibition of Vpu protein in the bacterial bio-assay.

TABLE 4

| Compound | Vpu Inhibition (score/# of times tested) |
|---|---|
| (3-Chlorocinnamoyl)guanidine | 4.38/4 |
| (3-Bromocinnamoyl)guanidine | 4.3/24 |
| (2-Chlorocinnamoyl)guanidine | 4.0/4 |
| (2-Bromocinnamoyl)guanidine | 3.7/2 |
| 3-(trifluoromethyl)cinnamoylguanidine | 3.7/2 |
| 5-bromo-2-fluorocinnamoylguanidine | 3.5/2 |
| 3-methylcinnamoylguanidine | 3.4/2 |
| 2-methylcinnamoylguanidine | 3.1/2 |
| 2,3-dimethylcinnamoylguanidine | 3.1/2 |
| cinnamoylguanidine | 2.96/12 |
| 6-methoxy-2-naphthoylguanidine | 2.9/4 |
| trans-3-(1-napthyl)acryloylguanidine | 2.9/3 |
| 3,4-dichlorocinnamoylguanidine | 2.9/3 |
| 2,6-dichlorocinnamoylguanidine | 2.88/2 |
| 4-phenylbenzoylguanidine | 2.75/5 |
| 2-ethylcinnamoylguanidine | 2.75/2 |
| (4-Chlorocinnamoyl)guanidine | 2.7/5 |
| 2-napthoylguanidine | 2.7/11 |
| 2,5-dimethylcinnamoylguanidine | 2.69/2 |

TABLE 4-continued

| Compound | Vpu Inhibition (score/# of times tested) |
|---|---|
| 3-isopropylcinnamoylguanidine hydrochloride | 2.6/2 |
| (5-Phenyl-penta-2,4-dienoyl)guanidine | 2.56/2 |
| 3-phenylcinnamoylguanidine | 2.54/3 |
| (4-Bromocinnamoyl)guanidine | 2.5/4 |
| 5-(3'-bromophenyl)penta-2,4-dienoylguanidine | 2.5/2 |
| 3-(cyclohex-1-en-1-yl)cinnamoylguanidine | 2.5/2 |
| 3-(trifluoromethoxy)cinnamoylguanidine | 2.44/2 |
| 2-(trifluoromethyl)cinnamoylguanidine | 2.4/2 |
| N,N'-bis(3phenylpropanoyl)-N''-phenylguanidine | 2.25/2 |
| 2-ethoxycinnamoylguanidine | 2.25/2 |
| N-(3-phenylpropanoyl)-N'-phenylguanidine | 2.21/3 |
| 4-(trifluoromethyl)cinnamoylguanidine | 2.2/2 |
| (4-Methoxycinnamoyl)guanidine | 2.13/2 |
| 2-t-butylcinnamoylguanidine | 2.13/2 |
| 4-methylcinnamoylguanidine | 2.1/2 |
| 2-fluorocinnamoylguanidine | 2.1/2 |
| 2-phenylcinnamoylguanidine | 2.1/2 |
| N-(6-Hydroxy-2-napthoyl)-N'-phenylguanidine | 2.06/2 |
| 3-t-butylcinnamoylguanidine | 2.06/2 |
| 3,4-difluorocinnamoylguanidine | 2.06/2 |
| 5-(N,N-hexamethylene)amiloride | 1.9/31 |
| 3-fluorocinnamoylguanidine | 1.9/2 |
| 5-bromo-2-methoxycinnamoylguanidine | 1.9/2 |
| 3-ethoxycinnamoylguanidine | 1.9/2 |
| 3,4-(methylenedioxy)cinnamoylguanidine | 1.88/2 |
| (2-Methoxycinnamoyl)guanidine | 1.7/4 |
| 2'4 DichloroBenzamil HCl | 1.7/2 |
| 2,3,5,6,-tetramethylcinnamoylguanidine | 1.6/2 |
| 3-(2-napthyl)acryloylguanidine | 1.56/2 |
| 2-(1-napthyl)acetoylguanidine | 1.56/2 |
| 2,3-difluorocinnamoylguanidine | 1.56/2 |
| (3-Methoxycinnamoyl)guanidine | 1.52/6 |
| 4-isopropylcinnamoylguanidine | 1.4/2 |
| 2,4,6-trimethylcinnamoylguanidine | 1.4/2 |
| N-(cinnamoyl)-N'phenylguanidine | 1.25/3 |
| 2-(cyclohex-1-en-1yl)cinnamoylguanidine | 1.2/2 |
| 2-(2-napthyl)acetoylguanidine | 1.19/2 |

TABLE 4-continued

| Compound | Vpu Inhibition (score/# of times tested) |
|---|---|
| (4-Hydroxycinnamoyl)guanidine | 1.1/2 |
| 4-phenylcinnamoylguanidine | 1.1/2 |
| 4-fluorocinnamoylguanidine | 1.1/2 |
| N,N'-bis-(cinnamoyl)-N"-phenylguanidine | 0.94/2 |
| (2-Furanacryloyl)guanidine | 0.94/2 |
| Phenamil methanesulfonate salt | 0.9/5 |
| Benzamil hydrochloride | 0.9/3 |
| (3-Nitrocinnamoyl)guanidine | 0.9/1 |
| Benzoylguanidine | 0.88/2 |
| (4-Phenoxybenzoyl)guanidine | 0.81/2 |
| 3-(trans-hept-1-en-1-yl)cinnamoylguanidine | 0.81/2 |
| 5-(N-Methyl-N-isobutyl)amiloride | 0.8/2 |
| 2-cyclohexylcinnamoylguanidine | 0.8/2 |
| 4-ethoxycinnamoylguanidine | 0.69/2 |
| 2,4-dichlorocinnamolyguanidine | 0.63/2 |
| 5-(N-Ethyl-N-isopropyl)amiloride | 0.6/3 |
| N-amidino-3-amino-5-hexamethyleneimino-6-phenyl-2-pyrazinecarboxamide | 0.6/2 |
| (a-Methylcinnamoyl)guanidine | 0.6/2 |
| cinnamoylguanidine hydrochloride | 0.6/2 |
| [(4-Chlorophenoxy-acetyl]guanidine | 0.56/2 |
| N-amidino-3-amino-5-phenyl-6-chloro-2-pyrazinecarboxamide | 0.5/11 |
| 5-(4-fluorophenyl)amiloride | 0.4/6 |
| (trans-2-Phenylcyclopropanecarbonyl)guanidine | 0.4/2 |
| (2-Nitrocinnamoyl)guanidine | 0.4/2 |
| trans-3-Furanacryoylguanidine | 0.38/2 |
| 1-napthoylguanidine | 0.3/2 |
| 5-tert-butylamino-amiloride | 0.2/7 |
| 3-methoxy-HMA | 0.2/4 |
| (3-phenylpropanoyl)guanidine | 0.2/4 |
| 4-t-butylcinnamoylguanidine | 0.19/2 |
| 5-(N,N-Dimethyl)amiloride hydrochloride | 0.1/2 |
| N,N'-Bis(3-phenylpropanoyl)guanidine | 0.1/2 |
| N-Benzoyl-N'-cinnamoylguanidine | 0.06/2 |
| 1-bromo-2-napthoylguanidine | 0.06/2 |

EXAMPLE 17

Effect of Compounds on HIV Replication in Human Monocytes and Macrophages

Human monocytes were isolated from peripheral blood and cultured either for 24 hr (one day old monocytes) or for 7 days to allow differentiation into monocyte derived macrophages (MDM). These cells were then exposed to cell-free preparations of HIV isolates and allowed to absorb for 2 hr before complete aspiration of the medium, washing once with virus-free medium and resuspension in fresh medium. The cells were exposed to various concentration of compound either 24 hr prior to infection or after infection. Subsequent HIV replication, at various times after infection, was compared in cells exposed to drugs and in cells not exposed to drugs (controls). The progression and extent of viral replication was assayed using either an HIV DNA PCR method (Fear et al, 1998) or an ELISA method to quantitate p24 in culture supernatants (Kelly et al, 1998).

Table 5 provides examples of results obtained using this assay and test anti-viral compounds.

TABLE 5

| Compound | Drug Conc. µM | Percent of Positive Control |
|---|---|---|
| None - positive control | | 100% |
| 4-phenylbenzoylguanidine | 10 | 26 |
|  | 5 | 4 |
|  | 2.5 | 9 |
|  | 1. | 216 |
|  | 0.625 | 10 |
| None - positive control | | 100% |
| (3-Bromocinnamoyl)guanidine | 10 | 3 |
|  | 5 | 1 |
|  | 2.5 | 9 |
|  | 1.25 | 59 |
|  | 0.625 | 116 |
| None - positive control | | 100% |
| 3-(trifluoro-methyl)cinnamoylguanidine | 10 | 11 |
|  | 5 | 8 |
|  | 2.5 | 25 |
|  | 1.25 | 27 |
|  | 0.625 | 38 |
| None - positive control | | 100% |
| 5-(N,N-hexamethylene)amiloride | 10 | 6 |
|  | 5 | 21 |
|  | 2.5 | 50 |
|  | 1.25 | 19 |
|  | 0.625 | 30 |

EXAMPLE 18

SARS Coronavirus

SARS E Protein Forms an Ion Channel

Peptide Synthesis

A peptide corresponding to the full-length SARS-CoV (isolate Tor2 and Urbani) E protein (MYSFVSEETGTLIVNSVLLFLAFVVFLLVTLAILTALRLCAYCCNIVNVSLVKPTVYVYSRVKNLNSSEGVPDLLV) (SEQ ID NO: 4) and a second peptide comprising the first 40 amino acids of the full length E protein which correspond to the transmembrane domain (MYSFVSEETGTLIVNSVLLFLAFVVF LLVTLAILTALRLC) (SEQ ID NO: 5) were synthesized manually using FMOC chemistry and solid phase peptide synthesis The synthesis was done at the Biomolecular Resource Facility (John Curtin School of Medical Research, ANU, Australia) using a Symphony$^R$ Peptide Synthesiser from Protein Technologies Inc.(Tucson, Ariz., USA) according to the manufacturers instructions.

EXAMPLE 19

Peptide Purification

Mass spectral analysis of the synthetic peptide revealed that the preparation contained significant amounts of material with lower m/z ratio than expected for the full-length product. The majority of these are presumably truncated peptides generated during the peptide synthesis process. To enrich the full-length E protein, the following procedure was used, which relies on differential solubility of the smaller molecules and full-length peptide. The crude preparation was suspended at 12 mg/ml in 70% $CH_3CN$, 0.1% TFA and vortexed for 10 minutes. This suspension was centrifuged at 10,000 g for 10 minutes at 20° C. The supernatant was discarded and the insoluble fractions was extracted with 70% CH3CN, 0.1% TFA, as above, two more times. The insoluble material containing the E protein was dried using Speedvac an the weight of the final product was used to calculate the yield. The purified peptide was analysed by Bruker Omniflex MALDI-TOF mass spectrometry in HABA matrix at 2.5 mg/ml in methanol at a 1:1 ratio and spectra were obtained in the positive linear mode. A clear peat at m/z ratio of 8,360.1 was seen as expected for the calculated molecular weight of full-length E protein and 4422.3 for the N-terminal E protein.

EXAMPLE 20

Planar Lipid Bilayers

The SARS virus E protein was resuspended at 1 mg/ml in 2,2,2-trifluoroethanol. The SARS virus E protein's ability to form ion channels was tested on a Warner (Warner instruments, Inc. 1125 Dixwell Avenue, Hamden, Conn. 06514) bilayer rig as follows; A lipid mix of 3:1:1, 1-Palmitoyl-2-oleolyl phosphatidyl Ethanolamine: 1-Palmitoyl-2-oleolyl phosphatidyl Serine: 1-Palmitoyl-2-oleolyl phosphatidyl choline in $CHCl_3$ was dried under $N_2$ gas and resuspended to 50 mg/ml in n-decane. Bilayers were painted across a circular hole of approximately 100 μm diameter in a Delrin™ cup separating aqueous solution in the CIS and TRANS chambers. The CIS chamber contained a solution of 500 mM NaCl or KCl, in a 5 mM HEPES buffer pH 7.2, the TRANS chamber contained a solution of 50 mM NaCl or KCl, in a 5 mM HEPES buffer pH 7.2. Silver electrodes coated in chloride with 2% agarose bridges are placed in the CIS and TRANS chamber solutions. The SARS E protein full-length or N-terminal peptides (3-10 ug) were added to the CIS chamber, which was stirred until channel activity was detected. The CIS chamber was earthed and the TRANS chamber was held at various holding potentials ranging between +100 to −100 mV. Currents were recorded using a Warner model BD-525D amplifier, filtered at 1 kHz, sampling at 5 kHz and digitally recorded on the hard disk of a PC using software developed in house.

Drugs to be tested for their ability to inhibit SARS E protein ion channel activity were made up at 50 mM in a solution of 50% DMSO: 50% methanol. For experiments testing the ability of compounds to inhibit E protein ion channel activity, 100 μM to 400 μM of compound was added to the CIS chamber while stirring for 30 seconds. Bilayer currents were recorded before channel activity, during channel activity and after the addition of the drug.

Among the compounds tested was cinnamoylguanidine (Bit036), a compound which was shown in earlier experiments to be antiviral and to inhibit ion channel proteins from other viruses.

EXAMPLE 20.1

Polyacrylamide Gel Electrophoresis

Purified E protein was dissolved to 1 mg/ml, 5 mg/ml and 10 mg/ml in, 6 M Urea, 10% Glycerol, 5% SDS, 500 mM DTT, 0.002% Bromophenol Blue, 62.5 mM Tris HCl (pH 8.3). Peptides in solutions were heated at 100° C. for 20 minutes before 30 μL samples were run on stacking gel 4-20% (Gradipore). SeeBlue® pre-stained standard (Invitrogen) was used for molecular weight markers.

EXAMPLE 20.2

Results

To test if the SARS E protein forms ion channels the purified synthetic peptide was reconstituted into planar lipid bilayers (21). Typically, 3 μg of SARS full-length E protein was added to the CIS chamber, while stirring. This CIS chamber contained 500 mM NaCl and the TRANS chamber contained 50 mM NaCl. In 60 experiments, ion currents due to SARS E protein ion channel activity were observed after about 5-15 minutes of stirring. Activity was detected more rapidly and reliably with a holding potential of approximately −100 mV across the bilayer. Currents recorded at −100 mV, (A) and at −60 mV (B) in one of these experiments are shown in FIG. 6. In that experiment the reversal potential was about +48 mV and the channel conductances were calculated to be 52 pS and 26 pS, respectively. This indicates that the current-voltage (IV) relationship is not linear. In ten other experiments, where no protein was added to the CIS chamber, no ion channel activity was detected, even after recording for over 1 hour.

FIG. 7*a* shows typical current traces recorded over a range of potentials in NaCl solutions. In that experiment the direction of current flow reversed at +48 mV (FIG. 7*b*). The IV curve shows that at the lower voltages the average current flow across the bilayer is small but at higher potentials there is an increase in average current across the bilayer, resulting in a non-linear IV relationship. In seven independent experiments, the average reversal potential was +48.3±2.3 mV (mean±1 SEM), indicating that the channels were about 37 times more permeable to Na+ ion than to $Cl^-$ ions. The reversal potential is close to the Na+ equilibrium potential (+53 mV), therefore the channel is selective for Na+ ions. For these 7 experiments the channel conductance varied between 95-164 pS; the average conductance was 130±13 pS.

SARS E protein ion channel is slightly less selectivity for $K^+$ ions than $Na^+$ ions. FIG. 8*b* shows recording of currents in KCl solutions at a range of potentials. In this experiment the currents reversed at +31 mV. In seven similar experiments E protein ion channel average reversal potential was +34.5±2.5 mV. Therefore the SARS E protein ion channel is about 7.2 times more permeable to $K^+$ ions than $Cl^-$ ions. In seven experiments, the channel conductance varied ranging between 24-166 pS, the average conductance was 83.4±26 pS.

Similar results were obtained with a second synthetic peptide, which corresponded to the first forty N-terminal amino acids of the SARS E protein "N-terminal peptide" (21). The average reversal potential in NaCl solution in four experiments was +46.3±2.5 mV, indicating that the ion channel formed by N-terminal peptide is about 25 times more permeable to Na+ ion than to Cl− ions. The SARS E protein N-terminal peptide was sufficient for the formation of ion channels with properties like those of the full length SARS E protein. Therefore, the selectivity filter for the SARS E protein is most likely contained within the first forty amino acids of the N-terminal.

SARS E protein N-terminal peptide also formed ion channels in KCl solution that were similarly selective for K+ ions compared to the full-length E protein. In five independent experiments the average channel reversal potential was +39.5±3.6 mV, therefore the channel is about 11 times more permeable to $K^+$ ions than $Cl^-$ ions.

SDS-PAGE of the purified full-length E protein peptide showed bands corresponding to the full-length E protein (Data not shown). Larger bands of varying size up to about 20 kDa were detected, suggesting that SARS E protein may form homo-oligomers.

EXAMPLE 21

SARS E Protein Ion Channel is Blocked by Cinnamoylguanidine and Other Compounds E protein ion channel activity in NaCl solutions was significantly reduced (p≥0.01, n=6 experiments) by addition of 100 to 200 µM cinnamoylguanidine to the CIS chamber. The average current across the bilayer was reduced to baseline by 100 µM cinnamoylguanidine. In experiments when E protein ion channels had higher conductance, 100 to 200 µM cinnamoulguanidine reduced the average current across the bilayer about 4 fold. Similarly, in four other experiments, 100 to 200 µM cinnamoylguanidine blocked channels formed by full-length E protein in KCl solutions. In two additional experiments, the SARS E protein N-terminal peptide was blocked by 100 to 200 µM cinnamoylguanidine, demonstrating that the cinnamoylguanidine drug-binding site is located within the first forty amino acids of the E protein N-terminal domain. Other compounds tested in bilayers for their effect on the SARS E protein are shown in below in Table 6.

TABLE 6

| Compound | % Reduction of average current by 100 µM |
|---|---|
| 5-(N,N-hexamethylene)amiloride | 91 ± 7 |
| 6-methoxy-2-naphthoylguanidine | 92 ± 16 |
| 2'4 DichloroBenzamil HCl | 78 ± 0 |
| N,N'-bis(3phenylpropanoyl)-N''-phenylguanidine | 88 ± 6 |
| (3-Bromocinnamoyl)guanidine | 87 ± 11 |
| (2-Bromocinnamoyl)guanidine | 88 ± 6 |
| trans-3-(1-napthyl)acryloylguanidine | 66 ± 2 |

EXAMPLE 21.1

Results and Discussion

We have shown that SARS E protein can form ion channels in lipid bilayer membranes. The ion currents reversed at positive potentials, which demonstrates that E protein ion channels are selective for monovalent cations over monovalent anions. E protein Ion channels were about 37 times more selective for $Na^+$ ions over $Cl^-$ ions and about 7.2 times more selective for $K^+$ ions over $Cl^-$ ions. In over 60 experiments the $Na^+$ conductance of the E protein ion channel varied from as low as 26 pS to as high as 164 pS. SDS-PAGE showed that the E protein forms homo-oligomers, and we surmised that the larger conductances were probably due to aggregation of the E protein peptide leading to larger ion channels or the synchronous opening of many ion channels. Single channel currents were observed in several experiments and from these the channel conductance was calculated to be voltage dependent.

The first 40 amino acids of the N-terminal which contains the hydrophobic domain of the SARS virus E protein is sufficient for the formation of ion channels on planar lipid bilayers. The N-terminal E protein ion channel has the same selectivity and conductance as the full-length E protein ion channel.

The SARS virus full length E protein ion channel activity and N-terminal domain E protein ion channel activity on planar lipid bilayers in NaCl and KCl solutions was inhibited by addition of between 100 µM to 200 µM cinnamoylguanidine to the CIS chamber. Inhibition or partial inhibition of the E protein ion channel activity by cinnamoylguanidine has been observed in seven independent experiments in NaCl solution and four independent experiments in KCl solution.

All known coronaviruses encode an E protein with a hydrophobic N-terminus transmembrane domain therefore all coronaviruses E proteins could form ion channels on planar lipid bilayers. This indicates that the E protein could be a suitable target for antiviral drugs and potentially stop the spread of coronavirus from infected host cells. Drugs that block the E protein ion channel could be effective antiviral therapy for the treatment of several significant human and veterinary coronavirus diseases including SARS and the common cold.

EXAMPLE 22

Bacterial Bio-Assay for Screening Potential SARS-CoV E Protein Ion Channel-Blocking Drugs SARS-CoV E Protein Ion Channel Inhibits Bacterial Cell Growth A bio-assay of SARS-CoV E protein function in bacterial cells was developed. A synthetic cDNA fragment encoding SARS-CoV E protein was cloned into the expression plasmid pPL451, creating a vector in which E protein expression is temperature inducible, as described in Example 4. Inhibition of the growth of E. coli cells expressing E protein at 37° C. was observed as an indicator of p7 ion channel function dissipating the normal $Na^+$ gradient maintained by the bacterial cells.

EXAMPLE 23

Compound Screening Using the Bacterial Bio-Assay for SARS Coronavirus E Protein

The halos of growth around the site of application of particular drugs—as described in example 14—were scored as described in example 15.

Table 7 lists the scores for inhibition of SARS-CoV E protein in the bacterial bio-assay.

TABLE 7

| Compound | SARS E protein Inhibition (score/# of times tested) |
|---|---|
| 2,3-difluorocinnamoylguanidine | 4.50/1 |
| 3,4-dichlorocinnamoylguanidine | 4.15/2 |
| 4-t-butylcinnamoylguanidine | 4.00/1 |
| 3-(2-napthyl)acryloylguanidine | 3.88/1 |
| (3-Chlorocinnamoyl)guanidine | 3.87/3 |
| 3-(cyclohex-1-en-1-yl)cinnamoylguanidine | 3.75/1 |
| 2,5-dimethylcinnamoylguanidine | 3.63/1 |
| trans-3-(1-napthyl)acryloylguanidine | 3.38/2 |
| 4-isopropylcinnamoylguanidine | 3.16/2 |
| (3-Bromocinnamoyl)guanidine | 3.15/27 |
| 6-methoxy-2-naphthoylguanidine | 3.13/3 |
| 5-(N-Methyl-N-isobutyl)amiloride | 3.13/2 |
| 3-phenylcinnamoylguanidine | 3.13/1 |
| (2-Chlorocinnamoyl)guanidine | 3.1/3 |
| 2'4 DichloroBenzamil HCl | 3.00/2 |
| 4-phenylcinnamoylguanidine | 2.75/2 |
| 4-(trifluoromethyl)cinnamoylguanidine | 2.75/1 |
| 3-(trifluoromethoxy)cinnamoylguanidine | 2.71/1 |
| 3-(trifluoromethyl)cinnamoylguanidine | 2.67/1 |
| 2-ethoxycinnamoylguanidine | 2.57/1 |
| cinnamoylguanidine hydrochloride | 2.50/1 |
| 4-ethoxycinnamoylguanidine | 2.48/2 |
| (2-Bromocinnamoyl)guanidine | 2.47/3 |
| 2,6-dichlorocinnamoylguanidine | 2.25/1 |
| 3,4,5-trimethoxycinnamoylguanidine | 2.25/1 |
| 5-tert-butylamino-amiloride | 2.01/2 |
| 3-t-butylcinnamoylguanidine | 2.00/1 |
| 5-bromo-2-fluorocinnamoylguanidine | 2.00/1 |
| (4-Chlorocinnamoyl)guanidine | 1.94/2 |
| 2-t-butylcinnamoylguanidine | 1.86/1 |

TABLE 7-continued

| Compound | SARS E protein Inhibition (score/# of times tested) |
|---|---|
| 2-cyclohexylcinnamoylguanidine | 1.83/1 |
| 6-Iodoamiloride | 1.75/2 |
| 3-(trans-hept-1-en-1-yl)cinnamoylguanidine | 1.71/1 |
| (4-Bromocinnamoyl)guanidine | 1.69/2 |
| (4-Hydroxycinnamoyl)guanidine | 1.63/2 |
| N-(3-phenylpropanoyl)-N'-phenylguanidine | 1.57/2 |
| (3-Nitrocinnamoyl)guanidine | 1.51/2 |
| 3-fluorocinnamoylguanidine | 1.50/1 |
| 2-(1-napthyl)acetoylguanidine | 1.50/1 |
| 2-ethylcinnamoylguanidine | 1.50/1 |
| 5-(N,N-Dimethyl)amiloride hydrochloride | 1.38/2 |
| 2-napthoylguanidine | 1.38/2 |
| 5-(4-fluorophenyl)amiloride | 1.38/1 |
| 2-(trifluoromethyl)cinnamoylguanidine | 1.38/1 |
| N-(6-Hydroxy-2-napthoyl)-N'-phenylguanidine | 1.35/3 |
| (trans-2-Phenylcyclopropanecarbonyl)guanidine | 1.34/3 |
| N,N'-bis(3phenylpropanoyl)-N''-phenylguanidine | 1.33/3 |
| 1-napthoylguanidine | 1.32/3 |
| Benzamil hydrochloride | 1.32/2 |
| 3-methoxy-HMA | 1.25/1 |
| 4-methylcinnamoylguanidine | 1.25/1 |
| 4-fluorocinnamoylguanidine | 1.25/1 |
| 3,4-(methylenedioxy)cinnamoylguanidine | 1.25/1 |
| 5-(N,N-hexamethylene)amiloride | 1.2/3 |
| N-(cinnamoyl)-N'phenylguanidine | 1.19/2 |
| 5-(N-Ethyl-N-isopropyl)amiloride | 1.07/2 |
| 3-methylcinnamoylguanidine | 1.00/1 |
| 2-methylcinnamoylguanidine | 1.00/1 |
| 2,3,5,6,-tetramethylcinnamoylguanidine | 1.00/1 |
| trans-2-Furanacryoylguanidine | 0.88/2 |
| (4-Methoxycinnamoyl)guanidine | 0.88/2 |
| (2-Furanacryloyl)guanidine | 0.82/2 |
| (3-phenylpropanoyl)guanidine | 0.73/5 |
| 2-(2-napthyl)acetoylguanidine | 0.71/1 |
| cinnamoylguanidine | 0.69/3 |
| (2-Methoxycinnamoyl)guanidine | 0.69/2 |
| [3-(3-Pyridyl)acryloyl]guanidine | 0.67/3 |
| 4-phenylbenzoylguanidine | 0.63/2 |
| 2,4-dichlorocinnamolyguanidine | 0.63/2 |
| (3-Methoxycinnamoyl)guanidine | 0.63/2 |
| 2-fluorocinnamoylguanidine | 0.63/1 |
| (4-Phenoxybenzoyl)guanidine | 0.57/2 |
| (a-Methylcinnamoyl)guanidine | 0.50/1 |
| 5-(3'-bromophenyl)penta-2,4-dienoylguanidine | 0.5/1 |
| (5-Phenyl-penta-2,4-dienoyl)guanidine | 0.44/2 |
| (Quinoline-2-carbonyl)guanidine | 0.41/1 |
| (Phenylacetyl)guanidine | 0.32/3 |
| N,N'-Bis(amidino)napthalene-2,6-dicarboxamide | 0.25/2 |
| 6-bromo-2-napthoylguanidine | 0.25/1 |
| 1-bromo-2-napthoylguanidine | 0.25/1 |
| 2-chloro-6-fluorocinnamoylguanidine | 0.25/1 |
| [(4-Chlorophenoxy-acetyl]guanidine | 0.19/2 |
| Phenamil methanesulfonate salt | 0.13/2 |
| N-Benzoyl-N'-cinnamoylguanidine | 0.13/2 |
| N-(2-napthoyl)-N'-phenylguanidine | 0.07/2 |

EXAMPLE 24

SARS Antiviral Assay for Testing Compounds Against Replication of SARS Coronavirus (SARS-CoV)

Compounds were tested against SARS-CoV (Hong Kong strain) using virus plaque purified three times in Vero cells. Stock virus was generated by infecting Vero cells at MOI=1×TCID$_{50}$ per 100 cells.

EXAMPLE 24.1

Screening for Anti-Viral Activity Using the Virus Microtitre Assay

Monolayers of Vero cells grown in 25 cm$^2$ flasks were infected at a multiplicity of 1:50 and treated immediately post infection with compounds at two concentrations, 10 uM and 2 uM. A control infected monolayer remained untreated. Samples of culture media were taken at 48 hours post infection. Two aliquots from each of the samples (titrations 1 and 2) were serially log diluted and 12 replicates of log dilutions −4 to −7 added to cells in microtitre plates. Four days later, wells in the microtitre plates were scored for cytopathic effect (CPE) and the titration values calculated based on the number of CPE positive wells at the 4 dilutions. Control titres were 4.8 and 5.9 TCID$_{50}$×10$^6$ (average 5.35× 10$^6$)

EXAMPLE 25

Effect of Compounds in SARS CoV Antiviral Assay

Three selected compounds were tested for activity against SARS-CoV according to the method described in example 21. For trans-3-(1-napthyl)acryloylguanidine and cinnamoylguanidine a decrease in virus titre of approximately 80% was observed at a concentration of 10 uM and a reduction of approximately 50% was seen to persist at 2 μM trans-3-(1-napthyl)acryloylguanidine.

Table 8 provides Virus titration data presented as % of a control (SARS CoV grown for 48 hours in the absence of compounds).

TABLE 8

| Compound | | Average | |
|---|---|---|---|
| Name | Concentration (uM) | TCID$_{50}$ (×10$^6$) | Titre (% control) |
| cinnamoylguanidine | 10 | 1.3 | 24 |
| | 2 | 4.4 | 82 |
| trans-3-(1-napthyl)acryloylguanidine | 10 | 1.15 | 22 |
| | 2 | 2.45 | 46 |
| 6-methoxy-2-naphthoylguanidine | 10 | 5.95 | 111 |
| | 2 | 6.35 | 118 |
| Control | 0 | 5.35 | 100 |

EXAMPLE 26

Human 229E Coronavirus

Synthesis and Purification of a Peptide Corresponding to the 229E-E Protein

A peptide corresponding to the full-length 229E-E protein (sequence: MFLKLVDDHALVVNVLLWCVVLIVILL-VCITIIKLIKLCFTCHMFCNRTVYGPIK NVYHIYQSYMHIDPFPKRVIDF (SEQ ID NO: 6); accession number NP_073554) was synthesized manually using FMOC chemistry and solid phase peptide synthesis. The synthesis was done at the Biomolecular Resource Facility (John Curtin School of Medical Research, ANU, Australia) using a SymphonyR Peptide Synthesiser from Protein Technologies Inc. (Woburn, Mass., USA) according to the manufacturers instructions to give C-terminal amides, the coupling was done with HBTU and hydroxybenzotriazole in N-methylpyrrolidone. Each of the synthesis cycles used double coupling and a 4-fold excess of the amino acids. Temporary α-N Fmoc-protecting groups were removed using 20% piperidine in DMF.

The crude synthetic peptide was purified using the ProteoPlus™ kit (Qbiogene inc. CA), following manufactures instructions. Briefly, the peptides were diluted in loading buffer (60 mM Tris-HCl pH 8.3, 6M urea, 5% SDS, 10% glycerol, 0.2% Bromophenol blue, ±100 mM β-mercaptoethanol) and run on 4-20% gradient polyacrylamide gels (Gradipore, NSW, Australia) in tris-glycine electrophoresis buffer (25 mM Tris, 250 mM glycine, 0.1% SDS). The peptides were stained with gel code blue (Promega, NSW) and the bands corresponding to the full-length peptide were excised out of the gel.

The gel slice was transferred to the ProteoPLUS™ tube and filled with tris-glycine electrophoresis buffer. The tubes were emerged in tris-glycine electrophoresis buffer and subjected to 100 volts for approximately 1 hour. The polarity of the electric current was reversed for 1 minute to increase the amount of protein recovered. The peptides were harvested and centrifuged at 13,000 rpm for 1 minute. The purified peptides were dried in a Speedvac and the weight of the final product was used to calculate the yield.

EXAMPLE 27

229E-E Protein Forms Ion Channels in Planar Lipid Bilayers

Lipid bilayer studies were performed as described elsewhere (Sunstrom, 1996; Miller, 1986). A lipid mixture of palmitoyl-oleoyl-phosphatidyl-ethanolamine, palmitoyl-oleoyl-phosphatidylserine and palmitoyl-oleoyl-phosphatidylcholine (5:3:2) (Avanti Polar Lipids, Alabaster, Ala.) was used. The lipid mixture was painted onto an aperture of 150-200 μm in the wall of a 1 ml delrin cup. The aperture separates two chambers, cis and trans, both containing salt solutions at different concentrations. The cis chamber was connected to ground and the trans chamber to the input of an Axopatch 200 amplifier. Normally the cis chamber contained either 500 mM NaCl or 500 mM KCl and the trans 50 mM NaCl or 50 mM KCl. The bilayer formation was monitored electrically by the amplitude of the current pulse generated by a current ramp. The potentials were measured in the trans chamber with respect to the cis. The synthetic peptide was added to the cis chamber and stirred until channel activity was seen. The currents were filtered at 1000 Hz, digitized at 5000 Hz and stored on magnetic disk.

The 229E E synthetic peptide was dissolved in 2,2,2-trifluorethanol (TFE) at 0.05 mg/ml to 1 mg/ml. 10 μl of this was added to the cis chamber (1 ml aqueous volume) of the bilayer apparatus, which was stirred via a magnetic "flea". Ionic currents, indicating channel activity in the bilayer, were typically detected within 15-30 min. After channels were detected the holding potential across the bilayer was varied between −100 mV and +100 mV to characterise the size and polarity of current flow and enable the reversal potential to be determined.

In 15 experiments where the cis chamber contained 500 mM NaCl solution and the trans chamber contained 50 mM NaCl solution, the average reversal potential of the channel activity was calculated to be 22±7 (SEM) mV. In 13 experiments where the cis chamber contained 500 mM KCl solution and the trans chamber contained 50 mM KCl solution, the average reversal potential of the channel activity was calculated to be 38±4 (SEM) mV. These results indicate that the 229E E protein forms cation selective ion channels that are slightly more selective for $K^+$ than for $Na^+$ ions.

Figure 9:
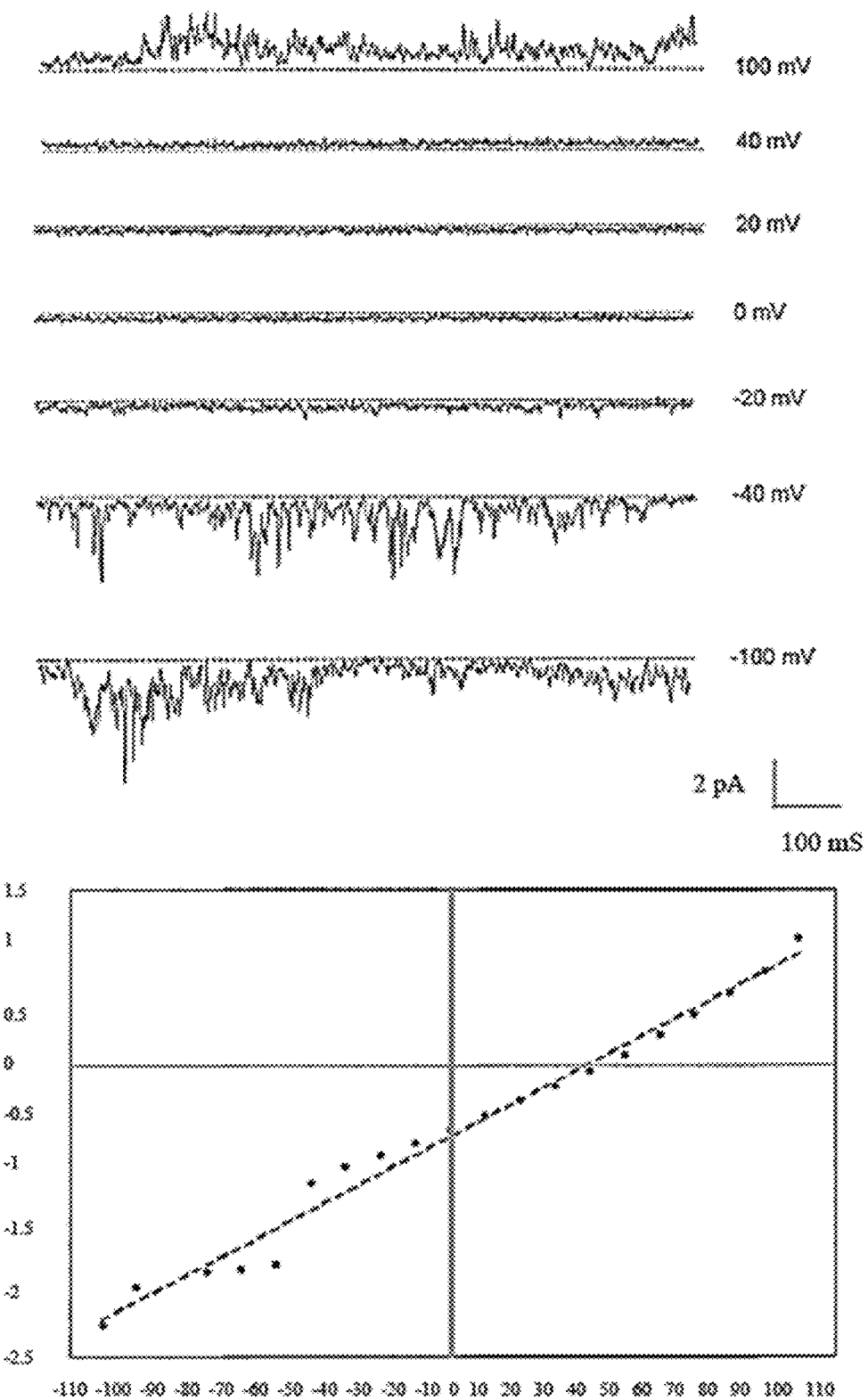
FIG. 9: 229E protein ion channel activity in lipid bilayers in KCl solutions.

FIG. 9 shows examples of raw current data for the 229E E ion channel at various holding potentials (cis relative to trans) in asymmetrical KCl solutions (500/50 mM). The graph is a representative plot of average bilayer current (pA; y-axis) versus holding potential (mV; x-axis).

EXAMPLE 28

Chemical Compounds Inhibit the Ion Channel Activity of the 229E E Protein Synthetic Peptide To test compounds for their ability to block or otherwise inhibit the ion channel formed by 229E E protein, small aliquots of solutions containing the compounds were added to the aqueous solutions bathing planar lipids in which the peptide channel activity had been reconstituted and the effect of the compound addition on the ionic currents was recorded and measured.

Compound stock solutions were typically prepared at 500 mM in DMSO. This solution was further diluted to 50 mM, or lower concentration in 50% DMSO/50% methanol and 2 μl of the appropriately diluted compound was added to the cis and/or trans chambers to yield the desired final concentration.

Figure 10A:
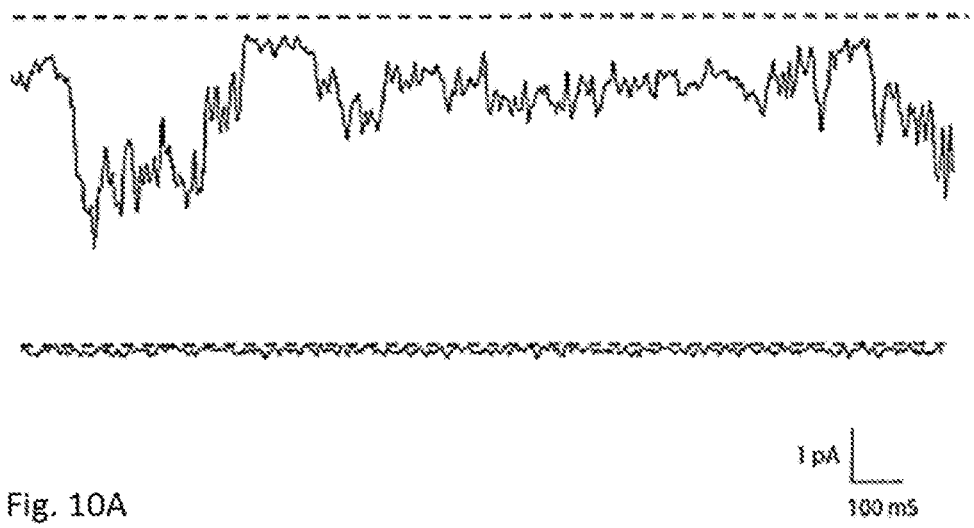
FIG. 10A-10B: Part 10A shows raw currents generated by the 229E-E protein ion channel in a planar lipid bilayer. The top trace shows current activity prior to drug addition and the lower trace shows the effect of addition of 100 μM cinnamoylguanidine on channel activity. Part 10B is a graphical representation of the average current flowing across the bilayer (in arbitrary units), before and after addition of cinnamoylguanidine.
Figure 10B:
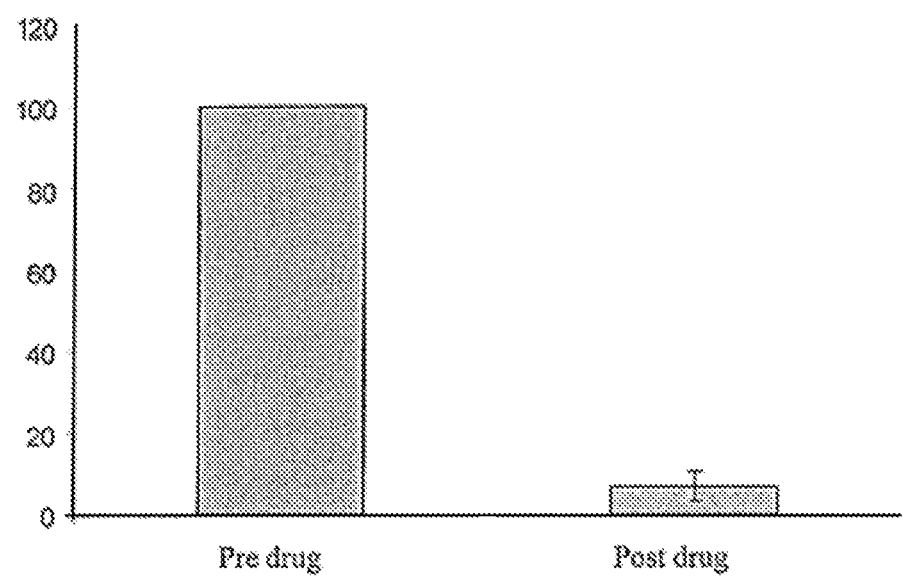

In the example shown in FIG. 10, addition of 100 μM cinnamoylguanidine to the cis chamber greatly reduced current flow through the 229E E ion channel.

EXAMPLE 29

Bacterial Bio-Assay for Screening Potential 229E-CoV E Protein Ion Channel-Blocking Drugs 229E-CoV E-Protein Ion Channel Inhibits Bacterial Cell Growth.

A bio-assay of 229E-CoV E-protein function in bacterial cells was developed. A synthetic cDNA fragment encoding 229E-CoV E-protein was cloned into the expression plasmid pPL451, creating a vector in which E protein expression is temperature inducible, as described in Example 4. Inhibition of the growth of E. coli cells expressing E protein at 37° C. was observed as an indicator of p7 ion channel function dissipating the normal Na+ gradient maintained by the bacterial cells.

EXAMPLE 30

Compound Screening Using the Bacterial Bio-Assay for 229E-CoV E-Protein

The halos of growth around the site of application of particular drugs—as described in example 14—were scored as described in example 15.

Table 9 list the scores for inhibition of 229E-CoV E-protein in the bacterial bio-assay.

TABLE 9

| Compound | 229E E protein Inhibition (score) |
|---|---|
| 4-isopropylcinnamoylguanidine | 4.9 |
| 3,4-dichlorocinnamoylguanidine | 4.4 |

TABLE 9-continued

| Compound | 229E E protein Inhibition (score) |
|---|---|
| 3-(trifluoromethoxy)cinnamoylguanidine | 4.1 |
| 4-t-butylcinnamoylguanidine | 4.0 |
| 3-isopropylcinnamoylguanidine hydrochloride | 4.0 |
| 3-t-butylcinnamoylguanidine | 3.9 |
| 2-t-butylcinnamoylguanidine | 3.9 |
| trans-3-(1-napthyl)acryloylguanidine | 3.7 |
| 5-bromo-2-methoxycinnamoylguanidine | 3.6 |
| 2,3-difluorocinnamoylguanidine | 3.3 |
| 3-(2-napthyl)acryloylguanidine | 3.0 |
| 2-phenylcinnamoylguanidine | 3.0 |
| 3-phenylcinnamoylguanidine | 2.9 |
| 3-(cyclohex-1-en-1-yl)cinnamoylguanidine | 2.4 |
| 4-phenylbenzoylguanidine | 2.3 |
| 3-(trifluoromethyl)cinnamoylguanidine | 2.3 |
| (4-Phenoxybenzoyl)guanidine | 2.3 |
| 4-(trifluoromethyl)cinnamoylguanidine | 2.3 |
| 2-(cyclohex-1-en-1yl)cinnamoylguanidine | 2.3 |
| (4-Bromocinnamoyl)guanidine | 2.0 |
| 5-(N,N-hexamethylene)amiloride | 1.9 |
| 1-napthoylguanidine | 1.9 |
| 5-(4-fluorophenyl)amiloride | 1.8 |
| (5-Phenyl-penta-2,4-dienoyl)guanidine | 1.8 |
| (3-Bromocinnamoyl)guanidine | 1.7 |
| 2,5-dimethylcinnamoylguanidine | 1.6 |
| 2-(trifluoromethyl)cinnamoylguanidine | 1.5 |
| 6-methoxy-2-naphthoylguanidine | 1.4 |
| (4-Chlorocinnamoyl)guanidine | 1.4 |
| (3-Methoxycinnamoyl)guanidine | 1.4 |
| 5-bromo-2-fluorocinnamoylguanidine | 1.4 |
| 5-(N,N-Dimethyl)amiloride hydrochloride | 1.3 |
| cinnamoylguanidine | 1.3 |
| (2-Methoxycinnamoyl)guanidine | 1.1 |
| (a-Methylcinnamoyl)guanidine | 1.0 |
| 4-phenylcinnamoylguanidine | 1.0 |
| 2,6-dichlorocinnamoylguanidine | 1.0 |
| (2-Bromocinnamoyl)guanidine | 0.9 |
| 2,4,6-trimethylcinnamoylguanidine | 0.9 |
| (trans-2-Phenylcyclopropanecarbonyl)guanidine | 0.8 |
| (3-Chlorocinnamoyl)guanidine | 0.8 |
| 2-(1-napthyl)acetoylguanidine | 0.8 |
| 2-ethylcinnamoylguanidine | 0.8 |
| 2-cyclohexylcinnamoylguanidine | 0.8 |
| (4-Hydroxycinnamoyl)guanidine | 0.6 |
| 2-ethoxycinnamoylguanidine | 0.6 |
| 3-methylcinnamoylguanidine | 0.5 |
| 2-methylcinnamoylguanidine | 0.5 |
| 3-fluorocinnamoylguanidine | 0.5 |
| cinnamoylguanidine hydrochloride | 0.5 |
| 2,3-dimethoylguanidine | 0.5 |
| 2-fluorocinnamoylguanidine | 0.4 |
| 4-fluorocinnamoylguanidine | 0.4 |
| 3,4-difluorocinnamoylguanidine | 0.4 |
| 5-tert-butylamino-amiloride | 0.3 |
| 2-napthoylguanidine | 0.3 |
| N,N'-Bis(amidino)napthalene-2,6-dicarboxamide | 0.3 |
| N,N'-Bis(3-phenylpropanoyl)guanidine | 0.3 |
| 4-methylcinnamoylguanidine | 0.3 |
| 5-(3'-bromophenyl)penta-2,4-dienoylguanidine | 0.3 |
| 2,3,5,6,-tetramethylcinnamoylguanidine | 0.3 |
| 3-ethoxycinnamoylguanidine | 0.3 |
| N,N'-bis(3phenylpropanoyl)-N''-phenylguanidine | 0.1 |
| (4-Methoxycinnamoyl)guanidine | 0.1 |
| (2-Chlorocinnamoyl)guanidine | 0.1 |
| (3-Nitrocinnamoyl)guanidine | 0.1 |
| 4-ethoxycinnamoylguanidine | 0.1 |
| 3,4,5-trimethoxycinnamoylguanidine | 0.1 |
| 2-(2-napthyl)acetoylguanidine | 0.1 |
| N-(3-phenylpropanoyl)-N'-phenylguanidine | 0.1 |

EXAMPLE 31

Antiviral Assay for Testing Compounds Against Replication of Human Coronavirus 229E (229E)

To determine the antiviral activity of compounds against human coronavirus 229E replication (ATCC VR-740), an assay measuring reduction in the number of plaques formed in monolayers of 229E infected MRC-5 cells (human lung fibroblasts; ATCC CCL-171) was developed: First, a virus working stock was prepared by amplification in MRC-5 cells. This was then used to infect confluent monolayers of MRC-5 cells grown in 6-well tissue culture plates by exposure to the virus at an MOI of approx. 0.01 pfu/cell for 1 hour at 35° C. in 5% $CO_2$. The infective inoculum was removed and replaced with fresh medium (DMEM supplemented with 10% fetal calf serum) containing various test concentrations of compounds or the appropriate level of solvent used for the compounds (control). Plates were subsequently incubated at 35° C. (in 5% $CO_2$) for 3-5 days post infection, after which time culture supernatant was removed and the cells were stained with 0.1% crystal violet solution in 20% ethanol for 10 minutes. Plaques were counted in all wells and the percentage reduction in plaque number compared to solvent control was calculated. Measurements were performed in duplicate to quadruplicate wells.

TABLE 10

| | Plaque Reduction (% control/# experiments) | | |
|---|---|---|---|
| Compound | 5 uM | 2.5 uM | 1 uM |
| 2-t-butylcinnamoylguanidine | 100/1 | 100/3 | 050/3 |
| 4-isopropylcinnamoylguanidine | 100/1 | 100/2 | 057/2 |
| 3,4-dichlorocinnamoylguanidine | 100/3 | 099/4 | 086/3 |
| 3-(trifluoromethoxy)cinnamoylguanidine | 100/2 | 098/4 | 077/3 |
| 2,6-dichlorocinnamoylguanidine | 100/1 | 097/3 | 066/2 |
| 2-(cyclohex-1-en-1yl)cinnamoylguanidine | 100/1 | 097/3 | 021/1 |
| 2-cyclohexylcinnamoylguanidine | 070/1 | 097/2 | 089/2 |
| 5-bromo-2-methoxycinnamoylguanidine | 100/2 | 096/4 | 088/3 |
| 2-phenylcinnamoylguanidine | 100/1 | 096/3 | 100/1 |
| 5-(2'-bromophenyl)penta-2,4-dienoylguanidine | 100/2 | 095/3 | 079/2 |
| 4-t-butylcinnamoylguanidine | 100/1 | 095/3 | 084/3 |
| 3-phenylcinnamoylguanidine | | 094/3 | 077/2 |
| (3-Bromocinnamoyl)guanidine | 100/2 | 093/3 | 072/2 |
| (4-Bromocinnamoyl)guanidine | 094/1 | 091/3 | 073/2 |
| 5-(N,N-hexamethylene)amiloride | 089/ | 091/2 | 033/1 |
| trans-3-(1-napthyl)acryloylguanidine | 100/1 | 091/2 | 064/2 |
| 3-(2-napthyl)acryloylguanidine | 100/1 | 091/2 | 062/2 |
| 2,4-dichlorocinnamolyguanidine | 100/2 | 090/4 | 064/3 |
| (2-Nitrocinnamoyl)guanidine | 085/2 | 090/2 | 046/2 |
| 3-(trifluoromethyl)cinnamoylguanidine | 097/2 | 089/4 | 064/3 |
| 5-bromo-2-fluorocinnamoylguanidine | 100/1 | 088/3 | 063/2 |
| 4-methylcinnamoylguanidine | 091/2 | 087/4 | 063/2 |
| (3-Chlorocinnamoyl)guanidine | 100/1 | 086/3 | 009/1 |
| (4-Methoxycinnamoyl)guanidine | 100/1 | 085/4 | 057/3 |
| (4-Chlorocinnamoyl)guanidine | 100/2 | 084/2 | 051/2 |
| 3-fluorocinnamoylguanidine | 095/1 | 083/3 | 051/2 |
| 3-(cyclohex-1-en-1-yl)cinnamoylguanidine | 100/1 | 082/3 | 063/2 |
| (a-Methylcinnamoyl)guanidine | 023/1 | 082/1 | 036/2 |
| 2,3,5,6,-tetramethylcinnamoylguanidine | 098/2 | 079/4 | 064/3 |
| 2-fluorocinnamoylguanidine | 090/1 | 079/3 | 045/2 |
| 4-(trifluoromethyl)cinnamoylguanidine | 100/1 | 079/1 | 052/1 |
| (3-Nitrocinnamoyl)guanidine | 100/1 | 079/1 | 045/1 |
| 2,5-dimethylcinnamoylguanidine | 092/2 | 078/1 | 078/1 |

TABLE 10-continued

| Compound | Plaque Reduction (% control/# experiments) | | |
|---|---|---|---|
| | 5 uM | 2.5 uM | 1 uM |
| 3-t-butylcinnamoylguanidine | 100/1 | 077/4 | 030/3 |
| (3-Methoxycinnamoyl)guanidine | 089/1 | 075/2 | 030/1 |
| 3-methylcinnamoylguanidine | 095/1 | 074/3 | 044/1 |
| 3-isopropylcinnamoylguanidine hydrochloride | 089/1 | 074/3 | 014/1 |
| (2-Bromocinnamoyl)guanidine | 095/2 | 072/2 | 043/2 |
| 3-ethoxycinnamoylguanidine | 100/1 | 072/3 | 057/1 |
| (5-Phenyl-penta-2,4-dienoyl)guanidine | 100/1 | 072/2 | 069/1 |
| (2-Chlorocinnamoyl)guanidine | 095/2 | 072/2 | 040/2 |
| 4-ethoxycinnamoylguanidine | 073/1 | 069/2 | 057/1 |
| 4-fluorocinnamoylguanidine | 100/1 | 067/3 | 034/2 |
| 3,4-difluorocinnamoylguanidine | 085/1 | 065/3 | 042/2 |
| N-(3-phenylpropanoyl)-N'-phenylguanidine | 051/1 | 064/1 | 000/1 |
| 2,4,6-trimethylcinnamoylguanidine | 075/2 | 063/3 | 062/2 |
| 2-methylcinnamoylguanidine | 074/2 | 063/3 | 053/3 |
| (trans-2-Phenylcyclopropanecarbonyl)-guanidine | | 063/2 | 022/1 |
| [(E)-3-(4-Dimethylaminophenyl)-2-methylacryloyl]guanidine | | 059/1 | |
| N-Benzoyl-N'-cinnamoylguanidine | | 056/1 | |
| 4-phenylbenzoylguanidine | 076/1 | 055/2 | 071/1 |
| trans-3-Furanacryoylguanidine | | 055/2 | 018/1 |
| (4-Phenoxybenzoyl)guanidine | 069/1 | 054/3 | 040/2 |
| (2-Methoxycinnamoyl)guanidine | 051/1 | 053/2 | 024/1 |
| N-amidino-3-amino-5-phenyl-6-chloro-2-pyrazinecarboxamide | 074/2 | 052/2 | 038/1 |
| N-(cinnamoyl)-N'phenylguanidine | 084/1 | 048/2 | 035/1 |
| cinnamoylguanidine | 095/2 | 047/2 | 059/1 |
| 3,4-(methylenedioxy)cinnamoylguanidine | 084/1 | 046/1 | 019/1 |
| N,N'-Bis(amidino)napthalene-2,6-dicarboxamide | | 045/1 | |
| 2,3-dimethylcinnamoylguanidine | 073/1 | 044/2 | 024/1 |
| 5-(3'-bromophenyl)penta-2,4-dienoylguanidine | | 044/1 | |
| N,N'-Bis(3-phenylpropanoyl)guanidine | | 041/1 | |
| 3-methoxy-amiloride | 029/2 | 039/3 | 022/2 |
| 2,3-difluorocinnamoylguanidine | | 036/1 | |
| 1-napthoylguanidine | | 036/1 | |
| (3-phenylpropanoyl)guanidine | | 036/1 | |
| 6-methoxy-2-naphthoylguanidine | 49/3 | 030/4 | |
| 5-(N,N-Dimethyl)amiloride hydrochloride | | 027/1 | |
| 2-ethoxycinnamoylguanidine | | 027/1 | |
| 2-napthoylguanidine | | 027/1 | |
| 3,4,5-trimethoxycinnamoylguanidine | | 027/1 | |
| 3-methoxy-HMA | | 027/1 | |
| Benzoyolguanidine | | 026/1 | |
| 2-(trifluoromethyl)cinnamoylguanidine | | 022/1 | |
| N-amidino-3,5-diamino-6-phynyl-2-pyrazinecarboxamide | | 022/1 | |
| cinnamoylguanidine hydrochloride | | 020/1 | |
| (Quinoline-2-carbonyl)guanidine | 015/3 | 019/3 | 006/2 |
| (4-Hydroxycinnamoyl)guanidine | | 019/1 | |
| 5-(4-fluorophenyl)amiloride | | 018/1 | |
| 2-(1-napthyl)acetoylguanidine | | 018/1 | |
| (2-Furanacryloyl)guanidine | | 018/1 | |
| [3-(3-Pyridyl)acryloyl]guanidine | | 018/1 | |
| N-Cinnamoyl-N',N'-dimethylguanidine | | 015/1 | |
| N-(2-napthoyl)-N'-phenylguanidine | | 011/1 | |
| 2-(2-napthyl)acetoylguanidine | | 009/1 | |
| N,N'-bis(3phenylpropanoyl)-N''-phenylguanidine | | 009/1 | |
| (Phenylacetyl)guanidine | | 009/1 | |

EXAMPLE 32

Human OC43 Coronavirus

OC43 Antiviral Assay for Testing Compounds Against Replication of Human Coronavirus OC43.

To determine the antiviral activity of compounds against human coronavirus OC43 replication (ATCC VR-759), an ELISA assay was developed measuring the release of the viral N-protein into culture supernatants from monolayers of OC43-infected MRC-5 cells (human lung fibroblasts; ATCC CCL-171): First, a virus working stock was prepared by amplification in MRC-5 cells. This was then used to infect confluent monolayers of MRC-5 cells grown in 6-well tissue culture plates by exposure to the virus at an MOI of approx. 0.01 pfu/cell for 1 hour at 35° C. in 5% $CO_2$. The infective inoculum was removed and replaced with fresh medium (DMEM supplemented with 10% fetal calf serum) containing various test concentrations of compounds or the appropriate level of solvent used for the compounds (control). Plates were subsequently incubated at 35° C. (in 5% $CO_2$) for 5 days post infection, after which time culture supernatant was harvested and cellular debris removed by centrifugation at 5000×g for 10 minutes. For N-antigen detection, 100 µl samples of clarified culture supernatant were added to duplicate wells of a 96-well Maxi-Sorb plate; 100 µl of RIPA buffer was added per well with mixing and the plate was covered and incubated at 4° C. overnight to enable protein binding to the plastic wells. The next day, the coating solution was discarded, wells were washed thoroughly with PBST, and blocking of unoccupied protein binding sites was performed by incubation in 1% BSA in PBS for 1.5 hours. The antibody recognising OC43 N-protein was used at 1/800 dilution in PBS (1 hr at 37° C.) and the secondary antibody (goat-anti-mouse alkaline phosphatase) was used for the colour development reaction. Optical density of the wells was read at 405 nm and the effect of compounds determined by comparison of the level of signal in presence of compound to level of signal from the solvent control.

EXAMPLE 33

Effect of Compounds in OC43 Antiviral Assay

Compounds were screened for activity against OC43 replication according to the method described in example 22. Results are shown in Table 11.

TABLE 11

| Compound | Virus inhibition at 2.5 uM |
|---|---|
| 3-methylcinnamoylguanidine | 100 |
| trans-3-(1-napthyl)acryloylguanidine | 100 |
| (3-Bromocinnamoyl)guanidine | 100 |
| (2-Chlorocinnamoyl)guanidine | 96 |
| 3,4-dichlorocinnamoylguanidine | 90 |
| 3-(trifluoromethyl)cinnamoylguanidine | 84 |
| (trans-2-Phenylcyclopropanecarbonyl)guanidine | 71 |
| 4-isopropylcinnamoylguanidine | 68 |
| cinnamoylguanidine | 57 |
| 6-methoxy-2-naphthoylguanidine | 47 |
| 2,4-dichlorocinnamoylguanidine | 36 |
| (4-Chlorocinnamoyl)guanidine | 36 |
| 5-(N,N-hexamethylene)amiloride | 30 |
| (4-Bromocinnamoyl)guanidine | 29 |
| 2,6-dichlorocinnamoylguanidine | 27 |
| 5-bromo-2-methoxycinnamoylguanidine | 24 |
| (5-Phenyl-penta-2,4-dienoyl)guanidine | 9 |

TABLE 11-continued

| Compound | Virus inhibition at 2.5 uM |
|---|---|
| 3-(trifluoromethoxy)cinnamoylguanidine | 4 |
| 2-t-butylcinnamoylguanidine | 4 |

EXAMPLE 34

Mouse Hepatitis Virus (MHV)

Synthesis and Purification of a Peptide Corresponding to the MHV-A59 E Protein.

A peptide corresponding to the full-length MHV-A59 E protein (sequence: MFNLFLTDTVWYVGQIIFI-FAVCLMVTIIVVAFLASIKLCIQLCGLCNTL VLSPSIY-LYDRSKQLYKYYNEEMRLPLLEVDDI (SEQ ID NO: 7); accession number NP_068673) was synthesized manually using FMOC chemistry and solid phase peptide synthesis The synthesis was done at the Biomolecular Resource Facility (John Curtin School of Medical Research, ANU, Australia) using a Symphony$^R$ Peptide Synthesiser from Protein Technologies Inc. (Woburn, Mass., USA) according to the manufacturers instructions to give C-terminal amides, the coupling was done with HBTU and hydroxybenzotriazole in N-methylpyrrolidone. Each of the synthesis cycles used double coupling and a 4-fold excess of the amino acids. Temporary α-N Fmoc-protecting groups were removed using 20% piperidine in DMF.

The crude synthetic peptide was purified using the ProteoPlus™ kit (Qbiogene inc. CA), following manufactures instructions. Briefly, the peptides were diluted in loading buffer (60 mM Tris-HCl pH 8.3, 6M urea, 5% SDS, 10% glycerol, 0.2% Bromophenol blue, ±100 mM β-mercaptoethanol) and run on 4-20% gradient polyacrylamide gels (Gradipore, NSW, Australia) in tris-glycine electrophoresis buffer (25 mM Tris, 250 mM glycine, 0.1% SDS). The peptides were stained with gel code blue (Promega, NSW) and the bands corresponding to the full-length peptide were excised out of the gel.

The gel slice was transferred to the ProteoPLUS™ tube and filled with tris-glycine electrophoresis buffer. The tubes were emerged in tris-glycine electrophoresis buffer and subjected to 100 volts for approximately 1 hour. The polarity of the electric current was reversed for 1 minute to increase the amount of protein recovered. The peptides were harvested and centrifuged at 13,000 rpm for 1 minute. The purified peptides were dried in a Speedvac and the weight of the final product was used to calculate the yield.

EXAMPLE 35

MHV-E Protein Forms Ion Channels in Planar Lipid Bilayers

Lipid bilayer studies were performed as described elsewhere (Sunstrom, 1996; Miller, 1986). A lipid mixture of palmitoyl-oleoyl-phosphatidyl-ethanolamine, palmitoyl-oleoyl-phosphatidylserine and palmitoyl-oleoyl-phosphatidylcholine (5:3:2) (Avanti Polar Lipids, Alabaster, Ala.) was used. The lipid mixture was painted onto an aperture of 150-200 μm in the wall of a 1 ml delrin cup. The aperture separates two chambers, cis and trans, both containing salt solutions at different concentrations. The cis chamber was connected to ground and the trans chamber to the input of an Axopatch 200 amplifier. Normally the cis chamber contained either 500 mM NaCl or 500 mM KCl and the trans 50 mM NaCl or 50 mM KCl. The bilayer formation was monitored electrically by the amplitude of the current pulse generated by a current ramp. The potentials were measured in the trans chamber with respect to the cis. The synthetic peptide was added to the cis chamber and stirred until channel activity was seen. The currents were filtered at 1000 Hz, digitized at 5000 Hz and stored on magnetic disk.

The MHV E synthetic peptide was dissolved in 2,2,2-trifluorethanol (TFE) at 0.05 mg/ml to 1 mg/ml. 10 μl of this was added to the cis chamber (1 ml aqueous volume) of the bilayer apparatus, which was stirred via a magnetic "flea". Ionic currents, indicating channel activity in the bilayer, were typically detected within 15-30 min. After channels were detected the holding potential across the bilayer was varied between −100 mV and +100 mV to characterise the size and polarity of current flow and enable the reversal potential to be determined.

In 14 experiments where the cis chamber contained 500 mM NaCl solution and the trans chamber contained 50 mM NaCl solution, the average reversal potential of the channel activity was calculated to be 49±1 (SEM) mV. In 11 experiments where the cis chamber contained 500 mM KCl solution and the trans chamber contained 50 mM KCl solution, the average reversal potential of the channel activity was calculated to be 13±6 (SEM) mV. These results indicate that the MHV E protein forms cation selective ion channels that are more selective for Na$^+$ than for K$^+$ ions.

Figure 11:
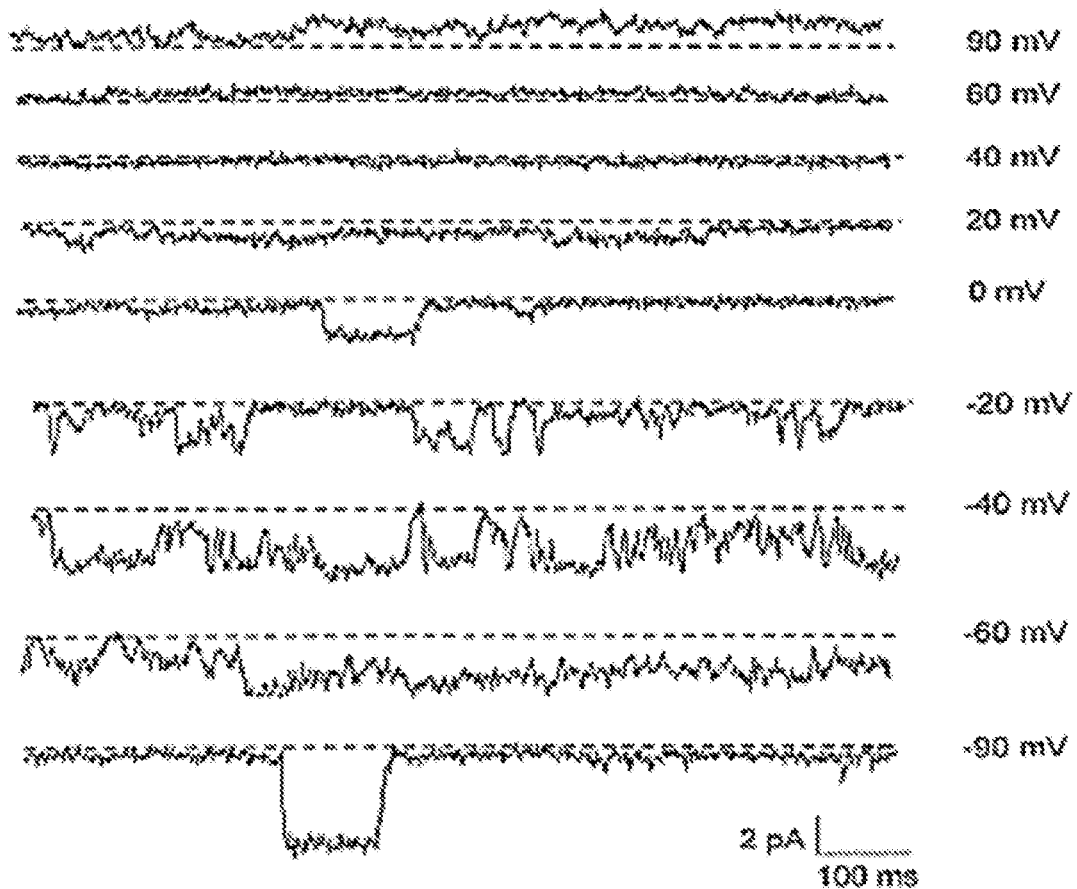
FIG. 11: MHV E protein Ion channel activity in lipid bilayars NaCl solutions.
Figure 11:
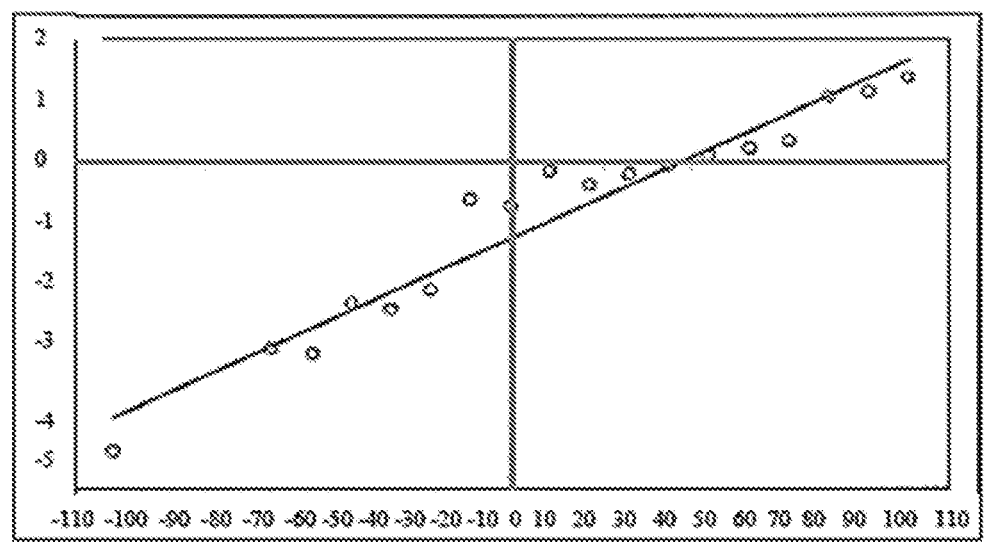

FIG. 11 shows examples of raw current data for the MHV E ion channel at various holding potentials (cis relative to trans) in asymmetrical NaCl solutions (500/50 mM). The graph is a representative plot of average bilayer current (pA; y-axis) versus holding potential (mV; x-axis).

EXAMPLE 36

Chemical Compounds Inhibit the Ion Channel Activity of the MHV E Protein Synthetic Peptide To test compounds for their ability to block or otherwise inhibit the ion channel formed by MHV E protein, small aliquots of solutions containing the compounds were added to the aqueous solutions bathing planar lipids in which the peptide channel activity had been reconstituted and the effect of the compound addition on the ionic currents was recorded and measured.

Compound stock solutions were typically prepared at 500 mM in DMSO. This solution was further diluted to 50 mM, or lower concentration in 50% DMSO/50% methanol and 2 μl of the appropriately diluted compound was added to the cis and/or trans chambers to yield the desired final concentration.

Figure 12A:
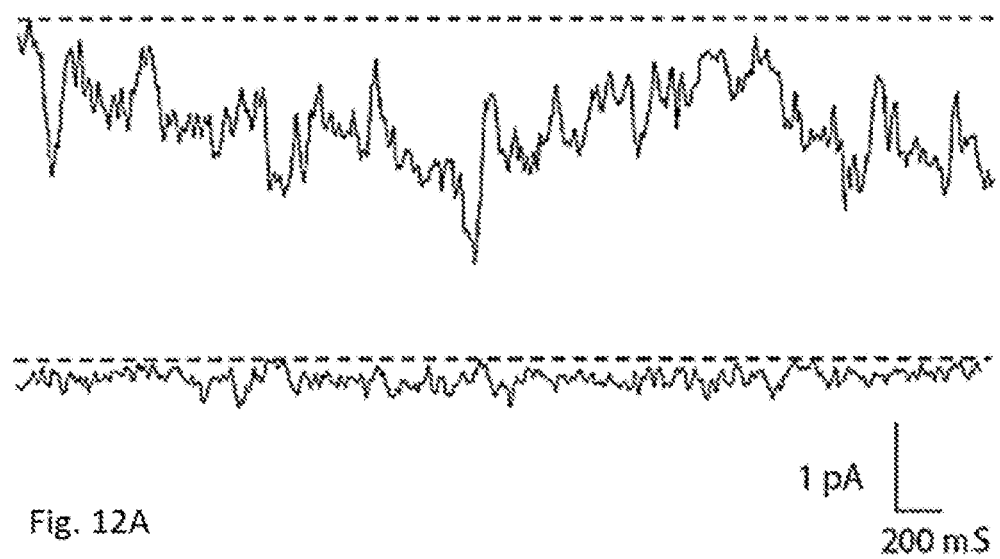
FIG. 12A-B: Part 12A shows raw currents generated by the MHV-E protein ion channel in a planar lipid bilayer. The top trace shows current activity prior to drug addition and the lower trace shows the effect of addition of 100 μM cinnamoylguanidine on channel activity. Part 12B is a graphical representation of the average current flowing across the bilayer (in arbitrary units), before and after addition of cinnamoylguanidine.
Figure 12B:
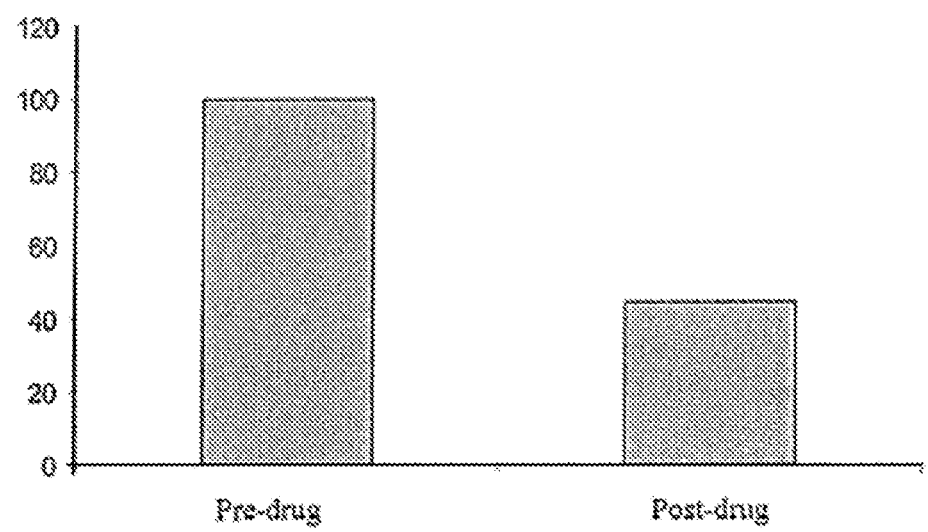

In the example shown in FIG. 12 below, addition of 100 μM cinnamoylguanidine to the cis chamber greatly reduced current flow through the MHV E ion channel.

EXAMPLE 37

Bacterial Bio-Assay for Screening Potential MHV E-Protein Ion Channel-Blocking Drugs MHV E-protein Ion Channel Inhibits Bacterial Cell Growth.

A bio-assay of MHV E-protein function in bacterial cells was developed. A synthetic cDNA fragment encoding MHV E-protein was cloned into the expression plasmid pPL451, creating a vector in which E protein expression is temperature inducible, as described in Example 4. Inhibition of the growth of *E.coli* cells expressing E protein at 37° C. was observed as an indicator of p7 ion channel function dissipating the normal Na+ gradient maintained by the bacterial cells.

EXAMPLE 38

Compound Screening Using the Bacterial Bio-Assay for MHV E Protein

The halos of growth around the site of application of particular drugs—as described in example 14—were scored as described in example 15.

Table 12 lists the scores for inhibition of MHV E protein in the bacterial bio-assay.

TABLE 12

| Compound | MHV E protein Inhibition (score) |
|---|---|
| 4-isopropylcinnamoylguanidine | 4.5 |
| 3-isopropylcinnamoylguanidine hydrochloride | 4.2 |
| 4-t-butylcinnamoylguanidine | 4.1 |
| 3-(trifluoromethoxy)cinnamoylguanidine | 4.1 |
| 3-t-butylcinnamoylguanidine | 4.0 |
| 3,4-dichlorocinnamoylguanidine | 3.8 |
| 2,3-difluorocinnamoylguanidine | 3.8 |
| 2-t-butylcinnamoylguanidine | 3.8 |
| 3-phenylcinnamoylguanidine | 3.7 |
| 2-phenylcinnamoylguanidine | 3.4 |
| 5-bromo-2-methoxycinnamoylguanidine | 3.3 |
| 2-(cyclohex-1-en-1yl)cinnamoylguanidine | 3.3 |
| 3-(trifluoromethyl)cinnamoylguanidine | 2.9 |
| 3-(cyclohex-1-en-1-yl)cinnamoylguanidine | 2.9 |
| trans-3-(1-napthyl)acryloylguanidine | 2.8 |
| 4-(trifluoromethyl)cinnamoylguanidine | 2.8 |
| 3-(2-napthyl)acryloylguanidine | 2.8 |
| 2-(trifluoromethyl)cinnamoylguanidine | 2.7 |
| (4-Phenoxybenzoyl)guanidine | 2.4 |
| (3-Bromocinnamoyl)guanidine | 2.4 |
| 2,5-dimethylcinnamoylguanidine | 2.3 |
| 5-bromo-2-fluorocinnamoylguanidine | 2.1 |
| 6-methoxy-2-naphthoylguanidine | 1.8 |
| 4-phenylbenzoylguanidine | 1.8 |
| (4-Bromocinnamoyl)guanidine | 1.8 |
| 1-napthoylguanidine | 1.7 |
| (5-Phenyl-penta-2,4-dienoyl)guanidine | 1.4 |
| (2-Bromocinnamoyl)guanidine | 1.4 |
| (4-Chlorocinnamoyl)guanidine | 1.3 |
| 2-methylcinnamoylguanidine | 1.2 |
| 2,6-dichlorocinnamoylguanidine | 1.2 |
| 2,4,6-trimethylcinnamoylguanidine | 1.2 |
| 5-(N,N-hexamethylene)amiloride | 1.1 |
| cinnamoylguanidine | 1.1 |
| cinnamoylguanidine hydrochloride | 1.1 |
| (a-Methylcinnamoyl)guanidine | 1.0 |
| 2,3-dimethylcinnamoylguanidine | 1.0 |
| 2-cyclohexylcinnamoylguanidine | 0.9 |
| N-(3-phenylpropanoyl)-N'-phenylguanidine | 0.8 |
| N,N'-bis(3phenylpropanoyl)-N''-phenylguanidine | 0.8 |
| (3-Methoxycinnamoyl)guanidine | 0.8 |
| (2-Methoxycinnamoyl)guanidine | 0.8 |
| 3-fluorocinnamoylguanidine | 0.8 |
| 2-fluorocinnamoylguanidine | 0.8 |
| 2,4-dichlorocinnamolyguanidine | 0.8 |
| 2-ethylcinnamoylguanidine | 0.8 |
| (2-Chlorocinnamoyl)guanidine | 0.7 |
| (4-Hydroxycinnamoyl)guanidine | 0.7 |
| 2-ethoxycinnamoylguanidine | 0.7 |
| 2-napthoylguanidine | 0.6 |
| (trans-2-Phenylcyclopropanecarbonyl)guanidine | 0.6 |
| 5-(N,N-Dimethyl)amiloride hydrochloride | 0.5 |
| 5-(4-fluorophenyl)amiloride | 0.5 |
| 3-methylcinnamoylguanidine | 0.5 |
| (3-Chlorocinnamoyl)guanidine | 0.4 |
| 4-methylcinnamoylguanidine | 0.4 |
| 4-ethoxycinnamoylguanidine | 0.4 |
| 2-(1-napthyl)acetoylguanidine | 0.4 |
| 3,4-difluorocinnamoylguanidine | 0.4 |
| 2-(2-napthyl)acetoylguanidine | 0.4 |
| 2,3,5,6,-tetramethylcinnamoylguanidine | 0.4 |
| (4-Methoxycinnamoyl)guanidine | 0.3 |
| 3,4-(methylenedioxy)cinnamoylguanidine | 0.3 |
| 3-ethoxycinnamoylguanidine | 0.3 |
| 4-fluorocinnamoylguanidine | 0.2 |
| 1-bromo-2-napthoylguanidine | 0.2 |
| 5-tert-butylamino-amiloride | 0.1 |
| (3-Nitrocinnamoyl)guanidine | 0.1 |
| 3,4,5-trimethoxycinnamoylguanidine | 0.1 |
| 5-(3'-bromophenyl)penta-2,4-dienoylguanidine | 0.1 |

EXAMPLE 39

MHV Antiviral Assay for Testing Compounds Against Replication of Mouse Hepatitis Virus (MHV)

To determine the antiviral activity of compounds against MHV replication (strain MHV-A59: ATCC VR-764), an assay measuring reduction in the number of plaques formed in monolayers of MHV infected L929 cells (ATCC CCL-a) was developed: First, a virus working stock was prepared by amplification in NCTC clone 1469 cells (ATCC CCL-9.1). This was then used to infect confluent monolayers of L929 cells grown in 6-well tissue culture plates by exposure to the virus at an MOI of 0.01 pfu/cell or 1 pfu/cell for 30 minutes at 37° C. in 5% $CO_2$. The infective inoculum was removed and replaced with fresh medium (DMEM supplemented with 10% horse serum) containing various test concentrations of compounds or the appropriate level of solvent used for the compounds (control). Plates were subsequently incubated at 37° C. (in 5% $CO_2$) for 16-24 hours post infection, after which time culture supernatant was removed and the cells were stained with 0.1% crystal violet solution in 20% ethanol for 10 minutes. Plaques were counted in all wells and the percentage reduction in plaque number compared to solvent control was calculated. Measurements were performed in duplicate to quadruplicate wells.

EXAMPLE 40

Effect of Compounds in MHV Antiviral Assay

Table 13 provides the results obtained from this study.

TABLE 13

| Compound | Percent reduction in Plaque number/# experiments | | |
|---|---|---|---|
| | 20 uM | 10 uM | 1 uM |
| 5-(3'-bromophenyl)penta-2,4-dienoyl-guanidine | N/D | 99/2 | 66/1 |
| 5-bromo-2-methoxycinnamoylguanidine | N/D | 100/1 | 66/1 |
| 3-phenylcinnamoylguanidine | Toxic | 86/2 | 64/3 |
| 2,3-difluorocinnamoylguanidine | Toxic | 92/3 | 64/2 |
| 3-ethoxycinnamoylguanidine | 100/1 | 89/2 | 58/1 |
| 5-(2'-bromophenyl)penta-2,4-dienoyl-guanidine | Toxic | 100/1 | 57/1 |

TABLE 13-continued

| Compound | 20 uM | 10 uM | 1 uM |
|---|---|---|---|
| cinnamoylguanidine hydrochloride | 85/1 | 72/2 | 56/1 |
| (2-Chlorocinnamoyl)guanidine | 95/2 | 88/3 | 53/3 |
| cinnamoylguanidine | 97/8 | 88/8 | 52/7 |
| (4-Bromocinnamoyl)guanidine | Toxic/2 | 98/3 | 52/3 |
| (2-Bromocinnamoyl)guanidine | 91/2 | 89/3 | 52/3 |
| (4-Methoxycinnamoyl)guanidine | 98/4 | 96/4 | 51/3 |
| (a-Methylcinnamoyl)guanidine | 81/2 | 75/3 | 51/2 |
| 3,4-dichlorocinnamoylguanidine | 91/2 | 96/1 | 50/2 |
| 2-(cyclohex-1-en-1yl)cinnamoylguanidine | N/D | 97/1 | 50/1 |
| 3,4-difluorocinnamoylguanidine | Toxic | 91/2 | 50/1 |
| 3-t-butylcinnamoylguanidine | Toxic | 94/3 | 49/2 |
| 2-ethoxycinnamoylguanidine | 93/2 | 85/3 | 48/2 |
| trans-3-Furanacryoylguanidine | 70/1 | 65/1 | 48/1 |
| N-amidino-3-amino-5-hexamethyleneimino-6-phenyl-2-pyrazinecarboxamide | 84/1 | 52/2 | 48/1 |
| (2-Nitrocinnamoyl)guanidine | 97/1 | 77/2 | 47/1 |
| 4-(trifluoromethyl)cinnamoylguanidine | 97/3 | 95/3 | 46/3 |
| 3,4-(methylenedioxy)cinnamoylguanidine | 93/3 | 82/3 | 45/3 |
| 5-(N-Methyl-N-isobutyl)amiloride | 92/1 | 85/1 | 44/2 |
| (4-Chlorocinnamoyl)guanidine | 97/2 | 88/2 | 43/3 |
| 2,4-dichlorocinnamolyguanidine | 76/1 | 73/1 | 43/1 |
| N-(3-phenylpropanoyl)-N'-phenylguanidine | 80/1 | 65/1 | 43/1 |
| (3-Nitrocinnamoyl)guanidine | 95/2 | 77/3 | 42/3 |
| 2-phenylcinnamoylguanidine | N/D | 100/1 | 42/1 |
| 4-isopropylcinnamoylguanidine | 95/3 | 93/3 | 41/3 |
| 3-(trifluoromethoxy)cinnamoylguanidine | 100/1 | 90/3 | 41/2 |
| 3-(trifluoromethyl)cinnamoylguanidine | 98/1 | 83/1 | 40/1 |
| (4-Nitrocinnamoyl)guanidine | 97/1 | 75/3 | 40/3 |
| 3-(2-napthyl)acryloylguanidine | 93/1 | 93/1 | 40/1 |
| 4-ethoxycinnamoylguanidine | 96/1 | 92/1 | 40/1 |
| 2,6-dichlorocinnamoylguanidine | 91/1 | 70/1 | 40/1 |
| 2,5-dimethylcinnamoylguanidine | 95/3 | 91/3 | 39/3 |
| (3-Bromocinnamoyl)guanidine | 95/2 | 90/3 | 39/3 |
| (3-Chlorocinnamoyl)guanidine | 94/1 | 86/2 | 39/2 |
| 3-methylcinnamoylguanidine | 90/1 | 88/1 | 39/1 |
| (3-Methoxycinnamoyl)guanidine | 92/2 | 87/2 | 37/3 |
| 2-t-butylcinnamoylguanidine | N/D | 98/2 | 37/1 |
| [(E)-3-(4-Dimethylaminophenyl)-2-methylacryloyl]guanidine | 56/1 | 45/1 | 37/1 |
| N,N'-bis(1-napthoyl)guanidine | 58/1 | 52/2 | 35/1 |
| 3-methoxy-HMA | 15/1 | 31/1 | 35/1 |
| 5-tert-butylamino-amiloride | 89/4 | 84/4 | 34/4 |
| trans-3-(1-napthyl)acryloylguanidine | 95/2 | 86/3 | 34/3 |
| 6-methoxy-2-naphthoylguanidine | 88/3 | 56/3 | 34/3 |
| 2-napthoylguanidine | 67/2 | 36/2 | 34/2 |
| 2-ethylcinnamoylguanidine | 96/1 | 81/2 | 34/1 |
| 2,3-dimethylcinnamoylguanidine | 95/1 | 79/2 | 34/1 |
| N''-Cinnamoyl-N,N'-diphenylguanidine | 97/1 | 72/2 | 34/1 |
| 3-isopropylcinnamoylguanidine hydrochloride | N/D | 99/2 | 32/1 |
| (4-Phenoxybenzoyl)guanidine | 73/1 | 65/1 | 32/1 |
| (trans-2-Phenylcyclopropanecarbonyl)-guanidine | 77/2 | 64/2 | 31/2 |
| 3-fluorocinnamoylguanidine | 100/1 | 93/2 | 31/1 |
| 5-bromo-2-fluorocinnamoylguanidine | Toxic | 81/2 | 31/1 |
| N,N'-bis-(cinnamoyl)-N''-phenylguanidine | 16/1 | 38/2 | 31/1 |
| 3-quinolinoylguanidine | 27/1 | 36/2 | 30/1 |
| 2,4,6-trimethylcinnamoylguanidine | 91/2 | 61/3 | 27/2 |
| 1-bromo-2-napthoylguanidine | 31/1 | 27/2 | 27/1 |
| N-amidino-3,5-diamino-6-phynyl-2-pyrazinecarboxamide | 53/1 | 39/2 | 25/1 |
| N-Cinnamoyl-N',N'-dimethylguanidine | 92/2 | 65/3 | 24/2 |
| (2-Methoxycinnamoyl)guanidine | 90/2 | 85/2 | 23/2 |
| 2-(2-napthyl)acetoylguanidine | 52/2 | 20/2 | 23/1 |
| 4-phenylcinnamoylguanidine | 53/1 | 36/1 | 21/3 |
| [3-(3-Pyridyl)acryloyl]guanidine | 81/2 | 73/2 | 21/2 |
| 3,4,5-trimethoxycinnamoylguanidine | 84/1 | 84/1 | 21/1 |
| 4-methylcinnamoylguanidine | 93/1 | 89/1 | 20/1 |
| 4-fluorocinnamoylguanidine | 86/1 | 83/1 | 20/1 |
| 2-methylcinnamoylguanidine | 91/1 | 82/1 | 20/1 |
| 6-bromo-2-napthoylguanidine | 65/1 | 37/2 | 19/1 |
| 5-(N,N-Dimethyl)amiloride hydrochloride | 42/4 | 7/4 | 17/4 |
| (5-Phenyl-penta-2,4-dienoyl)guanidine | 27/1 | 24/1 | 17/1 |
| 2-cyclohexylcinnamoylguanidine | 100/1 | 74/2 | 16/1 |
| 5-(4-fluorophenyl)amiloride | 4/1 | 25/1 | 16/1 |
| Benzyoylguanidine | 22/1 | 39/2 | 14/1 |
| N-Benzoyl-N'-cinnamoylguanidine | 0/1 | 0/1 | 14/1 |
| 5-(N,N-hexamethylene)amiloride | 84/2 | 89/1 | 13/2 |
| N-(cinnamoyl)-N'phenylguanidine | 83/1 | 88/1 | 13/1 |
| (4-Hydroxycinnamoyl)guanidine | 19/1 | 15/1 | 13/1 |
| 2-(trifluoromethyl)cinnamoylguanidine | 19/1 | 15/1 | 13/1 |
| (Quinoline-2-carbonyl)guanidine | 86/1 | 84/1 | 12/1 |
| 2-(1-napthyl)acetoylguanidine | −19/1 | 02/1 | 11/1 |
| 2-chloro-6-fluorocinnamoylguanidine | 100/1 | 84/2 | 9/1 |
| N-amidino-3-amino-5-phenyl-6-chloro-2-pyrazinecarboxamide | 20/1 | 20/2 | 9/1 |
| 4-phenylbenzoylguanidine | 32/1 | 24/1 | 5/1 |
| N,N'-bis(2-napthoyl)guanidine | 5/1 | 3/2 | 3/1 |
| (Phenylacetyl)guanidine | 35/1 | 22/1 | 3/1 |
| 1-napthoylguanidine | 71/3 | 62/3 | 2/3 |
| N,N'-bis(3phenylpropanoyl)-N''-phenyl-guanidine | 67/3 | 40/4 | 1/3 |
| 3-hydroxy-5-hexamethyleneimino-amiloride | 16/1 | 22/2 | 1/1 |
| 2'4 DichloroBenzamil HCl | 12/2 | 0/3 | 0/3 |
| 2,3,5,6,-tetramethylcinnamoylguanidine | N/D | 68/2 | 0/1 |
| Benzamil hydrochloride | 0/1 | 26/1 | 0/1 |
| 6-Iodoamiloride | 28/1 | 21/1 | 0/1 |
| N,N'-Bis(amidino)napthalene-2,6-dicarboxamide | 19/1 | 16/1 | 0/1 |
| [(4-Chlorophenoxy-acetyl]guanidine | 19/1 | 16/1 | 0/1 |
| (3-phenylpropanoyl)guanidine | 51/1 | 03/1 | 0/1 |
| 2-fluorocinnamoylguanidine | 76/1 | 73/1 | |
| 6-bromo-2-napthoylguanidine | | 43/1 | |
| (2-Furanacryloyl)guanidine | 67/2 | 63/2 | −3/2 |
| N-(6-Hydroxy-2-napthoyl)-N'-phenyl-guanidine | 43/1 | 39/1 | −5/1 |
| Amiloride•HCl | 21/1 | 18/1 | −5/1 |
| 3-(trans-hept-1-en-1-yl)cinnamoylguanidine | T/1 | 23(T)/1 | −6/1 |
| 3-methoxy-amiloride | 60/2 | 47/3 | −7/2 |
| N,N'-Bis(3-phenylpropanoyl)guanidine | 41/3 | 30/4 | −8/3 |
| 3-(cyclohex-1-en-1-yl)cinnamoylguanidine | T/1 | 2/2 | −19/1 |

EXAMPLE 41

Porcine Respiratory Coronavirus (PRCV)

Antiviral Assay for Testing Compounds Against Replication of Porcine Respiratory Coronavirus (PRCV)

To determine the antiviral activity of compounds against porcine respiratory coronavirus replication (ATCC VR-2384), an assay measuring reduction in the number of plaques formed in monolayers of PRCV infected ST cells (procine fetal testis cell line, ATCC CRL-1746) was developed: Confluent ST cells in 6 well plates were infected with a quaternary passage of porcine respiratory virus (PRCV) strain AR310 at three dilutions $10^{-1}$, $50^{-1}$ and $10^{-2}$ in PBS to provide a range of plaques numbers to count. 100 ul of diluted virus was added per well in a volume of 1 ml of media. Plates were incubated for one hour on a rocking platform at room temperature to allow virus to adsorb to cells. The viral supernatant was removed and 2 ml/well of overlay containing 1% Seaplaque agarose in 1×MEM, 5% FCS was added to each well. Compounds to be tested were added to the overlay mixture by diluting the compounds from frozen stock to a concentration so that the same volume of compound/solvent would be added to the overlay for each concentration of compound. The volume of compound/solvent never exceeded 0.07% of the volume of the overlay. The solvent used to dissolve compounds was DMSO and methanol mixed in equal proportions. Compounds were tested for anti-plaque forming activity at four concentrations, 0.1 uM, 1 uM, 10 uM and 20 uM. Either duplicates or quadruplicates were performed at each concentration. Controls were performed where the same volume of solvent was added to the overlay. The overlay was allowed to set at room temp for 20 mins. The plates were then incubated at 37° C. for 2 days. The monolayers were then fixed and stained overnight at room temperature by adding 1 ml/well of 0.5% methylene blue, 4% formaldehyde. Overlay agarose and stain was then rinsed off to visualize stained and fixed monolayer

EXAMPLE 42

Effect of Compounds in PRCV Antiviral Assay

Compounds were screened for activity against PRCV replication according to the method described in example 29. Table 14 provides EC50 values for some tested compounds.

TABLE 14

| Compound | EC50 (uM) |
| --- | --- |
| 5-(N,N-hexamethylene)amiloride | 0.06 |
| 6-methoxy-2-naphthoylguanidine | 0.04 |
| cinnamoylguanidine | 0.08 |
| N-(3-phenylpropanoyl)-N'-phenylguanidine | 19 |
| 3-methylcinnamoylguanidine | 1.43 |
| (3-Bromocinnamoyl)guanidine | 11.2 |
| (trans-2-Phenylcyclopropanecarbonyl)guanidine | 17.2 |
| trans-3-(1-napthyl)acryloylguanidine | 19.1 |
| 2-(2-napthyl)acetoylguanidine | 119.6 |

EXAMPLE 43

Bovine Coronavirus

Antiviral Assay for Testing Compounds Against Replication of Bovine Coronavirus (BCV).

To determine the antiviral activity of compounds against bovine coronavirus replication (ATCC VR-874), an assay measuring reduction in the number of plaques formed in monolayers of BCV infected MDBK cells (bovine kidney cell line; ATCC CCL-22) was developed: Confluent MDBK cells in 6 well plates were infected with a secondary passage of BCV with serially diluted virus diluted to $10^{-3}$, $5^{-5}$ and $10^{-4}$ in PBS to provide a range of plaques numbers to count. 100 ul of diluted virus was added per well in a volume of 1 ml of media. Plates were incubated for one hr to allow virus to adsorb to cells. The viral supernatant was removed and 2 ml/well of overlay containing 1% Seaplaque agarose in 1×MEM, 5% FCS was added to each well. Compounds to be tested were added to the overlay mixture by diluting the compounds from a 0.5M frozen stock to a concentration so that the same volume of compound/solvent would be added to the overlay for each concentration of compound. The volume of compound/solvent never exceeded 0.07% of the volume of the overlay. The solvent used to dissolve compounds was DMSO and methanol mixed in equal proportions. Compounds were tested for anti-plaque forming activity at four concentrations, 0.1 uM, 1 uM, 10 uM and 20 uM. Quadruplicates were performed at each concentration. Controls were performed where the same volume of solvent was added to the overlay. The overlay was allowed to set at room temp for 20 mins. The plates were then incubated at 37° C. for 7 days. The monolayers were then fixed and stained by adding 1 ml/well of 0.5% methylene blue, 4% formaldehyde.

EXAMPLE 44

Effect of Compounds in BCV Antiviral Assay

Compounds were screened for activity against BCV replication according to the method described in example 31. Table 15 provides EC50 values for some tested compounds.

TABLE 15

| Compound | EC50 uM |
|---|---|
| (3-Bromocinnamoyl)guanidine | 3 |
| 3-(trifluoromethyl)cinnamoylguanidine | 3 |
| 6-methoxy-2-naphthoylguanidine | 9 |
| 5-(N,N-hexamethylene)amiloride | 9 |
| trans-3-(1-napthyl)acryloylguanidine | 13 |
| cinnamoylguanidine | 42 |
| (5-Phenyl-penta-2,4-dienoyl)guanidine | 95 |
| 2-(2-napthyl)acetoylguanidine | 99 |
| (trans-2-Phenylcyclopropanecarbonyl)guanidine | 109 |
| N-(3-phenylpropanoyl)-N'-phenylguanidine | 156 |
| 4-phenylbenzoylguanidine | 190 |

EXAMPLE 45

Hepatitis C Virus

Ion Channel Activity of Hepatitis C Virus P7 Protein

Testing of a Synthetic P7 Peptide for channel activity in artificial lipid bilayers 1. A peptide mimicking the protein P7 encoded by the hepatitis C virus (HCV) was synthesised having the following amino acid sequence:

```
                                        (SEQ ID NO: 8)
ALENLVILNAASLAGTHGLVSFLVFFCFAWYLKGRWVPGAVYAFYGMW

PLLLLLLALPQRAYA
```

Lipid bilayer studies were performed as described elsewhere (Miller, 1986). A lipid mixture of palmitoyl-oleoyl-phosphatidylethanolamine, palmitoyl-oleoyl-phosphatidylserine and palmitoyl-oleoyl-phosphatidylcholine (5:3:2) (Avanti Polar Lipids, Alabaster, Ala.) was used. The lipid mixture was painted onto an aperture of 150-200 um in the wall of a 1 ml delrin cup. The aperture separates two chambers, cis and trans, both containing salt solutions at different concentrations. The cis chamber was connected to ground and the trans chamber to the input of an Axopatch 200 amplifier. Normally the cis chamber contained 500 mM KCl and the trans 50 mM KCl. The bilayer formation was monitored electrically by the amplitude of the current pulse generated by a current ramp. The potentials were measured in the trans chamber with respect to the cis. The protein was added to the cis chamber and stirred until channel activity was seen. The currents were filtered at 1000 Hz, digitized at 2000 Hz and stored on magnetic disk. The P7 peptide was dissolved in 2,2,2-trifluorethanol (TFE) at 10 mg/ml. 10 ul of this was added to the cis chamber of the bilayer which was stirred. Channel activity was seen within 15-20 min.

When the P7 peptide was added to the cis chamber and stirred, channel activity was recorded. The potential in the trans chamber was −80 mV and the currents are downwards. The currents reversed at +50 mV close to the potassium equilibrium potential in these solutions indicating that the channels were cation-selective. The amplitude of the open-channel peak is 1.7 pA corresponding to a channel conductance of about 14 pS. In most experiments, "single channels" had a much larger size, presumably because of aggregation of the P7 peptide. The currents reversed at about +40 mV in this experiment. In some experiments the solution in the cis chamber was 150 mM KCl and 15 mM KCl in the trans chamber. The P7 peptide again produced currents that reversed.

Similar results were obtained when both chambers contained NaCl. Currents recorded in an experiment when the cis chamber contained 500 mM NaCl and the trans chamber 50 mM NaCl. Again the currents reversed between +40 and +60 mV, close to the Na$^+$ equilibrium potential indicating that channels were much more permeable to Na$^+$ than to K$^+$.

The channels formed by the P7 peptide were blocked by 5-(N,N-hexamethylene) amiloride (HMA).

Addition of the P7 peptide produced channel activity. Addition of 2 µl of 50 µM HMA to the cis chamber followed by stirring resulted in disappearance of the channel activity. Block of channel activity produced by the P7 peptide with 100 µM HMA was recorded in 4 experiments. In 2 experiments, sodium channels (500/50) were blocked by 500 µM HMA When 10 mM CaCl$_2$ was added to the cis chamber (K solutions) the reversal potential of the currents produced by P7 peptide shifted to more negative potentials indicating a decrease in the P$_K$/P$_{Cl}$ ratio.

When the cis chamber contained 500 mM CaCl$_2$ and the trans chamber 50 mM CaCl$_2$, both positive and negative currents were seen at potentials around +20 mV and it was not possible to determine a reversal potential.

EXAMPLE 46

Recombinant Expression of HCV p7 Protein

Two cDNA fragments, each encoding the same polypeptide corresponding to the amino acid sequence of the HCV-1a p7 protein, were synthesised commercially by GeneScript. The two cDNAs differed in nucleotide sequence such that in one cDNA ("cDp7.coli") the codons were optimised for expression of the p7 protein in *E.coli* while in the other cDNA ("cDp7.mam") codons were biased for expression in mammalian cell lines. cDp7.coli was cloned into the plasmid pPL451 as a BamHI/EcoRI fragment for expression in *E.coli*. cDp7.mam was cloned into vectors (for example, pcDNA3.1 vaccinia virus, pfastBac-1) for expression of p7 in mammalian cell lines.

EXAMPLE 47

Role of p7 in Enhancement of Gat VLP Budding

The budding of virus-like particles (VLP) from cultured HeLa cells results from the expression of retroviral Gag proteins in the cells and co-expression of small viral ion channels, such as M2, Vpu and 6K, with the Gag protein enhances budding. Interestingly, the viral ion channels can enhance budding of heterologous virus particles. Therefore, to assess budding enhancement by p7 it was co-expressed with the HIV-1 Gag protein in HeLa cells, and VLP release into the culture medium was measured by Gag ELISA. To achieve this, the plasmids pcDNAp7 (pc DNA3.1=pcDp7.mam as described in Example 20, p7 expressed under control of the T7 promoter) and pcDNA-Gag (HIV-1 Gag protein expressed under control of the T7 promoter) were cotransfected into HeLa cells infected with the vaccinia virus strain vTF7.3 (expresses T7 RNA polymerase) and culture supernatants were collected for ELISA assay after 16 hours incubation.

EXAMPLE 48

Assay of the Ability of Compounds to Inhibit p7 Ion Channel Functional Activity

The two methods of detecting p7 ion channel functional activity, described in Examples 33-35, were employed to assay the ability of compounds to inhibit the p7 channel. In the case of Example 33, compounds were tested for their ability to inhibit p7 channel activity in planar lipid bilayers. In the case of Example 35 compounds were tested for their ability to reduce the number of VLPs released from cells expressing both p7 and HIV-1 Gag.

EXAMPLE 49

Bacterial Bio-Assay for Screening Potential HCV p7 Protein Ion Channel-Blocking Drugs.

HCV p7 Ion Channel Inhibits Bacterial Cell Growth.

A bio-assay of p7 function in bacterial cells was developed. The p7-encoding synthetic cDNA fragment cDp7.coli was cloned into the expression plasmid pPL451, creating the vector pPLp7, in which p7 expression is temperature inducible, as described in Example 4. Inhibition of the growth of *E.coli* cells expressing p7 at 37° C. was observed as an indicator of p7 ion channel function dissipating the normal Na+ gradient maintained by the bacterial cells.

EXAMPLE 50

Compound Screening Using the Bacterial Bio-Assay for HCV p7 Protein

The halos of growth around the site of application of particular drugs—as described in example 14—were scored as described in example 15.

Table 16 lists the scores for inhibition of HCV p7 protein in the bacterial bio-assay.

TABLE 16

| Compound | HCV p7 protein Inhibition (score/# of times tested) |
| --- | --- |
| 2,3-dimethylcinnamoylguanidine | 3.88/2 |
| 2,4,6-trimethylcinnamoylguanidine | 3.75/1 |
| 5-bromo-2-fluorocinnamoylguanidine | 3.73/6 |
| (4-Bromocinnamoyl)guanidine | 3.47/4 |
| 2,5-dimethylcinnamoylguanidine | 3.43/4 |
| 3-(trifluoromethyl)cinnamoylguanidine | 3.34/3 |
| 4-(trifluoromethyl)cinnamoylguanidine | 3.33/5 |
| 6-methoxy-2-naphthoylguanidine | 3.33/3 |
| (2-Chlorocinnamoyl)guanidine | 3.31/6 |
| (4-Chlorocinnamoyl)guanidine | 3.16/4 |
| (2-Bromocinnamoyl)guanidine | 3.00/3 |
| 2,6-dichlorocinnamoylguanidine | 3.00/3 |
| (3-Bromocinnamoyl)guanidine | 2.92/3 |
| (3-Chlorocinnamoyl)guanidine | 2.75/3 |
| 2-(trifluoromethyl)cinnamoylguanidine | 2.63/3 |
| (4-Phenoxybenzoyl)guanidine | 2.63/1 |
| 3,4-dichlorocinnamoylguanidine | 2.59/3 |
| 4-isopropylcinnamoylguanidine | 2.51/2 |
| trans-3-(1-napthyl)acryloylguanidine | 2.44/2 |
| 4-t-butylcinnamoylguanidine | 2.42/2 |

TABLE 16-continued

| Compound | HCV p7 protein Inhibition (score/# of times tested) |
|---|---|
| 2-t-butylcinnamoylguanidine | 2.36/2 |
| 2-ethylcinnamoylguanidine | 2.36/2 |
| 4-methylcinnamoylguanidine | 2.32/2 |
| 5-bromo-2-methoxycinnamoylguanidine | 2.32/2 |
| 3-(trifluoromethoxy)cinnamoylguanidine | 2.26/2 |
| 2-cyclohexylcinnamoylguanidine | 2.26/2 |
| 1-napthoylguanidine | 2.25/1 |
| 3-t-butylcinnamoylguanidine | 2.23/2 |
| 4-phenylbenzoylguanidine | 2.19/2 |
| (5-Phenyl-penta-2,4-dienoyl)guanidine | 2.13/1 |
| N-(cinnamoyl)-N'phenylguanidine | 2.13/1 |
| 3-isopropylcinnamoylguanidine hydrochloride | 2.00/1 |
| Benzamil hydrochloride | 2.0/1 |
| N-(3-phenylpropanoyl)-N'-phenylguanidine | 2.0/1 |
| N,N'-bis(3phenylpropanoyl)-N''-phenylguanidine | 2.0/1 |
| 3-(2-napthyl)acryloylguanidine | 1.93/2 |
| 5-(N-Methyl-N-isobutyl)amiloride | 1.88/1 |
| 2'4 DichloroBenzamil HCl | 1.88/1 |
| 5-tert-butylamino-amiloride | 1.88/1 |
| 5-(N-Ethyl-N-isopropyl)amiloride | 1.88/1 |
| (4-Methoxycinnamoyl)guanidine | 1.88/1 |
| 4-fluorocinnamoylguanidine | 1.86/1 |
| (3-Nitrocinnamoyl)guanidine | 1.71/1 |
| 4-ethoxycinnamoylguanidine | 1.63/1 |
| (4-Hydroxycinnamoyl)guanidine | 1.63/1 |
| (trans-2-Phenylcyclopropanecarbonyl)guanidine | 1.63/1 |
| 3-ethoxycinnamoylguanidine | 1.63/1 |
| 2,3,5,6,-tetramethylcinnamoylguanidine | 1.51/2 |
| 4-phenylcinnamoylguanidine | 1.5/1 |
| trans-3-Furanacryoylguanidine | 1.38/1 |
| N-(6-Hydroxy-2-napthoyl)-N'-phenylguanidine | 1.38/1 |
| (2-Furanacryloyl)guanidine | 1.38/1 |
| 3-(cyclohex-1-en-1-yl)cinnamoylguanidine | 1.32/2 |
| cinnamoylguanidine hydrochloride | 1.32/2 |
| 5-(N,N-hexamethylene)amiloride | 1.28/4 |
| 2,3-difluorocinnamoylguanidine | 1.24/1 |
| 2-(1-napthyl)acetoylguanidine | 1.14/1 |
| (a-Methylcinnamoyl)guanidine | 1.14/1 |
| (2-Nitrocinnamoyl)guanidine | 1.14/1 |
| 6-Iodoamiloride | 1.13/1 |
| 3,4-(methylenedioxy)cinnamoylguanidine | 1.13/1 |
| 2-ethoxycinnamoylguanidine | 1.00/1 |
| cinnamoylguanidine | 1.00/1 |
| 2-phenylcinnamoylguanidine | 1.00/1 |
| 2-(cyclohex-1-en-1yl)cinnamoylguanidine | 1.00/1 |
| 2-napthoylguanidine | 1.0/3 |
| 3-phenylcinnamoylguanidine | 1.0/1 |
| 5-(N,N-Dimethyl)amiloride hydrochloride | 1.0/1 |
| 5-(4-fluorophenyl)amiloride | 1.0/1 |
| (3-Methoxycinnamoyl)guanidine | 1.0/1 |
| 2-fluorocinnamoylguanidine | 1.0/1 |
| 5-(3'-bromophenyl)penta-2,4-dienoylguanidine | 1.0/1 |
| [(4-Chlorophenoxy-acetyl]guanidine | 1.0/1 |
| (3-phenylpropanoyl)guanidine | 1.0/1 |
| 2-chloro-6-fluorocinnamoylguanidine | 0.88/1 |
| 3-fluorocinnamoylguanidine | 0.86/1 |
| 2-methylcinnamoylguanidine | 0.75/1 |
| (2-Methoxycinnamoyl)guanidine | 0.75/1 |
| 1-bromo-2-napthoylguanidine | 0.75/1 |
| 3,4,5-trimethoxycinnamoylguanidine | 0.71/1 |
| 3-methylcinnamoylguanidine | 0.63/1 |
| 3-(trans-hept-1-en-1-yl)cinnamoylguanidine | 0.50/1 |
| Amiloride•HCl | 0.5/2 |
| Phenamil methanesulfonate salt | 0.5/1 |
| 2,4-dichlorocinnamolyguanidine | 0.38/1 |
| (4-Nitrocinnamoyl)guanidine | 0.25/1 |
| 3,4-difluorocinnamoylguanidine | 0.13/1 |
| [(E)-3-(4-Dimethylaminophenyl)-2-methylacryloyl]guanidine | 0.03/4 |

EXAMPLE 51

Equine Arteritis Virus (EAV)

Antiviral Assay for Testing Compounds Against Replication of Equine Arteritis Virus (EAV).

To determine the antiviral activity of compounds against EAV replication (strain Bucyrus; ATCC VR-796), an assay measuring reduction in the number of plaques formed in monolayers of EAV infected BHK-21 cells (ATCC CCL-10) was developed: A virus stock was amplified in RK-13 cells (ATCC CCL-37) and this was then used to infect confluent monolayers of BHK-21 cells grown in 6-well tissue culture plates by exposure to the virus at an MOI of $5 \times 10^{-3}$ pfu/cell for 1 hour at 37° C. 5% $CO_2$. The infective inoculum was removed and the cells were overlayed with a 1% sea plaque overlay (Cambrex Bio Science) in MEM containing 10% FCS containing and 10, 5 or 1 μM of compounds to be tested or the appropriate level of solvent used for the compounds (control). Plates were subsequently incubated at 37° C. (in 5% $CO_2$) for 3 days post infection, after which time culture supernatant was removed and the cells were stained with 0.1% crystal violet solution in 20% ethanol for 10 minutes. Plaques were counted in all wells and the percentage reduction in plaque number compared to solvent control was calculated. Measurements were performed in duplicate to quadruplicate wells.

EXAMPLE 52

Effect of Compounds in EAV Antiviral Assay

Compounds were screened for activity against EAV replication according to the method described in example 35. Results expressed as IC50 values are shown in Table 17.

TABLE 17

| Compound | IC50 |
|---|---|
| 5-(N,N-hexamethylene)amiloride | 7.5 μM |
| (3-Bromocinnamoyl)guanidine | 10 μM |
| trans-3-(1-napthyl)acryloylguanidine | 7.5 μM |
| 2-t-butylcinnamoylguanidine | 1 μM |
| 2-(cyclohex-1-en-1yl)cinnamoylguanidine | 10 μM |

EXAMPLE 53

Dengue Flavivirus

Peptide Synthesis of Dengue Virus M Protein

The C-terminal 40 amino acids of the M protein of the Dengue virus type 1 strain Singapore S275/90 (Fu et al 1992) (ALRHPGFTVIALFLAHAIGTSITQKGIIFILL-MLVTPSMA) (SEQ ID NO: 9) was synthesised using the Fmoc method. The synthesis was done on a Symphony Peptide Synthesiser form Protein Technologies Inc (Tucson, Ariz.) as used to give C-terminal amides, the coupling was done with HBTU and hydroxybenzotriazole in N-methylpyrrolidone. Each of the synthesis cycle used double coupling and a 4-fold excess of the amino acids. Temporary α-N Fmoc-protecting groups were removed using 20% piperidine in DMF.

EXAMPLE 54

Incorporation of Dengue M Virus Protein into Lipid Bilayers

Lipid bilayer studies were performed as described elsewhere (Sunstrom, 1996; Miller, 1986). A lipid mixture of palmitoyl-oleoyl-phosphatidyl-ethanolamine, palmitoyl-oleoyl-phosphatidylserine and palmitoyl-oleoyl-phosphatidylcholine (5:3:2) (Avanti Polar Lipids, Alabaster, Ala.) was used. The lipid mixture was painted onto an aperture of 150-200 μm in the wall of a 1 ml delrin cup. The aperture separates two chambers, cis and trans, both containing salt solutions at different concentrations. The cis chamber was connected to ground and the trans chamber to the input of an Axopatch 200 amplifier. Normally the cis chamber contained 500 mM KCl and the trans 50 mM KCl. The bilayer formation was monitored electrically by the amplitude of the current pulse generated by a current ramp. The potentials were measured in the trans chamber with respect to the cis. The protein was added to the cis chamber and stirred until channel activity was seen. The currents were filtered at 1000 Hz, digitized at 5000 Hz and stored on magnetic disk.

The dengue virus M protein C-terminal peptide (DMVC) was dissolved in 2,2,2-trifluorethanol (TFE) at 0.05 mg/ml to 1 mg/ml. 10 μl of this was added to the cis chamber of the bilayer which was stirred. Channel activity was seen within 15-30 min.

EXAMPLE 55

Hexamethylene Amiloride (HMA) to Inhibits Ion Channel Activity of the Dengue Virus M Protein C-Terminal Peptide Solutions of 50 mM HMA were prepared by first making a 500 mM solution in DMSO. This solution was further diluted to 50 mM HMA using 0.1 M HCl. 2 μl of the 50 mM HMA was added to the cis chamber after channel activity was seen. The cis chamber contained 1 ml of solution making the final concentration of HMA 100 μM.

EXAMPLE 56

Antiviral Assay for Testing Compounds Against Effects of Dengue Flavivirus Against Cytoproliferation Compounds were tested at 10, 5, 2.5, 1.25 and 0.625 μM for activity against Dengue 1 strain Hawaii using a cytoproliferation assay which measures the effect of dengue virus infection on proliferation of LLC-MK2, rhesus macaque monkey kidney cells. The LLC-MK2 cells were infected with a predetermined amount of virus, titrated such that cell proliferation in infected cultures would be significantly reduced compared to uninfected controls. The infected cells were then plated at $1.5\times10^3$ cells per well in a 96 well plate. Negative controls (no virus, no experimental compound), positive controls (virus, no experimental compound), and cytotoxicity controls (experimental compound, no virus) were run with each drug assay. The cultures were allowed to grow for 7 days and then Alamar Blue, a fluorescent dye that measures the metabolism of the cultures (red/ox), was added to each culture and the fluorescence value for each culture was measured. The negative control without experimental compound or virus was fixed at 100%. The positive controls and the cultures with compound were scored by calculating their average fluorescence as a percentage of the negative control. At least six replicate wells were measured for each experimental condition.

EXAMPLE 57

Effect of Compounds in Dengue Antiviral Assay

TABLE 18

| Drug | Drug Conc. μM | Antiviral Percent of Negative Control |
|---|---|---|
| cinnamoylguanidine | | |
| Negative control | 0 | NA |
| Positive control | 0 | 76.5% |
| | 10 | 17.1% |
| | 5 | 38.6% |
| | 2.5. | 58.3% |
| | 1.25 | 72.6% |
| | 0.625 | 76.6% |
| (2-chlorocinnamoyl)guanidine | | |
| Negative control | 0 | NA |
| Positive control | 0 | 80.3% |
| | 10 | 8.4% |
| | 5 | 7.7% |
| | 2.5. | 22.7% |
| | 1.25 | 52.5% |
| | 0.625 | 64.3% |
| Trans-3-(1-naphthyl)acryloylguanidine | | |
| Negative control | 0 | NA |
| Positive control | 0 | 80.4% |
| | 10 | 6.8% |
| | 5 | 12.4% |
| | 2.5. | 38.7% |
| | 1.25 | 73.7% |
| | 0.625 | 77.7% |

N.A.—not applicable

EXAMPLE 58

Positive Correlation Between Bacterial Assay and Anti-Viral Assays

EXAMPLE 58.1

Positive Correlation Between Vpu Bacterial Assay and Anti-HIV-1 Data

A correlative study was performed to measure correlation between the activity scores assigned to compounds tested in the Vpu bacterial assay and the ability of these compounds to inhibit HIV-1 in the anti-viral assay.

EXAMPLE 58.2

Methodology

The p24-antigen data for twelve compounds representing various substituted acylguanidines was compared with the activity scores obtained for those compounds in the Vpu bacterial assay. The data from each assay was initially rank ordered for effectiveness. The rank order for the Vpu bacterial assay was determined from all activity scores, the highest score indicating the greatest effectiveness. The rank order for the anti-HIV-1 assay was determined based on the overall average value of p24 antigen measured in culture supernatants at all of the drug concentrations tested, with the lowest score indicating the greatest effectiveness. The two rank orders generated were then compared statistically by generating the Spearman's Rank correlation coefficient.

EXAMPLE 58.3

Results and Conclusion

The Spearman's correlation coefficient was 0.785 which, by comparison with a statistical table of critical values (for n=12), indicates that the two rank orders are significantly positively correlated (P<0.01) (Table 19a).

In addition, a different comparison of the Vpu Bacterial assay rank order with a yes/no score for whether the anti-viral data indicated a p24 reduction of at least one order of magnitude, aligned the 'yes' group of compounds with the top 6 compounds by the bacterial assay (Table 19b).

These results are indicative that a positive correlation exists between bacterial assays and the antiviral assays as performed according to the present invention. The bacterial assay may therefore be a useful tool in screening for compounds that exhibit anti-viral activity.

TABLE 19a

Comparison of Rank order of efficacy of 12 substituted acyl-guanidines in the Vpu bacterial assay and anti-HIV assay.

| Compound | Bacterial assay rank order | p24 rank order | $di^2$ |
|---|---|---|---|
| (3-bromocinnamoyl)guanidine | 1 | 1 | 0 |
| 3-(trifluoromethyl)cinnamoylguanidine | 2 | 2 | 0 |
| 3-methylcinnamoylguanidine | 3 | 3 | 0 |
| cinnamoylguanidine | 4 | 4 | 0 |
| trans-3-(1-napthyl)acryloylguanidine | 5.5 | 7 | 2.25 |
| 6-methoxy-2-naphthoylguanidine | 5.5 | 5 | 0.25 |
| 4-phenylbenzoylguanidine | 7 | 11 | 16 |
| (5-phenyl-penta-2,4-dienoyl)guanidine | 8 | 9 | 1 |
| N-(3-phenylpropanoyl)-N'-phenylguanidine | 9 | 12 | 9 |
| Hexamethylene amiloride | 10 | 6 | 16 |
| 2-(2-napthyl)acetoylguanidine | 11 | 10 | 1 |
| (trans-2-phenylcyclopropanecarbonyl)guanidine | 12 | 8 | 16 |
| Sum $di^2$ | | | 61.5 |
| Spearman correlation coefficient | | | 0.785 |
| P value | | | >0.01 |

TABLE 19b

| Compounds Ordered by p24 rank order | Vpu Bacterial score | Bacterial assay rank order | At least 1x log reduction seen in p24 assay? |
|---|---|---|---|
| (3-bromocinnamoyl)guanidine | 4.3 | 1 | yes |
| 3-(trifluoromethyl)cinnamoyl-guanidine | 3.7 | 2 | yes |
| 3-methylcinnamoylguanidine | 3.4 | 3 | yes |
| cinnamoylguanidine | 3.0 | 4 | yes |
| trans-3-(1-napthyl)acryloylguanidine | 2.9 | 5.5 | yes |
| 6-methoxy-2-naphthoylguanidine | 2.9 | 5.5 | yes |
| 4-phenylbenzoylguanidine | 2.8 | 7 | no |
| (5-phenyl-penta-2,4-dienoyl)-guanidine | 2.6 | 8 | no |
| N-(3-phenylpropanoyl)-N'-phenylguanidine | 2.2 | 9 | no |
| Hexamethylene amiloride | 1.9 | 10 | no |
| 2-(2-napthyl)acetoylguanidine | 1.2 | 11 | no |
| (trans-2-phenylcyclopropanecarbonyl)-guanidine | 0.4 | 12 | no |

EXAMPLE 58.4

Correlation Between Percent Inhibition of MHV Plaque Formation and MHV-E Bacterial Bio-Assay Score A positive correlation was seen between the activity scores assigned to compounds when tested in the Mouse Hepatitis Virus E-protein bacterial bio-assay and the percent inhibition exhibited by these compounds in the Mouse Hepatitis Virus plaque assay.

EXAMPLE 58.5

Method

MHV plaque reduction activity data for 96 compounds screened were sorted from greatest to least percent plaque reduction and rank orders were assigned to the list of compounds. This was performed for the data generated by exposure to both 10 µM and 1 µM concentrations of the compounds, giving rise to two rank order lists.

Similarly, a rank order list was generated for the MHVE bacterial bioassay scores for the same 96 compounds. Where one or more compounds had the same score, the rank values for that group were averaged.

Spearman's statistical test for [as described in "Mathematical Statistics with Applications" ($2^{nd}$ edn): Mendenhall, W., Scheaffer, R L., & Wackerly, D D. Duxbury Press, Boston Mass.,—1981] was used to compare rank orders. Briefly, this involved calculating the Sum of squares (SS) of the differences between rank values for each compound, and then generating the Spearman's Rank Correlation coefficient (Rs) according to the formula: $Rs=1-(6 \cdot SS/n(n^2-1))$, where n is the number of compounds ranked (96 in this case). Rs is then compared to a Table of critical values to determine statistical significance (P values).

EXAMPLE 58.6

Summary of Results

This table summarises the Rs and P values generated as a result of the indicated pairwise comparisons between rank orders.

TABLE 20

| Comparison | | Rs | P | +ive correlation |
|---|---|---|---|---|
| Plaque at 10 µM | Plaque at 1 µM | 0.689 | >99.5 | Yes |
| Bacterial | Plaque at 10 µM | 0.444 | >99 | Yes |
| | Plaque at 1 µM | 0.406 | >98.5 | Yes |
| | Randomised order | −0.382 | n/s | No |

EXAMPLE 58.7

Conclusions

The rank order comparison of 96 compounds assayed in the bacterial bio-assay and the antiviral assay show that MHVE bacterial assay rank order for the compounds tested is significantly positively correlated with the rank orders generated by the MHV plaque reduction assay. The significant correlation between the assays is highly indicative that either assay may be utilised to identify compounds that may be useful. The bacterial assay may thereby be a useful tool in screening for compounds that exhibit anti-viral activity.

EXAMPLE 58.8

Correlation Between Percent Inhibition of 229E Plaque Formation and 229E-E Bacterial Bio-Assay Score A positive correlation was seen between the activity scores assigned to compounds when tested in the Human Coronavirus 229E E-protein bacterial bio-assay and the percent inhibition exhibited by these compounds in the Human Coronavirus 229E plaque assay.

EXAMPLE 58.9

Method 229E plaque reduction activity data for 97 compounds screened against 2.5 μM compound concentration were sorted from greatest to least percent plaque reduction and rank orders were assigned to the list of compounds. Similarly, a rank order list was generated for the 229E E bacterial bioassay scores for the same 97 compounds. Where one or more compounds had the same score, the rank values for that group were averaged.

Spearman's statistical test for [as described in "Mathematical Statistics with Applications" ($2^{nd}$ edn): Mendenhall, W., Scheaffer, R L., & Wackerly, D D. Duxbury Press, Boston Mass.—1981] was used to compare rank orders. Briefly, this involves calculating the Sum of squares (SS) of the differences between rank values for each compound, and then generating the Spearman's Rank Correlation coefficient (Rs) according to the formula: $Rs=1-(6\cdot SS/n(n^2-1))$, where n is the number of compounds ranked (97 in this case). Rs is then compared to a Table of critical values to determine statistical significance (P values).

EXAMPLE 58.9.1

Summary of Results and Conclusions

This table summarises the Rs and P values generated as a result of the indicated pairwise comparisons between rank orders.

TABLE 21

| Comparison | | Rs | P | +ive correlation |
|---|---|---|---|---|
| Plaque at 2.5 μM | Bacterial | 0.584 | >99.5 | Yes |
| | randomised | −0.382 | n/s | No |

The results above indicate that the 229E bacterial assay rank order for the compounds tested is significantly positively correlated with the rank orders generated by the 229E plaque reduction assay. This result combined with that shown in Examples 49.1 and 49.4, provides strong evidence that either assay may be utilised to identify compounds that may be useful. The bacterial assay may thereby be a useful tool in screening for compounds that exhibit anti-viral activity.

Those skilled in the art will appreciate that the invention described herein is susceptible to variations and modifications other than those specifically described. It is to be understood that the invention includes all such variations and modifications The invention also includes all of the steps, features, compositions and compounds referred to or indicated in this specification, individually or collectively, and any and all combinations of any two or more of said steps or features.

BIBLIOGRAPHY

Barry, M., Mulcahy, F. and Back, D-J., Br J Clin Pharmacol, 45: 221 (1998)

Deeks, S. G., West J Med, 168:133 (1998)

Miles, S. A., J Acquir Immune Defic Syndr Hum Retrovirol, 16 Suppl 1: S36 (1997)

Miles, S. A., J. Acquir Immune Defic Syndr Hum Retrovirol, 16 Suppl 1: S I (1998)

Moyle, G. J., Gazzard, B. G., Cooper, D. A. and Gatell, J., Drugs, 55:383 (1998)

Rachlis, A. R. and Zarowny, D. P., Cmaj, 158:496 (1998)

Vella, S., Fragola, V. and Palmisano, L., J Biol Regul Homeost Agents, 11:60 (1997)

Volberding, P. A. and Deeks, S. G., Jama, 279:1343 (1998)

Volberding, P. A., Hosp Pract (Off Ed), 33:81-4, 87-90, 95-6 passim. (1998)

Miller, R. H. and Sarver, N., Nat Med, 3:389 (1997)

Mitsuya, H., Enzyme Inhibition, 6:1 (1992)

Moore, J. P., Science, 276:51 (1997)

Thomas, M. and Brady, L., Trends Biotechnol., 15:167 (1997)

Balliet, J. W., Kolson, D. L., Eiger, G., Kim, F. M., McGann, K. A., Srinivasan, A. and Collman, R., Virology, 200:623 (1994)

Westervelt, P., Henkel, T., Trowbridge, D. B., Orenstein, J., Heuser, J., Gendelman, H. E. and Ratner, L., J Virol, 66:3925 (1992)

Ewart, G. D., Sutherland, T., Gage, P. W. and Cox, G. B., J Virol, 70:7108 (1996)

Schubert, U., Henklein, P., Boldyreff, B., Wingender, E., Strebel, K. and Porstmann, T. J Mol Biol, 236:16 (1994)

Friborg, J., Ladha, A., Gottlinger, H., Haseltine, W. A. and Cohen, E. A., Journal of Acquired Immune Deficiency Syndromes & Human Retrovirology, 8:10 (1995)

Fu, J., Tan, B. H., Yap, E. H., Chan, Y. C. and Tan, Y. H. (1992) Full-length cDNA sequence of dengue type 1 virus (Singapore strain S275/90). Virology 188 (2), 953-958

Love, C. A., Lilley, P. E. and Dixon, N. E., *Escherichia coli*. Gene, in press. (1996)

Yamato, I., Kotani, M., Oka, Y. and Anraku, Y., *Escherichia coli*. Journal of Biological Chemistry, 269:5729 (1994)

Rosen, B. R., ATP-coupled solute transport systems. *Escherichia coli* and *Salmonella typhimurium*: Cellular and molecular biology 1: (1987) Editor: Neidhardt, F. C. American Society for Microbiology.

Piller, S. C., Ewart, G. D., Premkumar, A., Cox, G. B. and Gage, P. W., Proceedings of the National Academy of Sciences of the United States of America, 93:111 (1996)

Lu, Y. A., Clavijo, P., Galantino, M., Shen, Z. Y., Liu, W. and Tam, J. P., Molecular Immunology, 28:623 (1991)

Harlow, E. and Lane, D., (1988) Antibodies: A laboratory manual. (ed). Cold Spring Harbor Laboratory, Cold Spring Harbor, N.Y., 'Vol:'.

Varadhachary, A. and Maloney. P-C., Molecular Microbiology, 4:1407 (1990)-44

New, R. C. C., (1990). Liposomes: A practical approach. The Practical Approach Series.

Kuhn R J, Zhang W, Rossmann M G, Pletnev S V, Corver J, Lenches E, Jones C T, Mukhopadhyay S, Chipman P R, Strauss E G, Baker T S, Strauss J H. (2002). Structure of dengue virus: implications for flavivirus organization, maturation, and fusion. Cell. 2002 Mar. 8; 108(5):717-25.

Rickwood, D., Harries, B. D. (eds). IRL Press, Oxford.

Miller, C., (1986) Ion channel reconstitution. (ed). Plenum Press, New York and London.

Fear, W. R., Kesson, A. M., Naif, H., Lynch, G. W. and Cunningham, A. L., J. Virol, 72:1334 (1998)

Kelly, M. D., Naif, H., Adams, S. L., Cunningham, A. L. and Lloyd, A. R., J. Immunol, 160:3091 (1998)

New, R. C. C. (ed.), Liposomes: a practical approach. IRL Press, Oxford (1990) Grice, A. L., Kerr, I. D. and Sansom, M. S., FEBSLett, 405(3):299-304 (1997) Moore, P. B., Zhong, Q., Husslein, T. and Klein, M. L., FEBS Lett, 431(2):143-148 (1998) Schubert, U., Bour, S., Ferrermontiel, A. V., Montal, M., Maldarelli, F. and Strebel, K., Journal of Virology, 70(2):809-819 (1996a)

Sunstrom N A, Premkumar L S, Premkumar A, Ewart G, Cox G B, Gage P W (1996), Ion channels formed by NB, an influenza B virus protein. J Membr Biol. 1996 March; 150(2): 127-32

Willbold, D., Hofftnann, S. and Rosch, P., Eur J Biochem, 245(3):581-8 (1997) Wray, V., Kinder, R., Federau, T., Henklein, P. Bechinger, B. and Schubert, U., Biochemistry, 38(16):5272-82 (1999)

The invention claimed is:

1. A pharmaceutical composition comprising a compound selected from the group consisting of:

4-phenylbenzoylguanidine

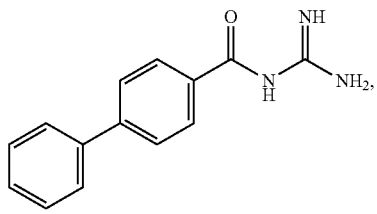 [SMILES: N=C(N)NC(=O)c1ccc(-c2ccccc2)cc1]

N-(3-phenylpropanoyl)-N'-phenyl-guanidine

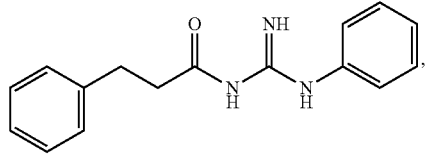 [SMILES: N=C(NC(=O)CCc1ccccc1)Nc1ccccc1]

N,N'-bis(3-phenylpropanoyl)guanidine

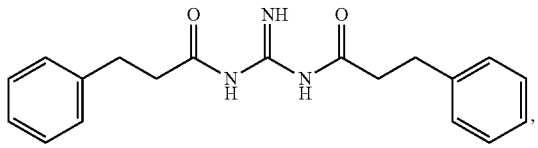 [SMILES: N=C(NC(=O)CCc1ccccc1)NC(=O)CCc1ccccc1]

N-(6-Hydroxy-2-naphthoyl)-N'-phenyl-guanidine

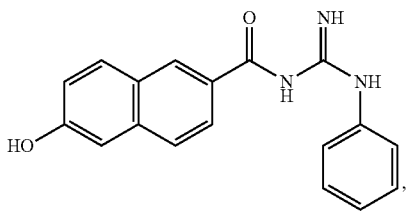 [SMILES: N=C(NC(=O)c1ccc2cc(O)ccc2c1)Nc1ccccc1]

N-Benzoyl-N'-cinnamoylguanidine

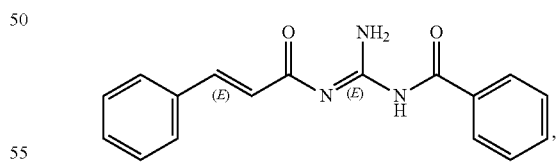

(5-Phenyl-penta-2,4-dienoyl)guanidine

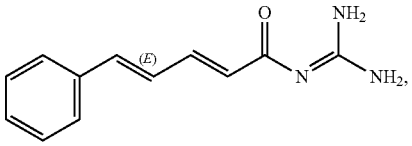 [SMILES: NC(N)=NC(=O)/C=C/C=C/c1ccccc1]

4-phenylcinnamoylguanidine

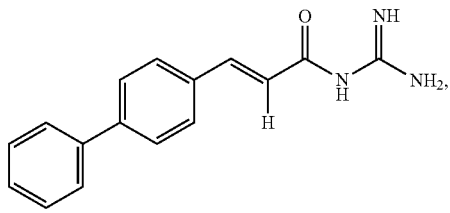 [SMILES: N=C(N)NC(=O)/C=C/c1ccc(-c2ccccc2)cc1]

5-(3'-bromophenyl)penta-2,4-dienoylguanidine

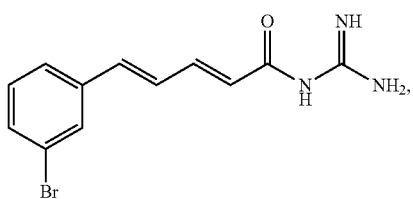 [SMILES: N=C(N)NC(=O)/C=C/C=C/c1cccc(Br)c1]

3-phenylcinnamoylguanidine

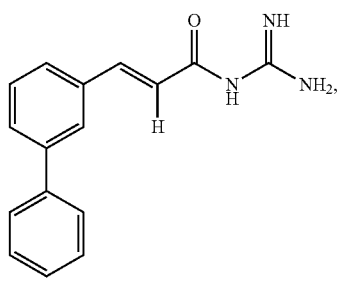 [SMILES: N=C(N)NC(=O)/C=C/c1cccc(-c2ccccc2)c1]

5-(2'-bromophenyl)penta-2,4-dienoylguanidine

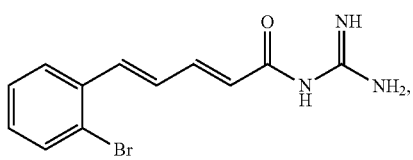 [SMILES: N=C(N)NC(=O)/C=C/C=C/c1ccccc1Br]

2-cyclohexylcinnamoylguanidine

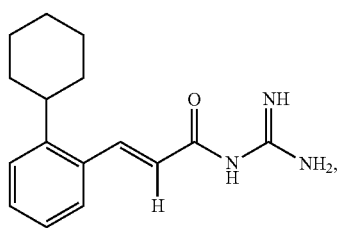 [SMILES: N=C(N)NC(=O)/C=C/c1ccccc1C1CCCCC1]

2-phenylcinnamoylguanidine

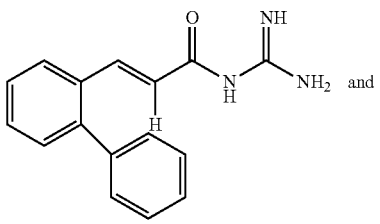 [SMILES: N=C(N)NC(=O)/C=C/c1ccccc1-c1ccccc1]

2-(cyclohex-1-en-1yl)cinnamoylguanidine

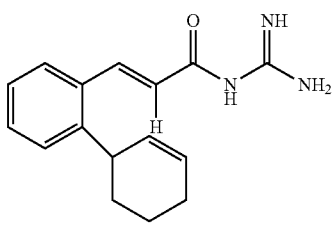 [SMILES: N=C(N)NC(=O)/C=C/c1ccccc1C1C=CCCC1]

and a pharmaceutically acceptable salt, wherein the composition has anti-viral activity.

2. The compound according to claim 1 wherein the compound is selected from:

2-phenylcinnamoylguanidine, 3-phenylcinnamoylguanidine, 4-phenyl cinnamoylguanidine, 5-(2'-bromophenyl)penta-2,4-dienoylguanidine, 5-(3'-bromophenyl)penta-2,4-dienoylguanidine, N-(6-Hydroxy-2-naphthoyl)-N'-phenylguanidine, and N,N'-Bis(3-phenylpropanoyl)guanidine, or a pharmaceutically acceptable salt thereof.

3. A method for the therapeutic or prophylactic treatment of a subject infected with or exposed to a virus, comprising administering to the subject a compound according to claim 1, wherein said virus is a Lentivirus, Human Immunodeficiency Virus (HIV), a Coronavirus, the Hepatitis C virus or Equine Arteritis virus.

4. The pharmaceutical composition according to claim 1 wherein the compound is selected from:

N-(6-Hydroxy-2-naphthoyl)-N'-phenyl-guanidine, 5-(3'-bromophenyl)penta-2,4-dienoylguanidine, 5-(2'-bromophenyl)penta-2,4-dienoylguanidine and 2-phenylcinnamoylguanidine.

5. The pharmaceutical composition according to claim 1, wherein the composition has activity against Lentivirus, Human Immunodeficiency Virus (HIV), a Coronavirus, Hepatitis C virus or Equine Arteritis virus.

* * * * *